(12) United States Patent
Josien et al.

(10) Patent No.: US 7,122,675 B2
(45) Date of Patent: Oct. 17, 2006

(54) GAMMA SECRETASE INHIBITORS

(75) Inventors: Hubert B. Josien, Hoboken, NJ (US); John W. Clader, Cranford, NJ (US); Theodros Asberom, West Orange, NJ (US); Dmitri A. Pissarnitski, Scotch Plains, NJ (US)

(73) Assignee: Schering Corporation, Kenilworth, NJ (US)

( * ) Notice: Subject to any disclaimer, the term of this patent is extended or adjusted under 35 U.S.C. 154(b) by 459 days.

(21) Appl. No.: 10/210,803

(22) Filed: Aug. 1, 2002

(65) Prior Publication Data
US 2003/0216380 A1 Nov. 20, 2003

Related U.S. Application Data
(60) Provisional application No. 60/310,068, filed on Aug. 3, 2001.

(51) Int. Cl.
| | |
|---|---|
| *C07D 211/56* | (2006.01) |
| *C07D 409/00* | (2006.01) |
| *C07D 279/00* | (2006.01) |
| *A01N 43/40* | (2006.01) |
| *A61K 31/54* | (2006.01) |

(52) U.S. Cl. ............... 546/223; 546/194; 546/191; 546/208; 546/210; 546/212; 546/197; 546/193; 544/58.4; 544/130; 544/335; 544/365; 514/227.8; 514/235.5; 514/256; 514/316; 514/321; 514/326

(58) Field of Classification Search ......... 546/223, 546/194, 191, 208, 210, 212, 197; 544/58.4, 544/130, 335, 360; 514/227.8, 235.5, 256, 514/316, 318, 329, 326, 314, 253.13
See application file for complete search history.

(56) References Cited

U.S. PATENT DOCUMENTS
5,646,167 A * 7/1997 MacPherson et al.

FOREIGN PATENT DOCUMENTS
| | | | |
|---|---|---|---|
| FR | 2802206 | * | 6/2001 |
| WO | WO 00/50391 | | 8/2000 |
| WO | WO 01/81308 | * | 4/2001 |
| WO | WO 02/24649 | * | 9/2001 |

OTHER PUBLICATIONS
CAS printout for MacPherson et al. (Chem Abstract 127: 162116.*

Hansen, H., *"Multistep Solution–Phase Parallel Synthesis of Spiperone Analogues"*, Bioorganic & Medicinal Chemistry Letters, vol. 10, 2000, pp. 2435–2439.

* cited by examiner

*Primary Examiner*—Richard Raymond
*Assistant Examiner*—Paul V. Ward
(74) *Attorney, Agent, or Firm*—Thomas A. Blinka

(57) ABSTRACT

Novel aryl and heteroaryl sulfonamides are disclosed. The sulfonamides, which are gamma secretase inhibitors, are represented by the formula:

$$(R^1)_r-Ar^1-\overset{O_2}{\underset{}{S}}-N(-Y-Ar^2-(R^2)_q)-\text{piperidine}(R^4)_t, N-R^5$$

(I)

wherein $Ar^1$ and $Ar^2$ independently represent aryl or heteroaryl and Y represents a bond or a $-(C(R^3)_2)_{1-3}$ group. Also disclosed is a method of inhibiting gamma secretase, and a method of treating Alzheimer's disease using the compounds of formula I.

15 Claims, No Drawings

GAMMA SECRETASE INHIBITORS

This patent application claims priority from provisional application Ser. No. 60/310,068 filed Aug. 3, 2001.

BACKGROUND

WO 00/50391, published Aug. 13, 2000, discloses compounds having a sulfonamide moiety that are useful for the treatment and prevention of Alzheimer's Disease and other diseases relating to the deposition of amyloid protein.

In view of the present interest in the treatment or prevention of neurodegenerative diseases, such as Alzheimer's Disease, a welcome contribution to the art would be compounds for use in such treatment or prevention. This invention provides such a contribution.

SUMMARY OF THE INVENTION

This invention provides compounds that are inhibitors (e.g., antagonists) of Gamma Secretase and have the formula:

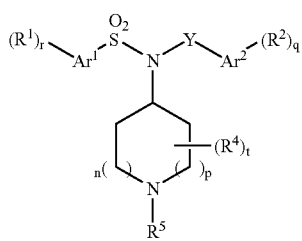

(I)

or pharmaceutically acceptable salts or solvates thereof, wherein:

(A) $Ar^1$ and $Ar^2$ are independently selected from aryl or heteroaryl;

(B) Y is bond, or Y is a —$(C(R^3)_2)_{1-3}$— group;

(C) each $R^1$ is independently selected from:
   (1) —$(C_1-C_6)$alkyl;
   (2) aryl;
   (3) aryl substituted with one or more substituents independently selected from: halogen, $CF_3$, $(C_1-C_6)$alkyl, $(C_1-C_6)$alkoxy, $OCF_3$, $NH_2$, or CN;
   (4) heteroaryl;
   (5) heteroaryl substituted with one or more substituents independently selected from: halogen, $CF_3$, $(C_1-C_6)$alkyl, $(C_1-C_6)$alkoxy, $OCF_3$, $NH_2$, or CN;
   (6) halogen;
   (7) —$CF_3$;
   (8) —$OCF_3$;
   (9) —CN;
   (10) —$NO_2$;
   (11) —$NH_2$;
   (12) —$C(O)NH(C_1-C_6)$alkyl;
   (13) —$C(O)N((C_1-C_6)$alkyl$)_2$ wherein each $(C_1-C_6)$ alkyl group is the same or different;
   (14) —$C(O)N((C_1-C_6)$alkyl$)_2$ wherein each $(C_1-C_6)$ alkyl group is the same or different, and said $(C_1-C_6)$ alkyl groups taken together with the nitrogen to which they are bound form a ring;
   (15) —$NHC(O)(C_1-C_6)$alkyl;
   (16) —$NHC(O)O(C_1-C_6)$alkyl;
   (17) —$NHC(O)NH(C_1-C_6)$alkyl;
   (18) —$NHSO_2(C_1-C_6)$alkyl;
   (19) —OH;
   (20) —$OC(O)(C_1-C_6)$alkyl;
   (21) —$O(C_1-C_6)$alkyl,
   (22) —Oaryl; or
   (23) —$Oar(C_1-C_6)$alkyl;

(D) each $R^2$ is independently selected from:
   (1) —$(C_1-C_6)$alkyl;
   (2) halogen;
   (3) —$CF_3$;
   (4) —$OCF_3$;
   (5) —CN;
   (6) —$NO_2$;
   (7) —$NH_2$;
   (8) —$C(O)O(C_1-C_6)$alkyl;
   (9) —$C(O)NH(C_1-C_6)$alkyl;
   (10) —$N(C_1-C_6$alkyl$)_2$ wherein each $C_1-C_6$ alkyl substituent is the same or different;
   (11) —$N(C_1-C_6$alkyl$)_2$ wherein each $C_1-C_6$alkyl substituent is the same or different, and the $C_1-C_6$alkyl substituents together with the nitrogen atom to which they are bound form a ring;
   (12) —$NHC(O)(C_1-C_6)$alkyl;
   (13) —$NHC(O)O(C_1-C_6)$alkyl;
   (14) —$NHC(O)NH(C_1-C_6)$alkyl;
   (15) —$NHSO_2(C_1-C_6)$alkyl;
   (16) —OH;
   (17) —$OC(O)(C_1-C_6)$alkyl;
   (18) —$O(C_1-C_6)$alkyl;
   (19) —Oaryl;
   (20) —$Oar(C_1-C_6)$alkyl;
   (21) aryl;
   (22) aryl substituted with one or more substituents independently selected from: halogen, $CF_3$, $(C_1-C_6)$ alkyl, $(C_1-C_6)$alkoxy, $OCF_3$, $NH_2$, or CN;
   (23) heteroaryl;
   (24) heteroaryl substituted with one or more substituents independently selected from: halogen, $CF_3$, $(C_1-C_6)$alkyl, $(C_1-C_6)$alkoxy, $OCF_3$, $NH_2$, or CN;
   (25) a group selected from:

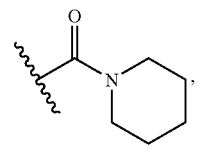

(8.0)

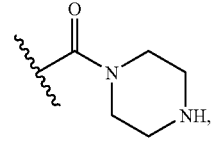

(9.0)

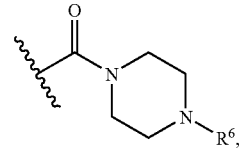

(10.0)

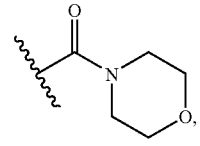

(11.0)

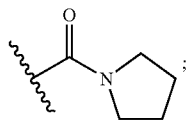

(12.0)

(26) —C(O)N((C$_1$–C$_6$)alkyl)$_2$ wherein each alkyl group is independently selected; or
(27) —C(O)N((C$_1$–C$_6$)alkyl)$_2$ wherein each alkyl group is independently selected and wherein the alkyl groups taken together with the nitrogen atom form a heterocycloalkyl ring;

(E) each R$^3$ is independently selected from H or —(C$_1$–C$_3$)alkyl;

(F) each R$^4$ is independently selected from:
  (1) —(C$_1$–C$_3$)alkyl;
  (2) —OH; or
  (3) —O(C$_1$–C$_3$)alkyl;

(G) R$^5$ is selected from:
  (1) hydrogen;
  (2) —(C$_1$–C$_6$)alkyl;
  (3) aryl;
  (4) heteroaryl;
  (5) —(C$_1$–C$_3$)alkylene-O(C$_1$–C$_3$)alkyl;
  (6) —(C$_1$–C$_6$)alkylene-S(O)$_{0-2}$(C$_1$–C$_3$)alkyl;
  (7) —(C$_1$–C$_6$)alkylene-S(O)$_{0-2}$NH(C$_1$–C$_3$)alkyl;
  (8) —C(O)(C$_1$–C$_6$)alkyl;
  (9) —C(O)aryl;
  (10) —C(O)ar(C$_1$–C$_3$)alkyl;
  (11) —C(O)heteroaryl;
  (12) —C(O)heteroar(C$_1$–C$_3$)alkyl;
  (13) —C(O)O(C$_1$–C$_6$)alkyl;
  (14) —C(O)NH(C$_1$–C$_6$)alkyl;
  (15) —C(O)N((C$_1$–C$_6$)alkyl)$_2$ wherein each C$_1$–C$_6$alkyl group is the same or different;
  (16) —C(O)N((C$_1$–C$_6$)alkyl)$_2$ wherein each C$_1$–C$_6$alkyl group is the same or different and wherein the C$_1$–C$_6$ alkyl groups taken together with the nitrogen to which they are bound form a heterocycloalkyl ring;
  (17) —C(O)(C$_1$–C$_3$)alkylene-NH(C$_1$–C$_3$)alkyl;
  (18) —C(O)(C$_1$–C$_3$)alkylene-N((C$_1$–C$_3$)alkyl)$_2$ wherein each alkyl group is independently selected;
  (19) —SO$_2$(C$_1$–C$_6$)alkyl;
  (20) —SO$_2$NH(C$_1$–C$_6$)alkyl;
  (21) —SO$_2$N((C$_1$–C$_6$)alkyl)$_2$ wherein each C$_1$–C$_6$ alkyl is the same or different;
  (22) —SO$_2$N((C$_1$–C$_6$) alkyl)$_2$ wherein each C$_1$–C$_6$alkyl is the same or different, and wherein the C$_1$–C$_6$ alkyl groups taken together with the nitrogen to which they are bound form a heterocycloalkyl ring; or
  (23) a group of the formula:

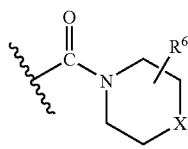

(13.0)

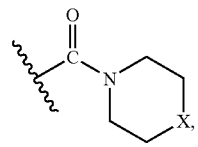

(13.1)

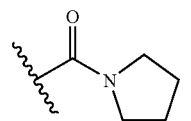

(14.0)

or

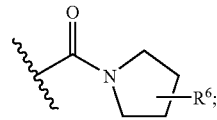
(15.0)

(H) R$^6$ is —H or —(C$_1$–C$_6$) alkyl;
(I) X is selected from: CH$_2$, O, S, SO, SO$_2$, or N—R$^7$;
(J) R$^7$ is selected from:
  (1) —(C$_1$–C$_6$) alkyl;
  (2) —(C$_3$–C$_6$)cycloalkyl;
  (3) —(C1–C3)alkylene-(C3–C6)cycloalkyl;
  (4) aryl;
  (5) ar(C$_1$–C$_3$)alkyl;
  (6) heteroaryl;
  (7) heteroar(C$_1$–C$_3$)alkyl;
  (8) —C(O)(C$_1$–C$_6$) alkyl;
  (9) —C(O)aryl;
  (10) —C(O)ar(C$_1$–C$_3$)alkyl;
  (11) —C(O)heteroaryl;
  (12) —C(O)heteroar(C$_1$–C$_3$)alkyl;
  (13) —C(O)O(C$_1$–C$_6$) alkyl;
  (14) —C(O)NH(C$_1$–C$_6$)alkyl;
  (15) —C(O)N((C$_1$–C$_6$) alkyl)$_2$ wherein each C$_1$–C$_6$ alkyl group is the same or different;
  (16) —C(O)N((C$_1$–C$_6$)alkyl)$_2$ wherein each C$_1$–C$_6$alkyl group is the same or different, and the C$_1$–C$_6$alkyl groups taken together with the nitrogen to which they are bound form a heterocycloalkyl ring;
  (17) —C(O)(C$_1$–C$_3$)alkylene-NH(C$_1$–C$_3$)alkyl;
  (18) —C(O)(C$_1$–C$_3$)alkylene-N((C$_1$–C$_3$)alkyl)$_2$ wherein the C$_1$–C$_3$alkyl groups are the same or different; or
  (19) —(C$_1$–C$_3$)alkylene-O—(C$_1$–C$_3$)alkyl;

(K) n and p are independently selected from 0 to 3 to form a 4 to 7 member ring;
(L) r is 0 to 3;
(M) q is 0 to 3; and
(N) t is 0 to 3.

This invention also provides a pharmaceutical composition comprising an effective amount of at least one compound of formula I and at least one pharmaceutically acceptable carrier.

This invention also provides a method for inhibiting gamma-secretase in a patient in need of such treatment comprising administering to said patient an effective amount of a compound of formula I.

This invention also provides a method of treating neurodegenerative diseases in a patient in need of such treatment comprising administering to said patient an effective amount of a compound of formula I.

This invention also provides a method of inhibiting the deposition of amyloid protein (e.g., beta amyloid) in, on or around neurological tissue (e.g., the brain) in a patient in need of such treatment comprising administering to said patient an effective amount of a compound of formula I.

This invention also provides a method of treating Alzheimer's disease in a patient in need of such treatment comprising administering to said patient an effective amount of a compound of formula I.

DETAILED DESCRIPTION OF THE INVENTION

As used herein the following terms have the following meanings unless otherwise defined:

Patient includes both humans and other mammals. "Mammal" means humans and other animals.

AcOEt: represents ethyl acetate;

AcOH: represents acetic acid;

alkyl: (including the alkyl portions of alkoxy, alkylamino and dialkylamino)—represents straight and branched carbon chains and contains from one to twenty carbon atoms, preferably one to six carbon atoms, said alkyl group being optionally substituted with one or more (e.g., 1, 2 or 3) substituents independently selected from: halogen, —OH, —OCH$_3$, —NH$_2$, —NHCH$_3$, or —N(CH$_3$)$_2$;

alkylene: represents a —(CH$_2$)$_m$— group wherein m is 1 to 20, generally 1 to 6 and more usually 1 to 4, said alkylene group can be optionally substituted with one or more (e.g., 1 to 3) substituents independently selected from: halogen, —OH, —OCH$_3$, —NH$_2$, —NHCH$_3$, or —N(CH$_3$)$_2$;

ar: represents aryl as defined below;

aralkyl (arylalkyl): represents an aryl group, as defined below, bound to an alkyl group, as defined above, wherein said alkyl group is bound to a molecule (e.g., a compound of the claimed invention or an intermediate to a compound of the invention);

ar(C$_1$–C$_3$)alkyl: represents an arylalkyl group wherein said alkyl group has 1 to 3 carbons;

aryl: (including the aryl portion of aryloxy, aryloxy and aralkyl (i.e., arylalkyl)) represents a carbocyclic group containing from 6 to 15 carbon atoms and having at least one aromatic ring (e.g., phenyl, naphthyl, phenanthryl, tetrahydronaphthyl or indanyl), with all available substitutable carbon atoms of the carbocyclic group being intended as possible points of attachment; said carbocyclic group being optionally substituted with one or more (e.g., 1 to 3) substituents independently selected from: halo, alkyl, hydroxy, alkoxy, —CN, phenyl, phenoxy, —CF$_3$, amino, alkylamino, dialkylamino, aryl (provided that if this aryl group is optionally substituted with one or more aryl groups these latter aryl groups are not further substituted with aryl groups), aralkoxy (provided that if the aryl moiety of said aralkoxy (i.e., arylalkoxy) group is optionally substituted with one or more aryl groups these latter aryl groups are not further substituted with aryl groups), aryloxy (provided that if the aryl moiety of said aryloxy group is optionally substituted with one or more aryl groups these latter aryl groups are not further substituted with aryl groups), —S(O)$_{0-2}$-aryl (provided that if the aryl moiety of said —S(O)$_{0-2}$-aryl group is optionally substituted with one or more aryl groups these latter aryl groups are not further substituted with aryl groups), —COOR$^8$ or —NO$_2$; wherein said R$^8$ represents H, alkyl, aryl (provided that if said aryl moiety is optionally substituted with one or more aryl containing groups these latter aryl containing groups are not further substituted with aryl containing groups), or aralkyl (e.g., benzyl) (provided that if said aryl moiety of said aralkyl group is optionally substituted with one or more aryl containing groups these latter aryl containing groups are not further substituted with aryl containing groups);

BOC: represents tert-butoxycarbonyl;

"Cycloalkyl" represents a non-aromatic ring straight or branched system comprising about 3 to about 8 carbon atoms. Preferred cycloalkyl rings contain about 3 to about 6 ring atoms. Non-limiting examples of suitable straight cycloalkyls include cyclopropyl, cyclobutyl, cyclopentyl, cyclohexyl and the like; non-limiting examples of suitable branched cycloalkyls include 2-methylcyclopropyl, 3-ethylcyclopentyl and the like;

"(C1–C3)alkylene-(C3–C6)cycloalkyl" represents a (C3–C6)cycloalkyl group attached through a (C1–C3) alkylene group to a main molecule. Non-limiting example of a suitable (C1–C3)alkylene-(C3–C6)cycloalkyl is:

—C(O)ar(C$_1$–C$_3$)alkyl: represents a —C(O)-aralkyl group wherein the alkyl group has 1 to 3 carbons;

—C(O)heteroar(C$_1$–C$_3$)alkyl: represents a —C(O)-heteroaralkyl group wherein the alkyl group has 1 to 3 carbons;

—(C(R$^3$)$_2$)$_{1-3}$—: represents a one to three carbon alkylene group wherein each carbon is optionally substituted with the same or different (C$_1$–C$_3$)alkyl group;

DCE: represents 1,2-dichloroethane;

DEAD: represents diethyl azodicarboxylate;

DMAP: represents 4-dimethylaminopyridine;

DME: represents 1,2-dimethoxyethane;

DMF: represents N,N-dimethylformamide;

EDCI: represents 1-(3-dimethylaminopropyl)-3-ethyl carbodiimide hydrochloride;

Et$_3$N: represents triethylamine;

Et$_2$O: represents diethyl ether;

EtOAc: represents ethyl acetate;

EtOH: represents ethanol;

FMOC: represents 9-fluorenylmethoxycarbonyl;

halogen (halo): represents fluoro, chloro, bromo and iodo;

heteroaryl: (including the heteroaryl portion of heteroarylalkyl) represents a monocyclic, bicyclic or tricyclic group having at least one heteroatom (e.g., 1, 2 or 3) independently selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms, e.g., triazolyl, imidazolyl, thienyl, furanyl, quinolyl, isoquinolyl, benzofuranyl, benzopyranyl, benzothienyl, thiazolyl, indolyl, naphthyridinyl, pyridyl (e.g., 2-, 3- or 4-pyridyl) or pyridyl N-oxide (e.g., 2-, 3- or 4-pyridyl N-oxide), wherein pyridyl N-oxide can be represented as:

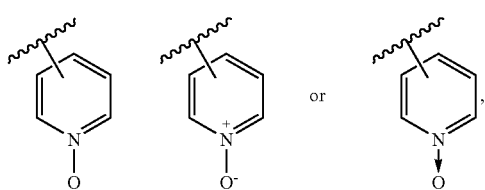

and with all available substitutable carbon and heteroatoms of the cyclic group being intended as possible points of attachment, said cyclic group being optionally substituted with one or more (e.g., 1, 2 or 3) groups independently selected from halo, alkyl, aryl, aralkyl, hydroxy, alkoxy, phenoxy, —$NO_2$, —$CF_3$, amino, alkylamino, dialkylamino, —$COOR^8$ (wherein $R^8$ is as defined above), or heteroaryl (provided that if this heteroaryl group, as defined above, is optionally substituted with one or more heteroaryl groups these latter heteroaryl groups are not further substituted with heteroaryl groups);

heteroaralkyl (heteroarylalkyl): represents a heteroaryl group, as defined above, bound to an alkyl group, as defined above, wherein said alkyl group is bound to a molecule (e.g., a compound of the claimed invention or an intermediate to a compound of the invention);

heteroar($C_1$–$C_3$)alkyl: represents a heteroarylalkyl group wherein the alkyl group has 1 to 3 carbons;

HOBT: represents 1-hydroxybenzotriazole;

MeOH: represents methanol;

—Oar($C_1$–$C_6$)alkyl: represents a —O-aralkyl group wherein the alkyl group has one to six carbons;

Ph: represents phenyl;

$PPh_3$: represents triphenylphosphine;

TBDMS: represents tert-butyldimethylsilyl;

TFA: represents trifluoroacetic acid;

THF: represents tetrahydrofuran; and

TLC: represents Thin Layer Chromatography.

With reference to the number of moieties (e.g., substituents, groups or rings) in a compound, unless otherwise defined, the phrases "one or more" and "at least one" mean that there can be as many moieties as chemical permitted, and the determination of the maximum number of such moieties is well within the knowledge of those skilled in the art. For example, "one or more" or "at least one" can mean 1 to 6 moieties, and generally 1 to 4 moieties, and usually 1 to 3 moieties.

The term "effective amount" as used in the methods and pharmaceutical compositions of this invention means a therapeutically effective amount, i.e., an amount needed to achieve the desired therapeutic effect.

Those skilled in the art will appreciate that the term "neurodegenerative disease" has its commonly accepted medical meaning and describes diseases and conditions resulting from abnormal function of neurons, including neuronal death and abnormal release of neurotransmitters or neurotoxic substances. In this instance it also includes all diseases resulting from abnormal levels of beta amyloid protein. Examples of such diseases include, but are not limited to, Alzheimer's disease, age-related dementia, cerebral or systemic amyloidosis, hereditary cerebral hemorrhage with amyloidosis, and Down's syndrome.

Lines drawn into the ring systems indicate that the indicated bond may be attached to any of the substitutable ring carbon atoms.

Certain compounds of the invention may exist in different isomeric (e.g., enantiomers and diastereoisomers) forms. The invention contemplates all such isomers both in pure form and in admixture, including racemic mixtures. Enol forms are also included.

The compounds of the invention can be administered as racemic mixtures or enantiomerically pure compounds.

Certain compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

One embodiment of this invention provides compounds of formula Ia:

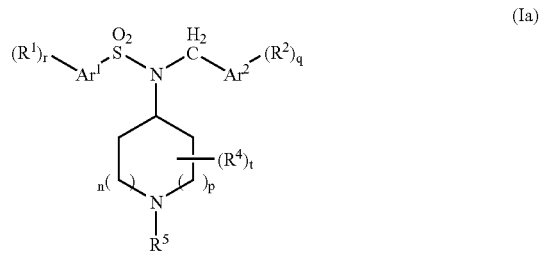

(Ia)

wherein all substituents are as defined for the compounds of formula I.

Another embodiment of this invention provides compounds of formula Ib:

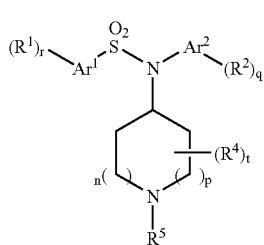

(Ib)

wherein all substituents are as defined for the compounds of formula I.

For compounds of formula I (as well as for compounds of formula Ia or Ib):

(1) $Ar^1$ is preferably a 1,4-arylene, most preferably phenyl;
(2) $R^1$ is preferably selected from: halo, $CF_3$, $OCF_3$, —CN, —$NO_2$, —$NH_2$, —NHC(O)($C_1$–$C_6$)alkyl, —$NHSO_2$($C_1$–$C_6$)alkyl, —O($C_1$–$C_6$)alkyl, or substituted aryl; and most preferably selected from: halo, —$CF_3$, —$OCF_3$, or —O($C_1$–$C_3$)alkyl; when $R^1$ is halo, said halo is preferably chloro;
(3) r is preferably 1;
(4) t is preferably 0;
(5) n and p are selected so that preferably a 3-piperidine, a 4-piperidine or a 3-pyrrolidine ring is formed; most preferably a 3-piperidine ring is formed; and
(6) Y is preferably selected from: a bond or methylene (i.e., —$CH_2$—).

For compounds of formula Ia:

(1) $Ar^2$ is preferably a 1,4-arylene, most preferably phenyl;
(2) $R^2$ is preferably selected from:
 (a) —O($C_1$–$C_3$)alkyl,
 (b) —C(O)O($C_1$–$C_6$)alkyl,
 (c) —C(O)NH($C_1$–$C_6$)alkyl,
 (d) —C(O)N(($C_1$–$C_6$)alkyl)$_2$,
 (e) —C(O)N(($C_1$–$C_6$)alkyl)$_2$ wherein the alkyl groups taken together with the nitrogen to which they are bound form a heterocycloalkyl ring,
 (f) substituted aryl, or
 (g) substituted heteroaryl; and
 most preferably:
 (a) —C(O)O($C_1$–$C_6$)alkyl, or
 (b) substituted heteroaryl; and
 more preferably: 4-$CO_2CH_3$;
(3) q is preferably 1;
(4) $R^5$ is preferably selected from:
 (a) —($C_1$–$C_3$)alkylene-(substituted)aryl,
 (b) substituted aryl,
 (c) —($C_1$–$C_3$)alkylene-(substituted)heteroaryl,
 (d) substituted heteroaryl,
 (e) —C(O)($C_1$–$C_6$)alkyl,
 (f) —C(O)-ar($C_1$–$C_3$)alkyl,
 (g) —C(O)aryl,
 (h) —C(O)-heteroar($C_1$–$C_3$)alkyl,
 (i) —C(O)heteroaryl,
 (j) —C(O)O($C_1$–$C_6$)alkyl,
 (k) —C(O)NH($C_1$–$C_6$)alkyl,
 (l) —C(O)N(($C_1$–$C_6$)alkyl)$_2$,
 (m) —C(O)N(($C_1$–$C_6$)alkyl)$_2$ wherein the alkyl groups taken together with the nitrogen to which they are bound form a heterocycloalkyl ring,
 (n) —C(O)($C_1$–$C_3$)alkylene-NH($C_1$–$C_3$)alkyl, or
 (o) —C(O)($C_1$–$C_3$)alkylene-N(($C_1$–$C_3$)alkyl)$_2$; and
 most preferably:
 (a) —C(O)($C_1$–$C_6$)alkyl,
 (b) —C(O)-ar($C_1$–$C_3$)alkyl,
 (c) —C(O)-heteroar($C_1$–$C_3$)alkyl, or
 (d) —C(O)O($C_1$–$C_6$)alkyl; and
 more preferably:
 (a) —C(O)-ar($C_1$–$C_3$)alkyl, or
 (b) —C(O)-heteroar($C_1$–$C_3$)alkyl.

For compounds of formula Ib:

(1) $Ar^2$ is preferably phenyl;
(2) $R^2$ is preferably selected from: —O($C_1$–$C_3$)alkyl or halogen, and most preferably halogen;
(3) $R^5$ is preferably selected from:
 (a) —($C_1$–$C_3$)alkylene-(substituted)aryl,
 (b) substituted aryl,
 (c) —($C_1$–$C_3$)alkylene-(substituted)heteroaryl,
 (d) substituted heteroaryl,
 (e) —C(O)($C_1$–$C_6$)alkyl,
 (f) —C(O)-ar($C_1$–$C_3$)alkyl,
 (g) —C(O)aryl,
 (h) —C(O)-heteroar($C_1$–$C_3$)alkyl,
 (i) —C(O)heteroaryl,
 (j) —C(O)O($C_1$–$C_6$)alkyl,
 (k) —C(O)NH($C_1$–$C_6$)alkyl,
 (l) —C(O)N(($C_1$–$C_6$)alkyl)$_2$,
 (m) —C(O)N(($C_1$–$C_6$)alkyl)$_2$ wherein the alkyl groups taken together with the nitrogen to which they are bound form a heterocycloalkyl ring,
 (n) —C(O)($C_1$–$C_3$)alkylene-NH($C_1$–$C_3$)alkyl, or
 (o) —C(O)($C_1$–$C_3$)alkylene-N(($C_1$–$C_3$)alkyl)$_2$; and
 most preferably:
 (a) —C(O)NH($C_1$–$C_6$)alkyl,
 (b) —C(O)N(($C_1$–$C_6$)alkyl)$_2$, or
 (c) —C(O)N(($C_1$–$C_6$)alkyl)$_2$ wherein the alkyl groups taken together with the nitrogen to which they are bound form a heterocycloalkyl ring; and
 more preferably:

![structure]

and;

still more preferably:

![structure]

wherein $R^6$ is methyl; and even still more preferably:

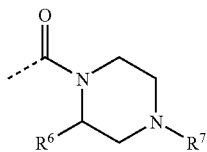

wherein $R^6$ is methyl or hydrogen (yet still more preferably hydrogen), and $R^7$ is —$(C_1$–$C_3)$alkyl, —$(C_1$–$C_3)$alkylene-O—$(C_1$–$C_3)$alkyl, —$(C_3$–$C_6)$cycloalkyl or —$(C1$–$C3)$alkylene-$(C3$–$C6)$cycloalkyl.

Representative compounds of the invention include but are not limited to the compounds of Examples 1 to 230. Preferred compounds of the invention are the compounds of Examples 14, 16, 17, 18, 20, 56, 62, 79, 161, 162, 180, 181, 182, 208, 209, 213, 214, 215, 216, 217, 218, 219 or 220.

Compounds of formula I can be prepared by various methods well known to those skilled in the art. For example, compounds of formula I can be produced by processes known to those skilled in the art using either solution phase or solid phase synthesis as shown in the reaction schemes below.

Scheme 1:
Compounds of formula I(a)

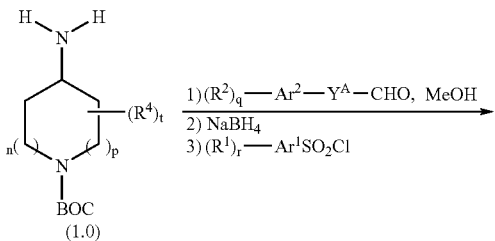

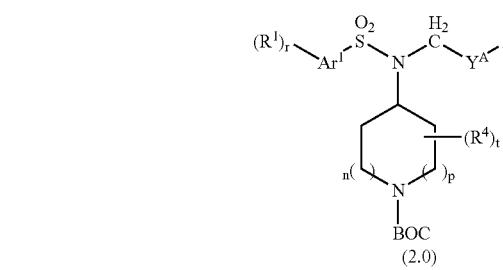

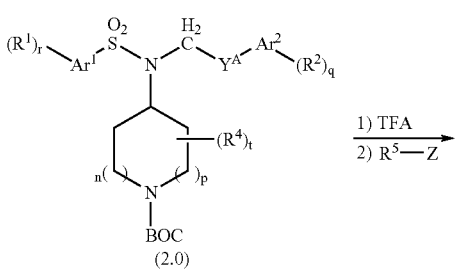

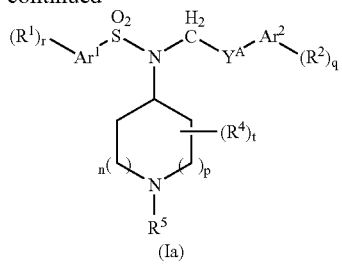

(Ia)

$Y^A$ represents a bond or —$(C(R^3)_2)_{1-2}$.

N-Boc mono-protected diamine 1.0 is treated with an aldehyde $(R^2)_q$—$Y^A$—$Ar^2CHO$, optionally in the presence of a dehydrating agent such as anhydrous magnesium sulfate or 4A molecular sieves. The resulting Schiff base is treated with a reducing agent such as sodium borohydride in an appropriate solvent such as methanol or ethanol, and the intermediate amine is reacted with arylsulfonyl chloride $(R^1)_r$—$Ar^1SO_2Cl$ in a solvent, such as dichloromethane, and in the presence of a base, such as triethylamine, to provide sulfonamide intermediate 2.0. This sulfonamide intermediate 2.0 is treated with an acid such as TFA to remove the Boc-protecting group. The resulting amine is further functionalized to introduce the group $R^5$ using standard methods known to those skilled in the art, such as via reductive amination with an appropriate aldehyde or ketone, nucleophilic displacement with an alkyl- or aralkyl-halide, amide formation with an acyl halide or acid, urea formation with an isocyanate or a suitable carbonyl chloride agent, or sulfonamidation to provide the expected N-aralkylsulfonamide Ia. For example Z can be a leaving group such as chloro, bromo, iodo, tosylate, mesylate, triflate, brosylate, or OH, or $R^5Z$ together may be an aldehyde, or $R^5$ may be terminated with an —NCO moiety.

Scheme 2:
Compounds of formula I(b)

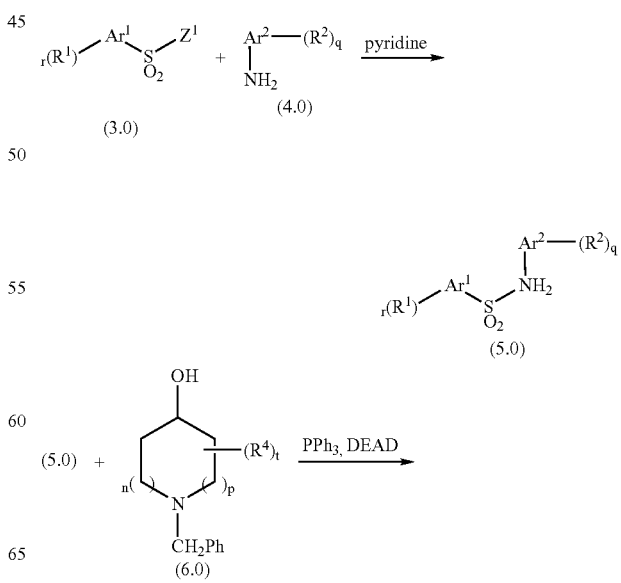

-continued

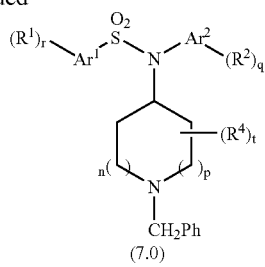

(7.0)

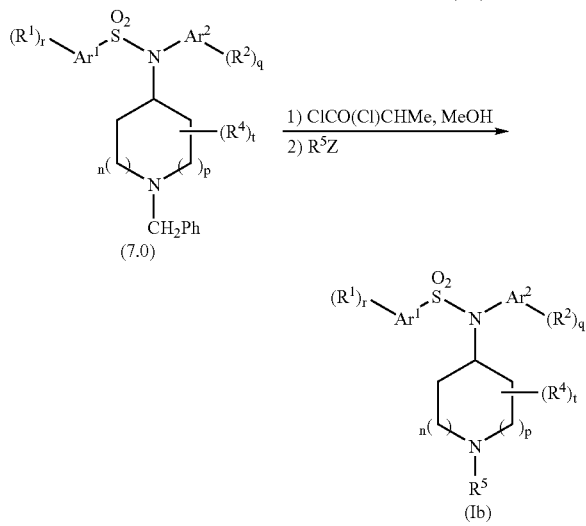

Reaction of arylsulfonyl halide $(R^1)_r$—$Ar^1SO_2Z^1$ (where Z=F, Cl or Br) with aniline $(R^2)_q$—$Ar^2NH_2$ in a solvent, such as pyridine, provides sulfonamide 5.0 which is subjected to Mitsunobu condensation with alcohol 6.0 to afford N-arylsulfonamide 7.0. The N-benzyl protecting group in intermediate 7.0 is then removed under standard conditions, such as with 1-chloroethyl chloroformate followed by methanol, and the resulting amine is further functionalized as for the end-synthesis of Ia (Scheme 1 above) to provide the expected N-arylsulfonamide Ib.

Alternative routes using other protecting groups than benzyl, such as, but not limited to, Boc, Fmoc or TBDMS may be apparent to those skilled in the art.

Certain compounds of this invention are prepared from other compounds of the invention using well-known functional group transformations such as ester hydrolysis, ester formation, amide formation, and reductive alkylation, examples of which are described in the preparations. Starting materials are prepared by known methods and/or methods described in the examples below.

Compounds of this invention are exemplified by the following examples, which should not be construed as limiting the scope of the disclosure. Alternative mechanistic pathways and analogous structures within the scope of the invention may be apparent to those skilled in the art.

In the following examples, "HRMS(MH$^+$)" refers to the measured high resolution mass of the compound. "LCMS (MH$^+$); Rt (min)" refers to the mass and retention time as determined by LC-Mass spectrum carried out on an Alltech Platinum C8 column (33 mm×7 mm ID, 3 micron particle size). Elution conditions for LC/MS are as follows: Solvents: A. Water w/0.05% TFA (v/v); B. Acetonitrile w/0.05% TFA (v/v); Flow Rate: 1 mL/min

| Gradient Method: | |
|---|---|
| Time (min) | % B Conc |
| 0 | 10 |
| 5 | 95 |
| 7 | 95 |
| 7.5 | 10 |
| 9 | STOP |

EXAMPLE 1

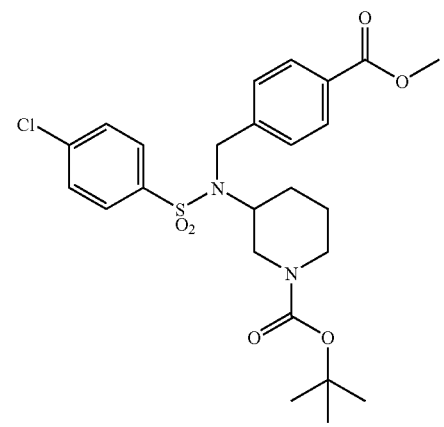

Step 1

A mixture of 3-amino-1-N-Boc-piperidine (3.00 g; 15.0 mmol), methyl 4-formylbenzoate (2.55 g; 15.5 mmol), Celite (3 g) and molecular sieves 4 Å (4 g) in anhydrous methanol was stirred at room temperature overnight. The reaction was treated with sodium borohydride (605 mg; 16.0 mmol) at 0° C., then stirred 3 h at room temperature. The final mixture was filtered, concentrated and the residue was taken up in 0.1 N aqueous NaOH solution and extracted with $CH_2Cl_2$. Combined organic layers were dried over $Na_2SO_4$, concentrated and the crude was purified by flash chromatography over silica gel (eluting Hexaries/AcOEt 1:1) to give 4.46 g (85%) of amine.

Step 2

A mixture of amine (3.00 g; 8.60 mmol) from Step 1, 4-chlorobenzenesulfonyl chloride (4.22 g; 20 mmol) and $Et_3N$ (3.50 ml; 25 mmol) in $CH_2Cl_2$ (30 ml) was stirred at room temperature for 2 days. The solution was washed with 0.1 N NaOH aqueous solution then 5% aqueous glacial citric acid solution, dried over $Na_2SO_4$, concentrated and purified on a plug of silica gel (eluting $CH_2Cl_2$/AcOEt 95:5) to afford 3.46 g (77%) of product Ia: $^1$H-NMR (300 MHz, CDCl$_3$) 8.01 (d, J=8.2 Hz, 2H), 7.77 (d, J=6.9 Hz, 2H), 7.49 (d, J=7.0 Hz, 2H), 7.43 (d, J=8.2 Hz, 2H), 4.43 (m, 2H), 3.85–4.05 (m, 2H), 3.93 (s, 3H), 3.69 (br s, 1H), 2.46 (t, 2H), 1.50–1.70 (m, 2H), 1.30–1.45 (m, 2H), 1.41 (s, 9H); LCMS (MH$^+$) 523.1, Rt=5.56 min.

Using procedures similar to those of Example 1, the compounds in Table 1 were prepared. In Table 1, "EX" represents "Example".

TABLE 1

| EX. | Structure | HRMS (MH+) | LCMS (MH+); Rt (min) |
|---|---|---|---|
| 2 | 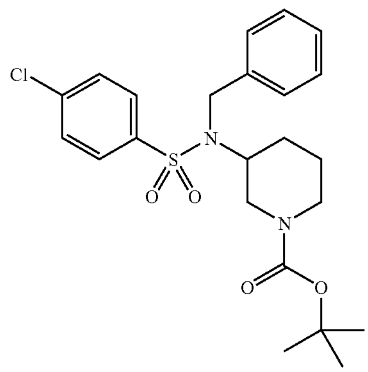 | 465.1614 | — |
| 3 | 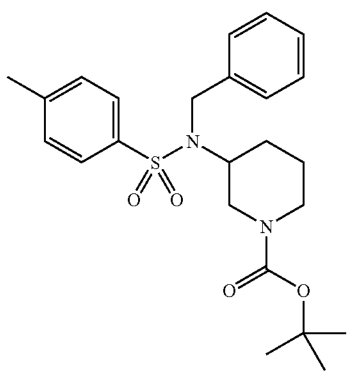 | 445.2160 | — |
| 4 | 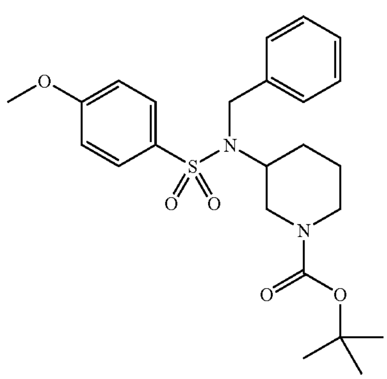 | — | 461.1; 5.46 |
| 5 | 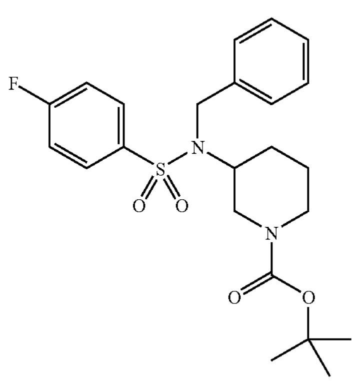 | — | 449.1; 5.46 |

TABLE 1-continued
| EX. | Structure | HRMS (MH⁺) | LCMS (MH⁺); Rt (min) |
|---|---|---|---|
| 6 | 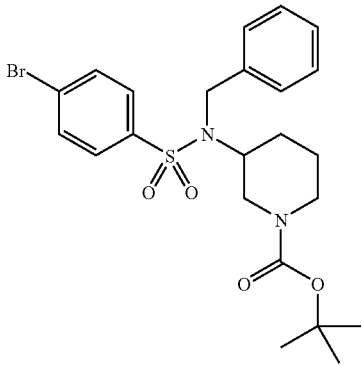 | — | 511.1; 5.71 |
| 7 | 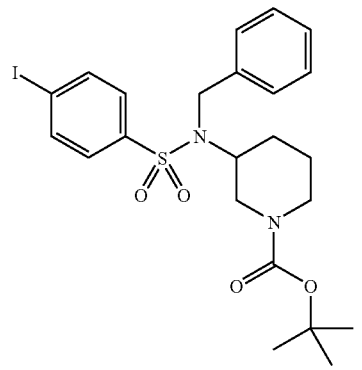 | — | 557.1; 5.81 |
| 8 | 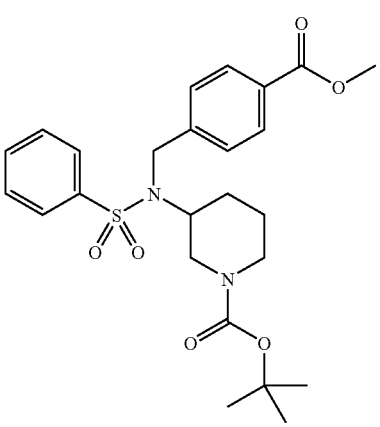 | 489.2064 | — |
| 9 | 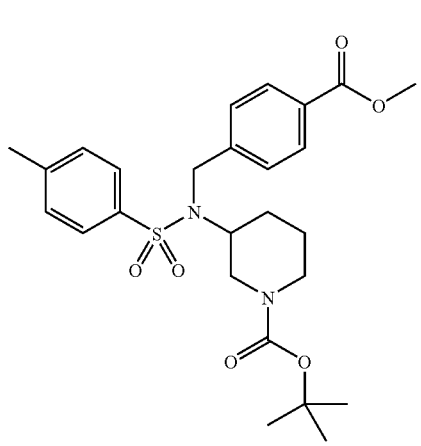 | 503.2214 | — |

TABLE 1-continued

| EX. | Structure | HRMS (MH+) | LCMS (MH+); Rt (min) |
|---|---|---|---|
| 10 | 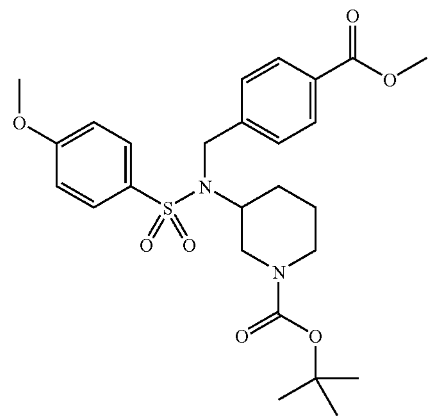 | 519.2173 | — |
| 11 | 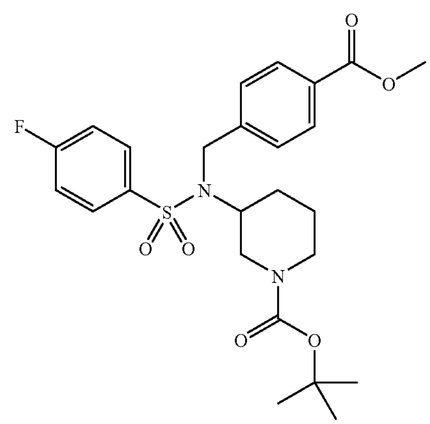 | 507.1974 | — |
| 12 | 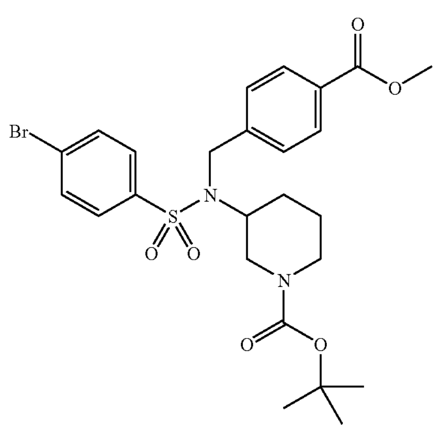 | 567.1161 | — |

TABLE 1-continued

| EX. | Structure | HRMS (MH⁺) | LCMS (MH⁺); Rt (min) |
|---|---|---|---|
| 13 | 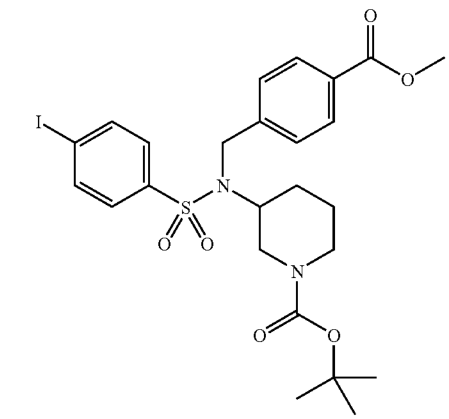 | — | 615.1; 5.71 |
| 14 | 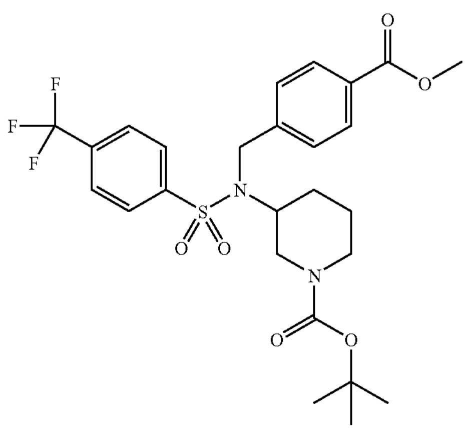 | 557.1945 | — |
| 15 | 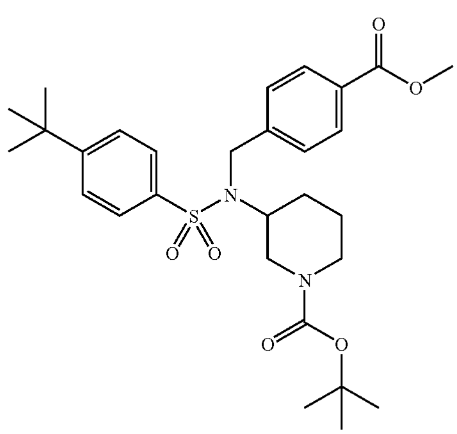 | — | 545.1; 5.86 |

TABLE 1-continued

| EX. | Structure | HRMS (MH+) | LCMS (MH+); Rt (min) |
|---|---|---|---|
| 16 | 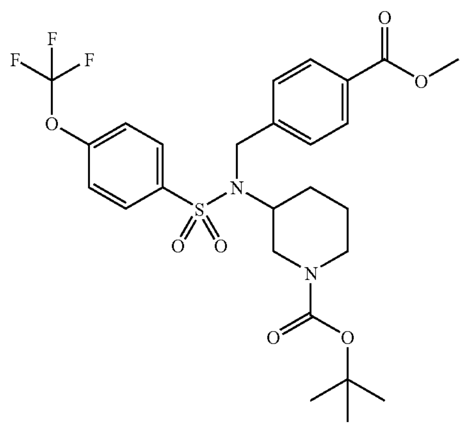 | 573.1886 | — |
| 17 | 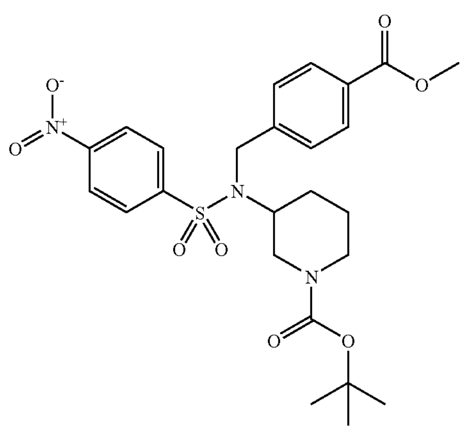 | 534.1909 | — |
| 18 | 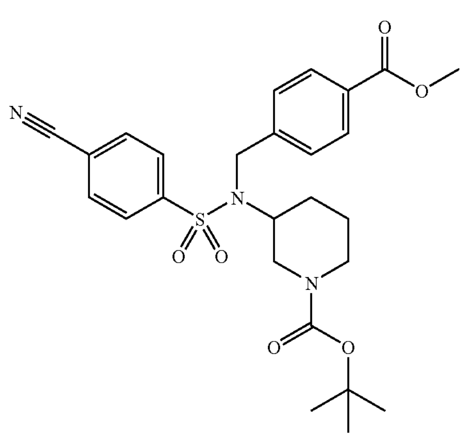 | 514.2018 | — |

TABLE 1-continued

| EX. | Structure | HRMS (MH+) | LCMS (MH+); Rt (min) |
|---|---|---|---|
| 19 | 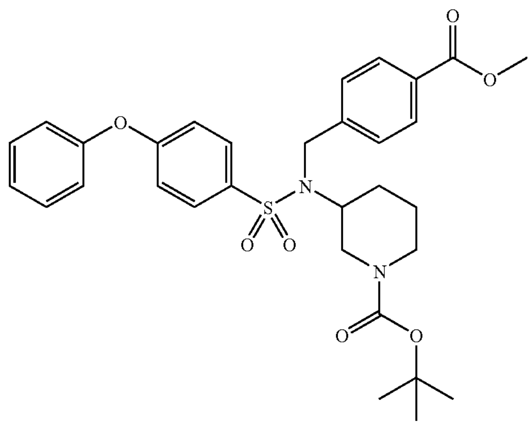 | — | 581.1; 5.81 |
| 20 | 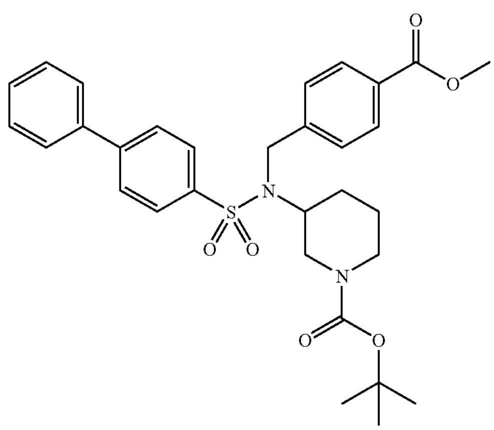 | 565.2364 | — |
| 21 | 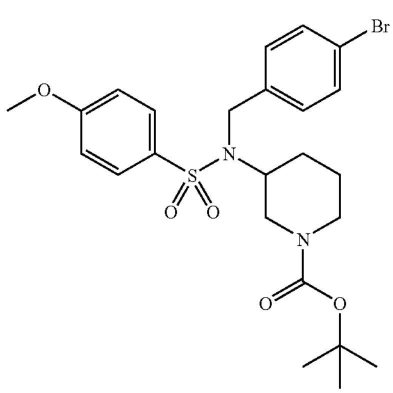 | — | 541.1; 5.66 |

TABLE 1-continued

| EX. | Structure | HRMS (MH⁺) | LCMS (MH⁺); Rt (min) |
|---|---|---|---|
| 22 | 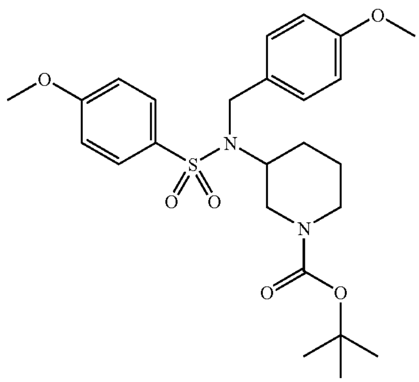 | — | 491.1; 5.41 |
| 23 | 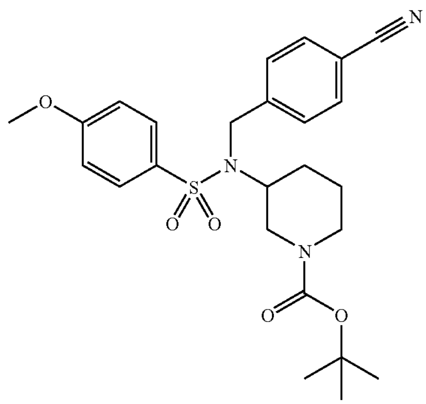 | — | 486.1; 5.26 |
| 24 | 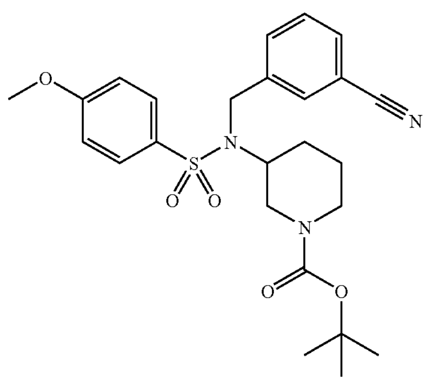 | — | 486.1; 5.26 |
| 25 | 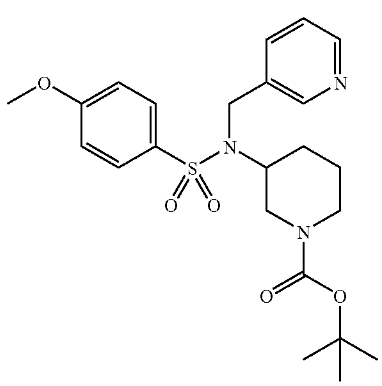 | — | 462.1; 4.31 |

TABLE 1-continued

| EX. | Structure | HRMS (MH+) | LCMS (MH+); Rt (min) |
|---|---|---|---|
| 26 | 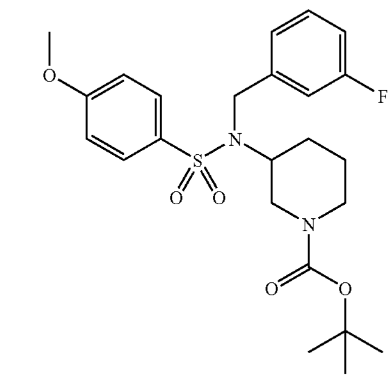 | — | 479.1; 5.41 |
| 27 | 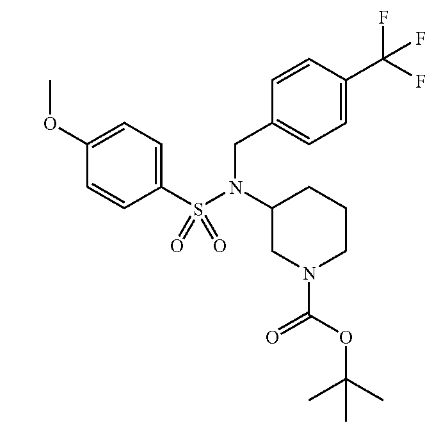 | — | 529.1; 5.56 |
| 28 | 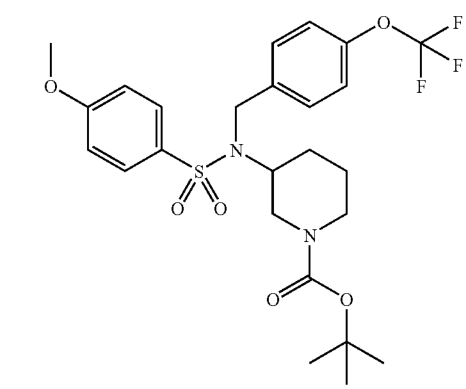 | — | 545.1; 5.66 |
| 29 | 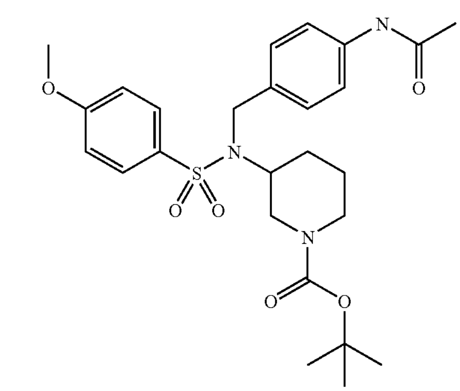 | — | 518.1; 4.91 |

TABLE 1-continued

| EX. | Structure | HRMS (MH+) | LCMS (MH+); Rt (min) |
|---|---|---|---|
| 30 | 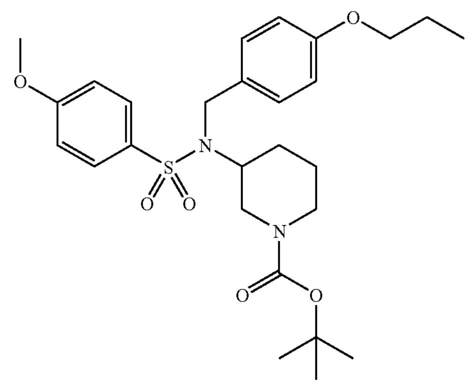 | — | 519.1; 5.71 |
| 31 | 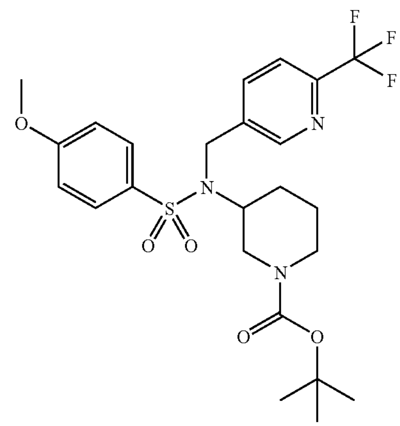 | — | 530.1; 5.26 |
| 32 | 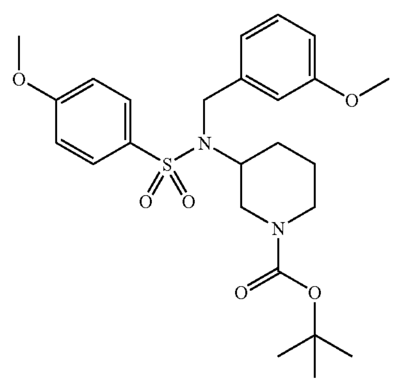 | — | 491.1; 5.36 |
| 33 | 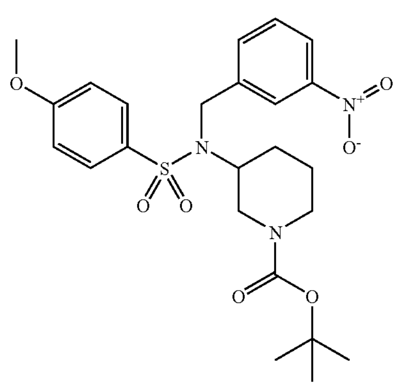 | — | 506.1; 5.36 |

TABLE 1-continued

| EX. | Structure | HRMS (MH⁺) | LCMS (MH⁺); Rt (min) |
|-----|-----------|------------|----------------------|
| 34 | 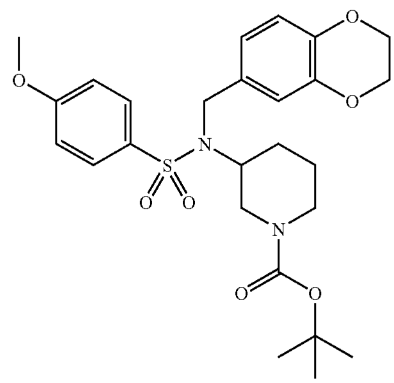 | — | 519.1; 5.36 |
| 35 | 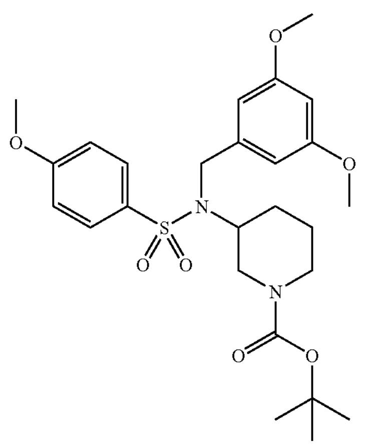 | — | 521.1; 5.41 |
| 36 | 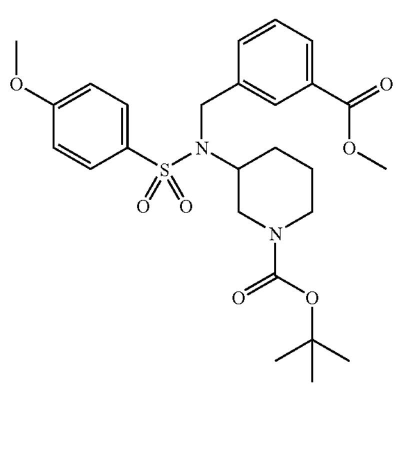 | 519.2173 | — |

TABLE 1-continued

| EX. | Structure | HRMS (MH⁺) | LCMS (MH⁺); Rt (min) |
|---|---|---|---|
| 37 | 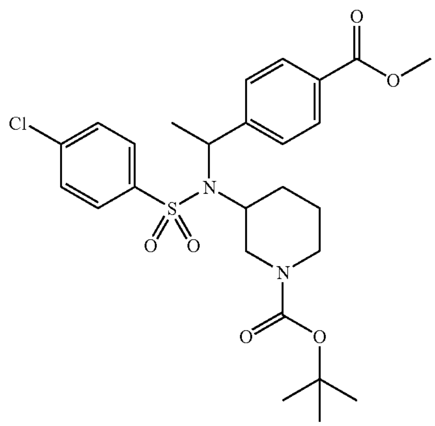 | — | 537.1; 5.66 |
| 38 | 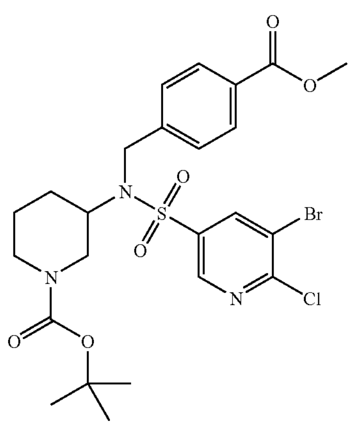 | 604.0712 | — |
| 39 | (Enantiomer A) | 557.1929 | — |

US 7,122,675 B2
37                                                                      38
TABLE 1-continued
| EX. | Structure | HRMS (MH+) | LCMS (MH+); Rt (min) |
|---|---|---|---|
| 40 | 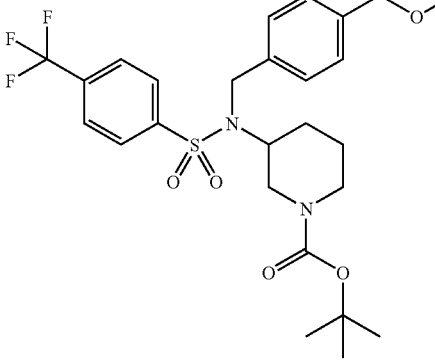 Enantiomer B | 557.1929 | — |
| 41 | 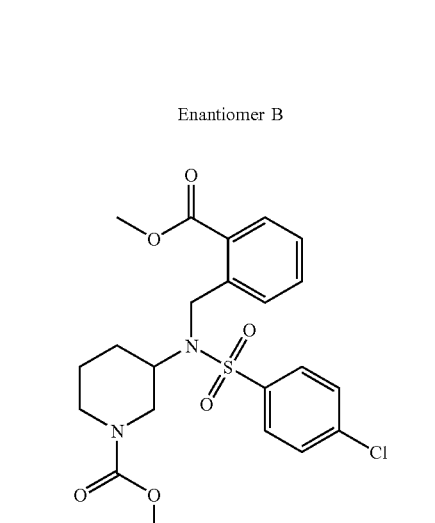 | 523.1668 | — |
| 42 | 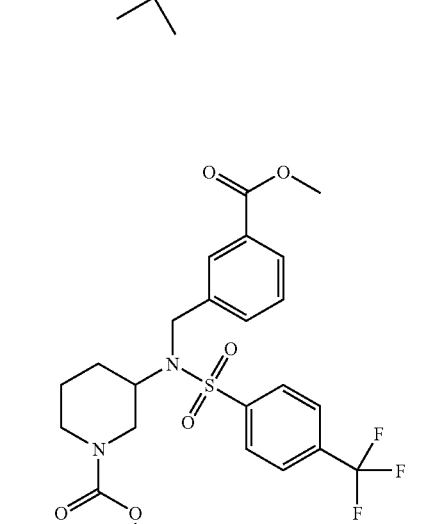 | 557.1934 | — |

TABLE 1-continued

| EX. | Structure | HRMS (MH+) | LCMS (MH+); Rt (min) |
|---|---|---|---|
| 43 | Diastereoisomer A | — | 521.1; 6.06 |
| 44 | Diastereoisomer B | — | 521.1; 6.01 |
| 45 | 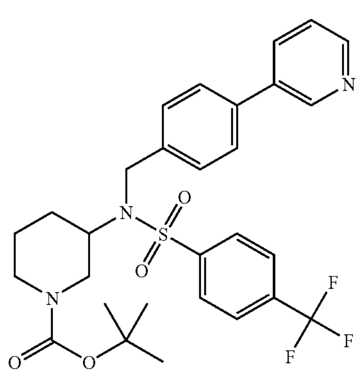 | 576.2137 | — |

TABLE 1-continued

| EX. | Structure | HRMS (MH+) | LCMS (MH+); Rt (min) |
|---|---|---|---|
| 46 | 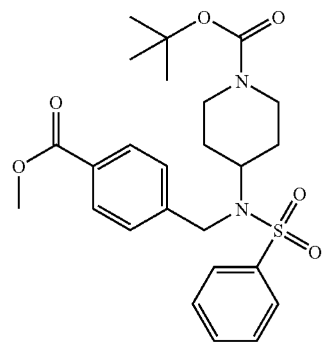 | — | 507.1; 5.26 |
| 47 | 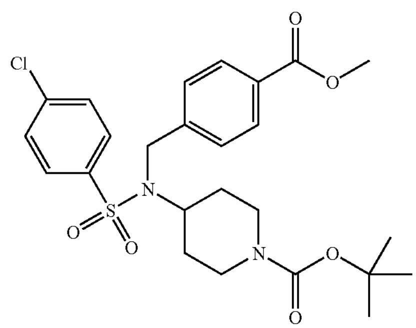 | — | 523.1 5.41 |
| 48 | 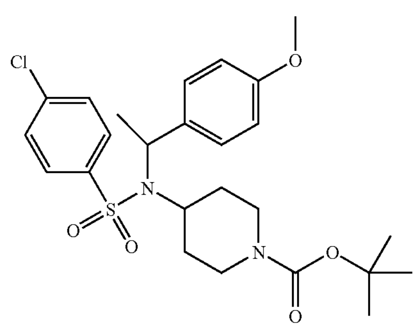 | — | 509.1 5.81 |
| 49 | 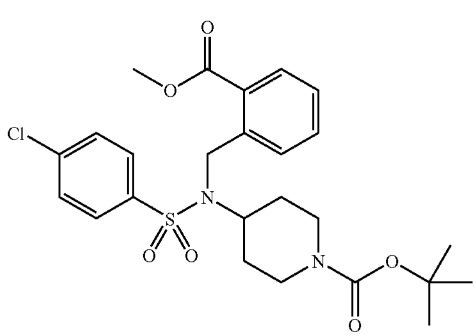 | — | 523.1 5.91 |

TABLE 1-continued

| EX. | Structure | HRMS (MH+) | LCMS (MH+); Rt (min) |
|---|---|---|---|
| 50 | 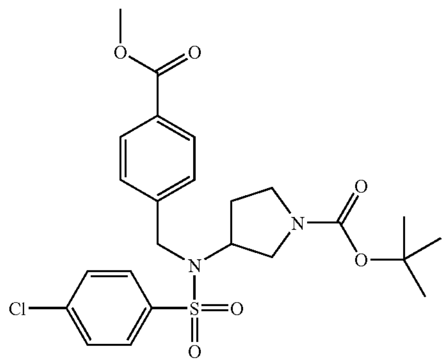 | — | 509.1; 5.31 |

EXAMPLE 51

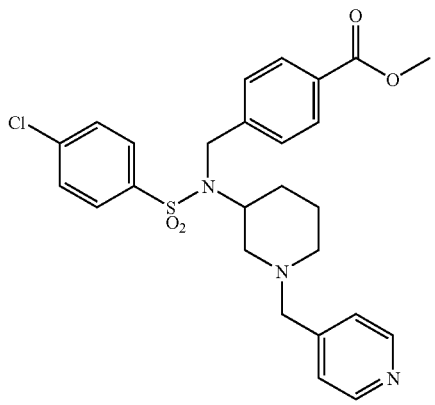

Step 1

A solution of the product of Example 1 Step 2 (1.0 g; 1.91 mmol) in CH$_2$Cl$_2$ and TFA was stirred at room temperature for 2 h then concentrated. The residue was treated with 1 N aqueous NaOH, extracted with CH$_2$Cl$_2$, dried over Na$_2$SO$_4$, and concentrated to provide 0.79 g (98%) of amine.

Step 2

A solution of amine from Step 1 (60 mg; 0.14 mmol), 4-pyridylcarboxaldehyde (42 L; 0.42 mmol) and molecular sieves 4 Å (100 mg) in DCE (2 mL) was stirred 45 min at room temperature followed by the addition of sodium triacetoxyborohydride (90 mg; 0.42 mmol). The reaction was stirred overnight at room temperature, quenched with MeOH (0.1 ml) for 10 min, and then diluted with 1 N aqueous NaOH. The solution was extracted with CH$_2$Cl$_2$, dried over Na$_2$SO$_4$, concentrated, and subjected to preparative chromatography over silica gel (eluting CH$_2$Cl$_2$/AcOEt 4:6). The final product was converted to the HCl salt by treatment with HCl in ether solution to give 38.4 mg of a white solid: $^1$H-NMR (free base, 300 MHz, CDCl$_3$) 8.51 (d, J=4.5 Hz, 2H), 7.99 (d, J=6.6 Hz, 2H), 7.69 (d, J=6.9 Hz, 2H), 7.30–7.45 (m, 4H), 7.10 (d, J=4.5 Hz, 2H), 4.43 (m, 2H), 3.85–4.00 (m, 1H), 3.93 (s, 3H), 3.33 (m, 2H), 2.64 (br d, 1H), 2.58 (br d, 1H), 1.60–1.75 (m, 2H), 1.45–1.60 (m, 3H), 1.10–1.30 (m, 1H); HRMS (MH+) 514.1563.

Using procedures similar to those of Example 51, compounds in Table 2 were prepared. In Table 2 "EX" represents "Example".

TABLE 2

| EX | Structure | HRMS (MH+) | LCMS (MH+); Rt (min) |
|---|---|---|---|
| 52 | 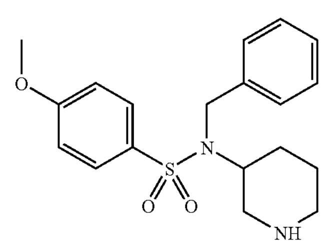 | — | 361.1; 4.06 |

TABLE 2-continued

| EX | Structure | HRMS (MH+) | LCMS (MH+); Rt (min) |
|---|---|---|---|
| 53 | 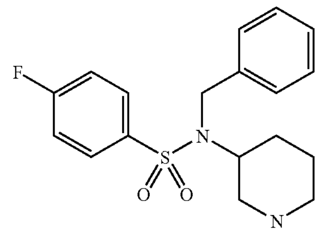 | — | 349.1; 4.06 |
| 54 | 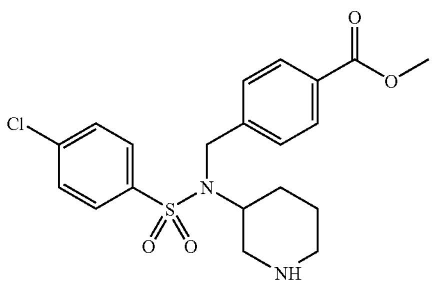 | — | 423.1; 4.36 |
| 55 | 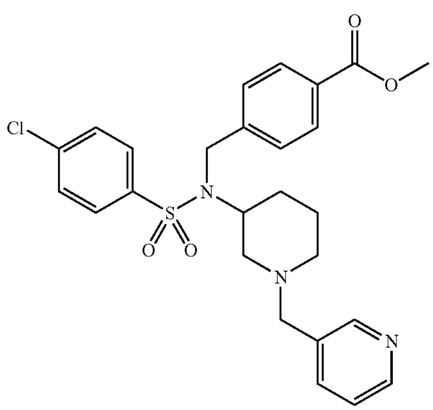 | 514.1558 | — |

EXAMPLE 56

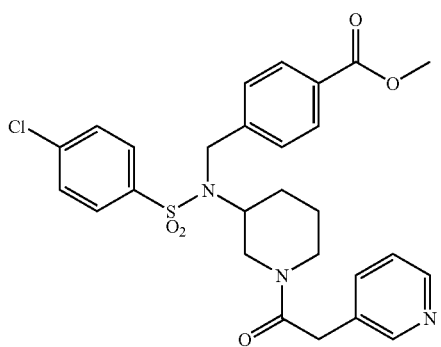

A solution of the amine from Example 51 Step 1 (50 mg; 0.12 mmol), 4-pyridylacetic acid hydrochloride (36 mg; 0.21 mmol), EDCI (40 mg; 0.21 mmol), HOBT (30 mg; 0.22 mmol) and N-methylmorpholine (70 l) in DMF (0.5 ml) was stirred at 45° C. overnight then concentrated. The residue was diluted in 0.1N aqueous NaOH, extracted with $CH_2Cl_2$, dried over $Na_2SO_4$, concentrated, and purified by preparative chromatography over silica gel (eluting $CH_2Cl_2$/AcOEt 4:6) to yield 31.4 mg of a foam: $^1$H-NMR (300 MHz, $CDCl_3$) 8.50 (br d, 1H), 8.41 (s, 1H), 7.90–8.05 (m, 2H), 7.70–7.80 (m, 2H), 7.35–7.60 (m, 5H), 7.23 (m, 1H), 4.24 and 4.72 (m, 1H), 4.35–4.55 (m, 2H), 3.90 (s, 3H), 3.50–3.90 (m, 4H), 2.57 and 2.71 (br t, 1H), 2.17 and 2.38 (br t, 1H), 1.20–1.75 (m, 4H); HRMS (MH+) 542.1505.

Using procedures similar to Example 56, the compounds in Table 3 were prepared. In Table 3 "EX" represents "Example".

TABLE 3

| EX | Structure | HRMS (MH+) | LCMS (MH+); Rt (min) |
|---|---|---|---|
| 57 | 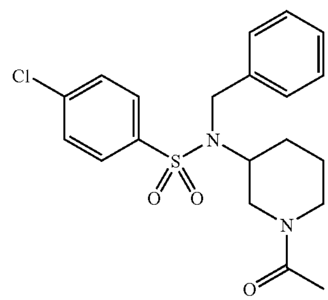 | — | 407.1; 4.96 |
| 58 | 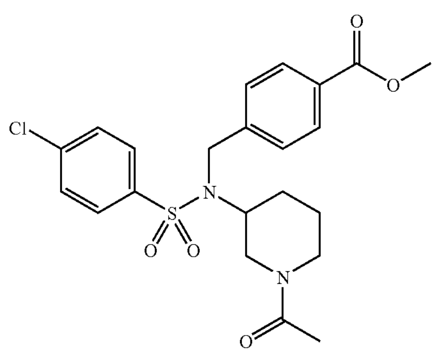 | — | 465.1; 4.96 |
| 59 | 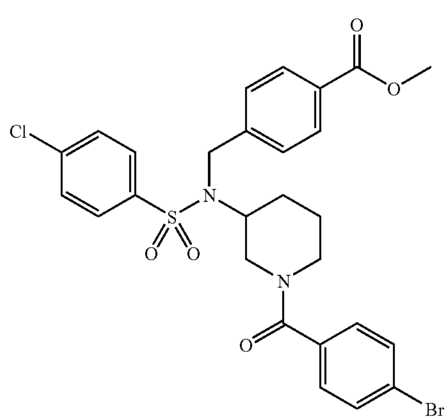 | — | 601.1; 5.51 |
| 60 | 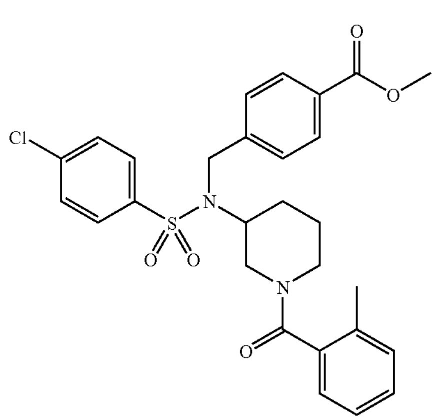 | — | 541.1; 5.21 |

TABLE 3-continued

| EX | Structure | HRMS (MH+) | LCMS (MH+); Rt (min) |
|---|---|---|---|
| 61 | 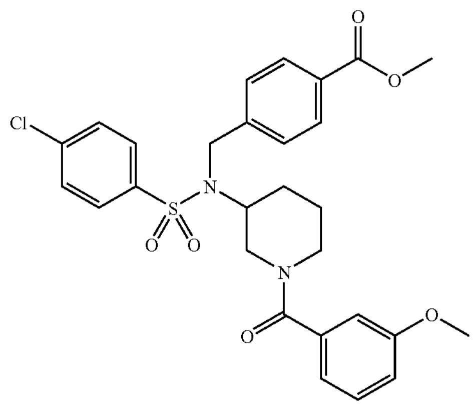 | — | 557.1; 5.16 |
| 62 | 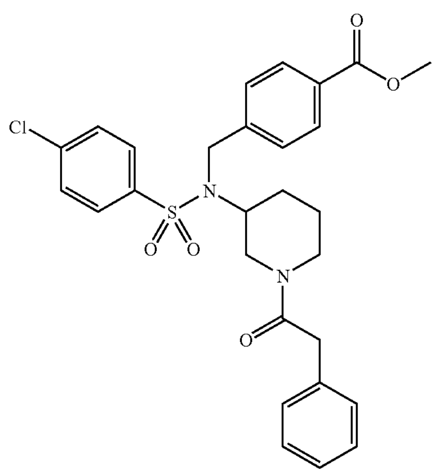 | — | 541.1; 5.21 |
| 63 | 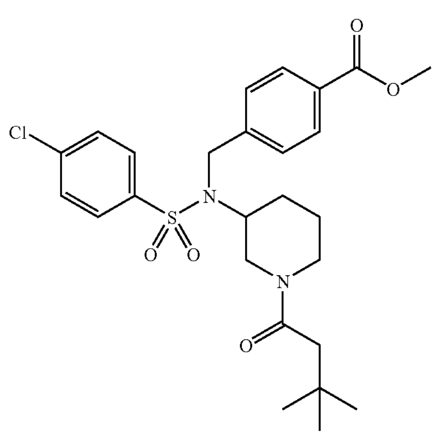 | — | 521.1; 5.31 |

TABLE 3-continued

| EX | Structure | HRMS (MH+) | LCMS (MH+); Rt (min) |
|----|-----------|------------|----------------------|
| 64 | 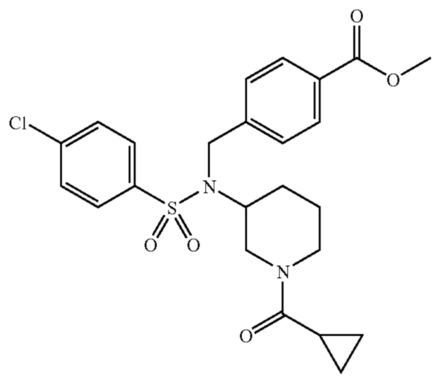 | — | 491.1; 5.06 |
| 65 | 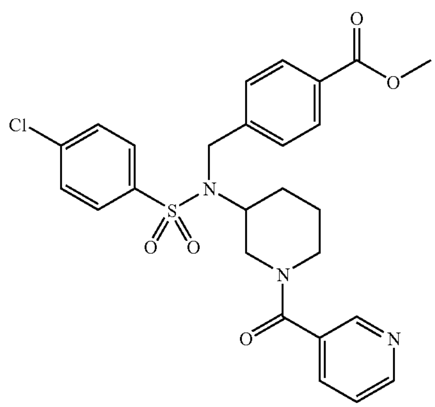 | 528.1354 | — |
| 66 | 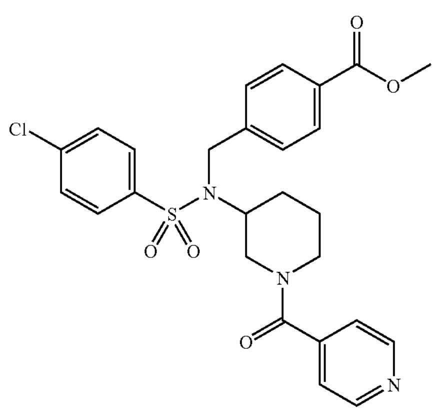 | 528.1357 | — |
| 67 | 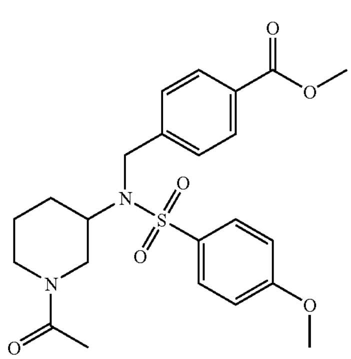 | 528.1357 | — |

TABLE 3-continued

| EX | Structure | HRMS (MH+) | LCMS (MH+); Rt (min) |
|---|---|---|---|
| 68 | 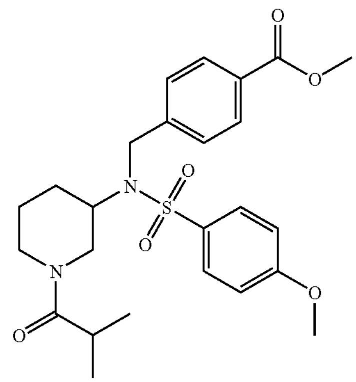 | — | 489.1; 5.16 |
| 69 | 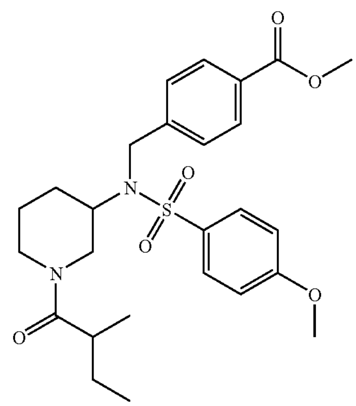 | — | 503.1; 5.26 |
| 70 | 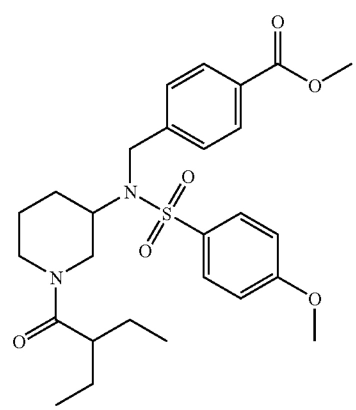 | — | 517.1; 5.36 |
| 71 | 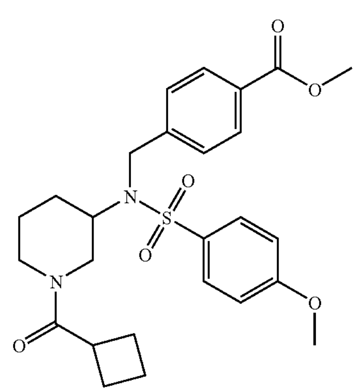 | — | 501.1; 5.26 |

TABLE 3-continued
| EX | Structure | HRMS (MH+) | LCMS (MH+); Rt (min) |
|---|---|---|---|
| 72 | 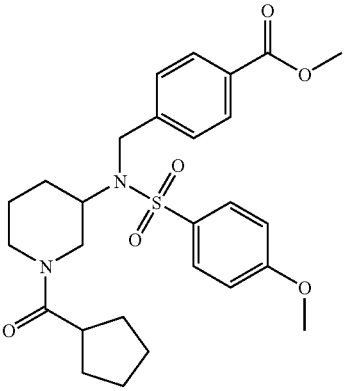 | — | 515.1; 5.41 |
| 73 | 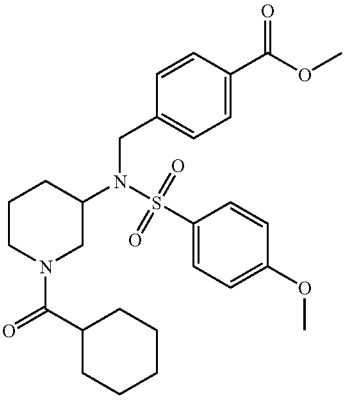 | — | 529.1; 5.51 |
| 74 | 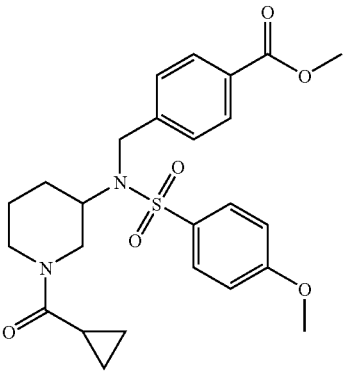 | 487.1894 | — |
| 75 | 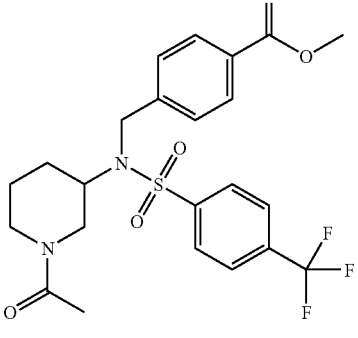 | 499.1518 | — |

TABLE 3-continued
| EX | Structure | HRMS (MH+) | LCMS (MH+); Rt (min) |
|---|---|---|---|
| 76 | 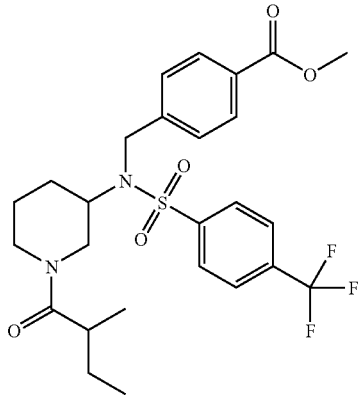 | 541.1991 | — |
| 77 | 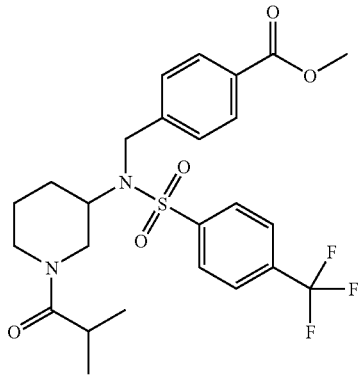 | 527.1825 | — |
| 78 | 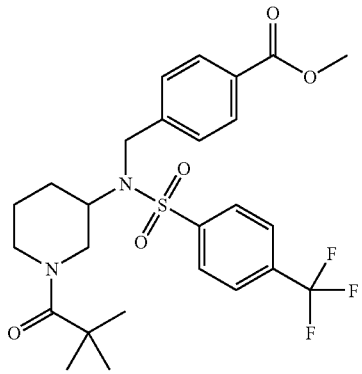 | 541.1991 | — |

TABLE 3-continued

| EX | Structure | HRMS (MH+) | LCMS (MH+); Rt (min) |
|---|---|---|---|
| 79 | 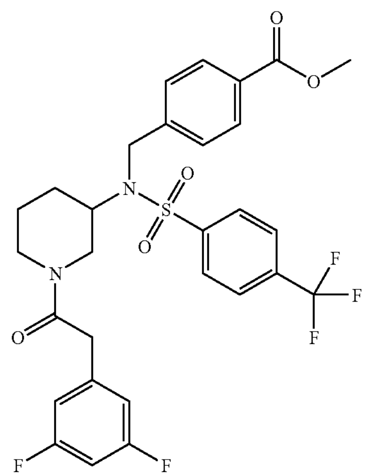 | 611.1634 | — |
| 80 | 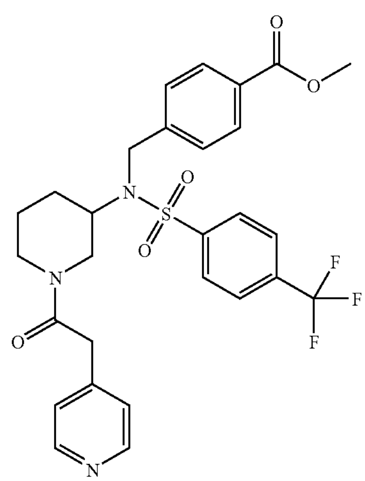 | 576.1786 | — |
| 81 | 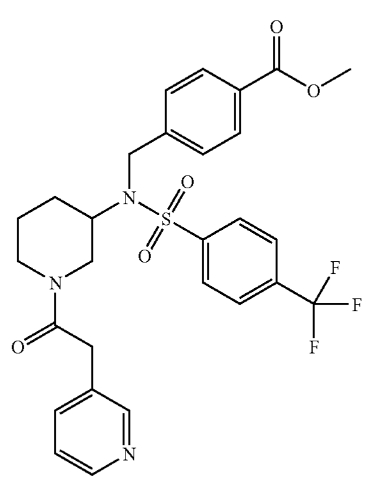 | 576.1786 | — |

TABLE 3-continued

| EX | Structure | HRMS (MH+) | LCMS (MH+); Rt (min) |
|---|---|---|---|
| 82 | 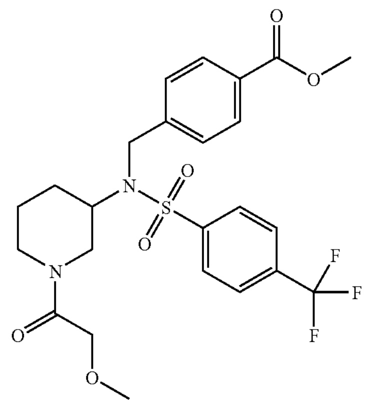 | 529.1619 | — |
| 83 | 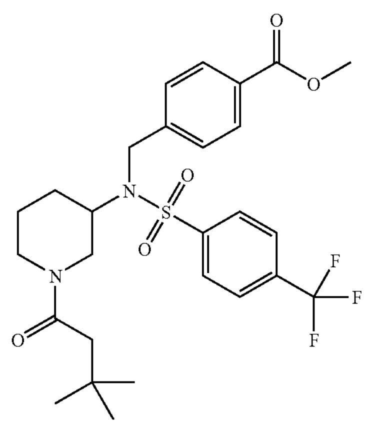 | 555.2150 | — |
| 84 | 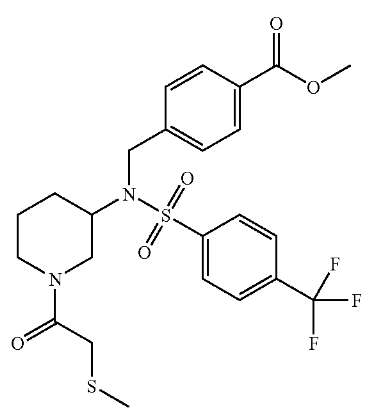 | 545.1405 | — |

TABLE 3-continued
| EX | Structure | HRMS (MH+) | LCMS (MH+); Rt (min) |
|---|---|---|---|
| 85 | 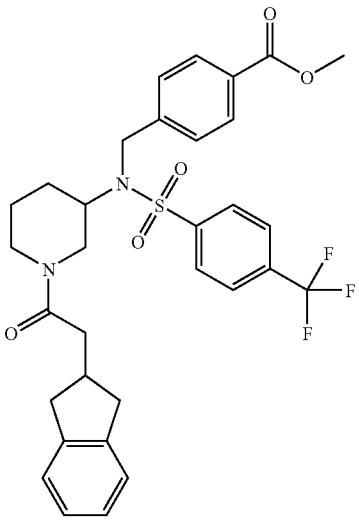 | 615.2130 | — |
| 86 | 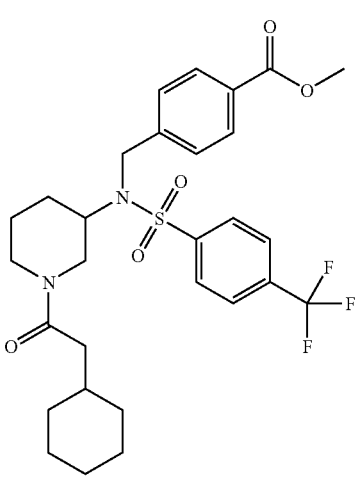 | — | 581.1; 5.86 |
| 87 | 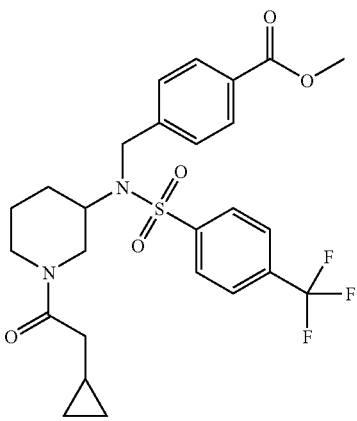 | 539.1836 | — |

TABLE 3-continued
| EX | Structure | HRMS (MH+) | LCMS (MH+); Rt (min) |
|---|---|---|---|
| 88 | 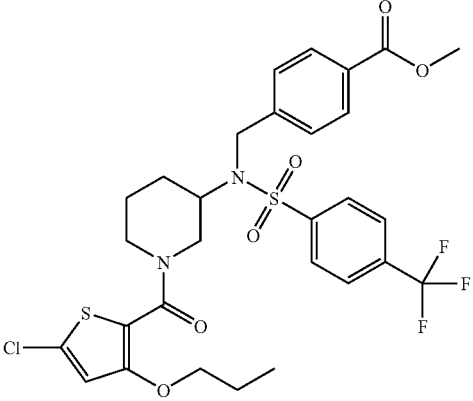 | 659.1273 | — |
| 89 | 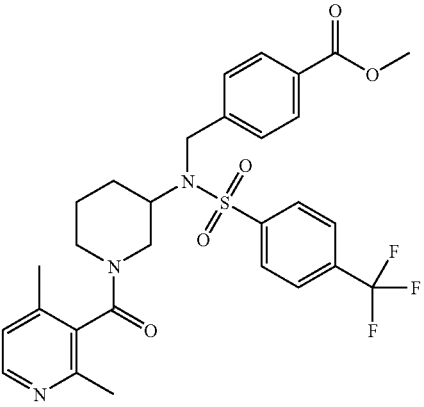 | 590.1941 | — |
| 90 | 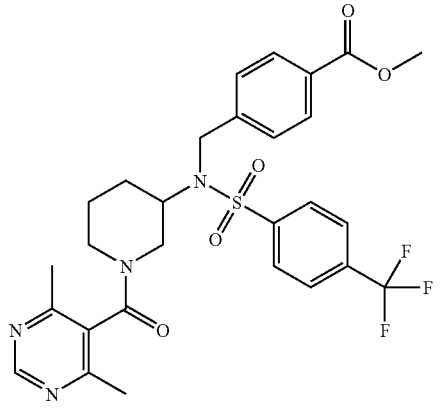 | 591.1899 | — |

TABLE 3-continued
| EX | Structure | HRMS (MH+) | LCMS (MH+); Rt (min) |
|----|-----------|------------|----------------------|
| 91 | 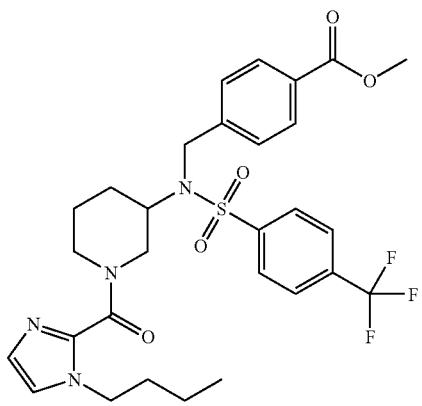 | 607.2195 | — |
| 92 | 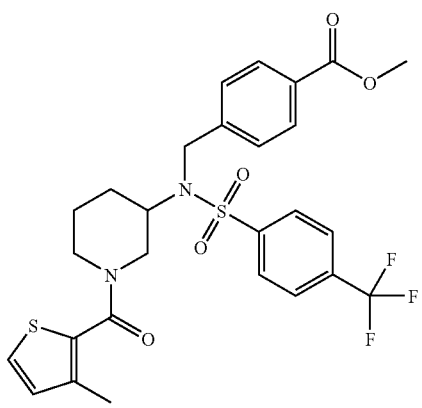 | 581.1399 | — |
| 93 | 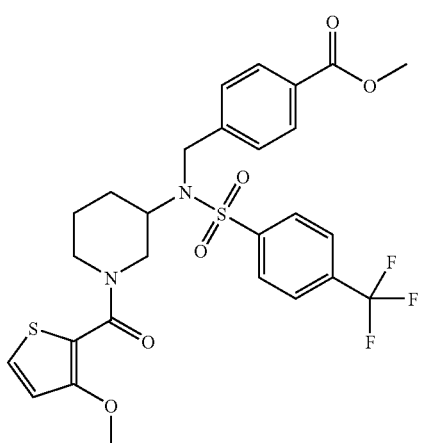 | 625.1643 | — |

EXAMPLE 94

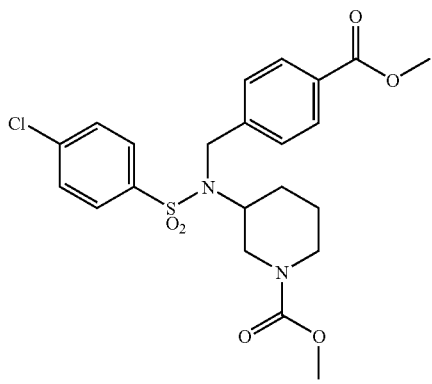

A solution of the amine from Example 51 Step 1 (50 mg; 0.12 mmol) in $CH_2Cl_2$ (0.5 ml) was treated with methyl chloroformate (12 l; 0.15 mmol) and triethylamine (24 mg; 0.24 mmol) and stirred and room temperature overnight. The reaction was diluted with 0.1N aqueous NaOH, extracted with $CH_2Cl_2$, dried over $Na_2SO_4$, concentrated, and purified by preparative chromatography over silica gel (eluting $CH_2Cl_2$/AcOEt 95:5) to yield 31.4 mg of a foam: $^1$H-NMR (300 MHz, $CDCl_3$) 8.01 (d, J=8.4 Hz, 2H), 7.80 (d, J=6.9 Hz, 2H), 7.51 (d, J=6.9 Hz, 2H), 7.44 (d, J=8.4 Hz, 2H), 4.45 (m, 2H), 3.65–4.05 (m, 3H), 3.93 (s, 3H), 3.64 (s, 3H), 2.46 (br t, 2H), 1.50–1.70 (m, 2H), 1.35–1.45 (m, 2H; LCMS $(MH^+)$ 481.1 Rt=5.11 min.

Using procedures similar to those of Example 94, the compounds in Table 4 were prepared. In Table 4 "EX" represents "Example".

TABLE 4

| EX | Structure | HRMS (MH+) | LCMS (MH+); Rt (min) |
|---|---|---|---|
| 95 | 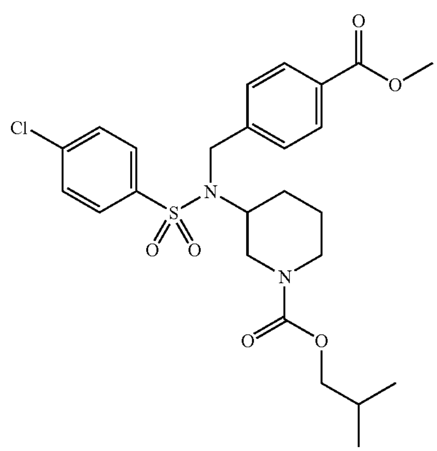 | 523.1678 | — |
| 96 | 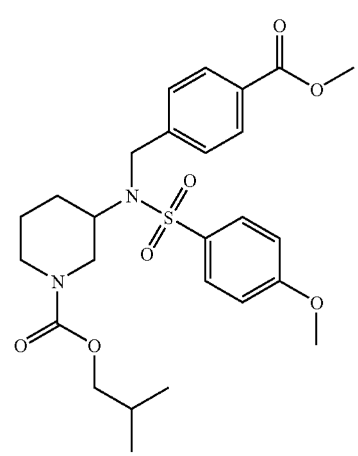 | — | 519.1; 5.66 |

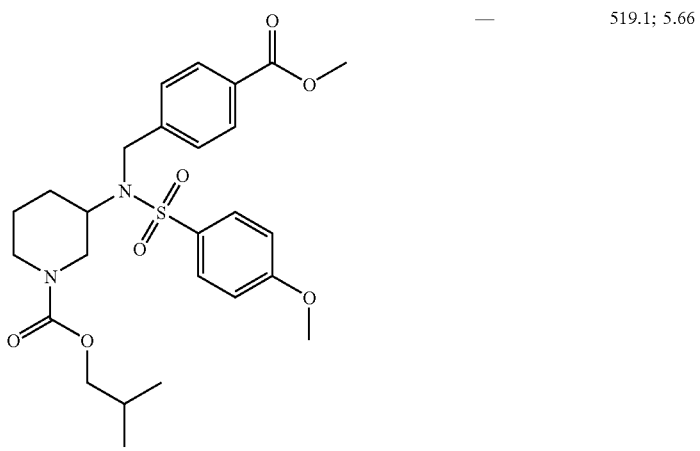

TABLE 4-continued

| EX | Structure | HRMS (MH+) | LCMS (MH+); Rt (min) |
|---|---|---|---|
| 97 | 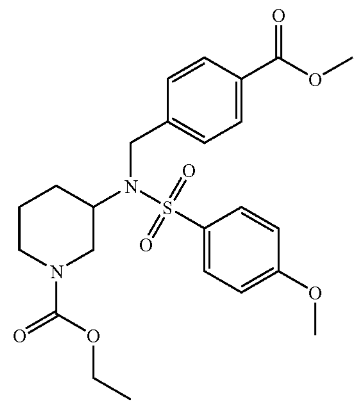 | — | 491.1; 5.31 |
| 98 | 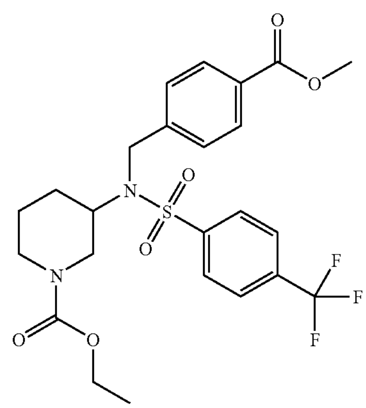 | 529.1619 | — |
| 99 | 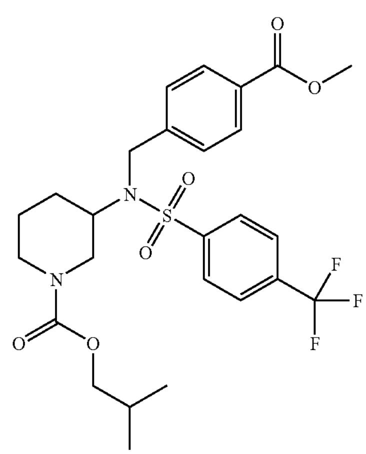 | 557.1929 | — |

TABLE 4-continued

| EX | Structure | HRMS (MH+) | LCMS (MH+); Rt (min) |
|---|---|---|---|
| 100 | 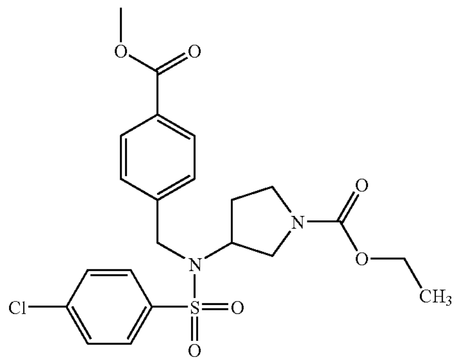 | — | 481.1; 5.26 |

EXAMPLE 101

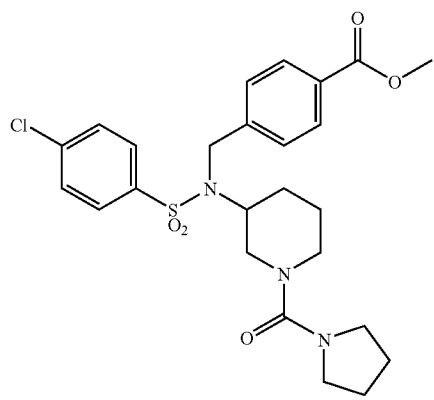

The experimental procedure described in Example 94 was applied on the amine from Example 51 Step 1 (50 mg; 0.12 mmol) but using 1-pyrrolidinecarbonyl chloride (18 l; 0.15 mmol) instead of methylchloroformate, to give 25.7 mg of an oil, after preparative chromatography over silica gel (eluting $CH_2Cl_2$/AcOEt 9:1): $^1$H-NMR (300 MHz, $CDCl_3$) 7.99 (d, J=8.4 Hz, 2H), 7.77 (d, J=6.9 Hz, 2H), 7.45–7.65 (m, 2H), 4.47 (m, 2H), 3.92 (s, 3H), 3.79 (m, 1H), 3.50–3.65 (m, 2H), 3.23 (m, 4H), 2.30–2.50 (m, 2H), 1.55–1.85 (m, 6H), 1.35–1.50 (m, 2H); HRMS (MH+) 520.1682.

Using procedures similar to those of Example 101, the compounds in Table 5 were prepared. In Table 5 "EX" represents "Example".

TABLE 5

| EX | Structure | HRMS (MH+) | LCMS (MH+); Rt (min) |
|---|---|---|---|
| 102 | 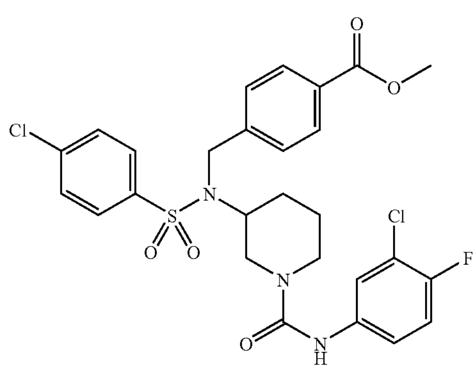 | — | 594.1; 5.46 |

TABLE 5-continued

| EX | Structure | HRMS (MH+) | LCMS (MH+); Rt (min) |
|---|---|---|---|
| 103 | 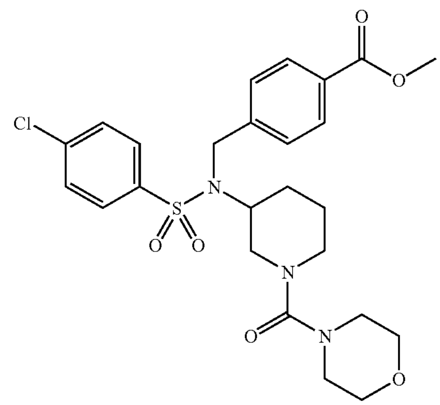 | — | 536.1; 4.91 |
| 104 | 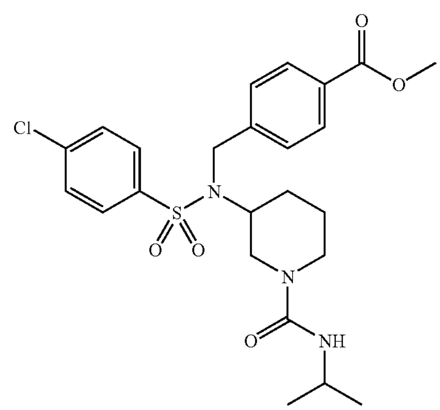 | — | 508.1; 5.01 |
| 105 | 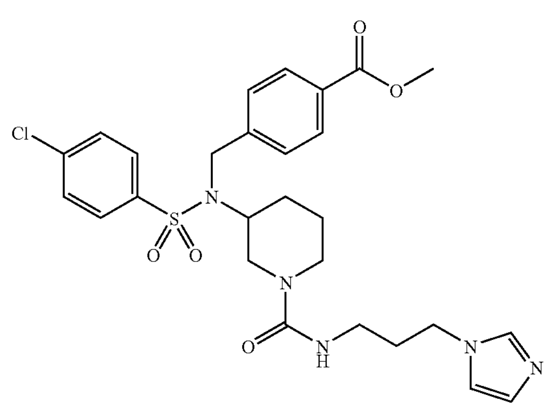 | — | 574.1; 4.21 |

TABLE 5-continued
| EX | Structure | HRMS (MH+) | LCMS (MH+); Rt (min) |
| --- | --- | --- | --- |
| 106 | 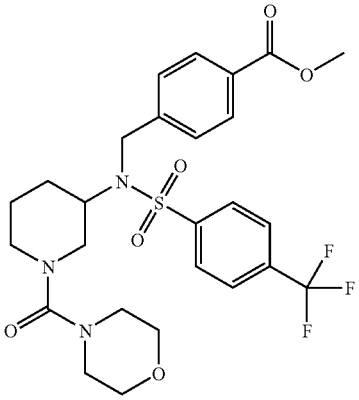 | 570.1884 | — |
| 107 | 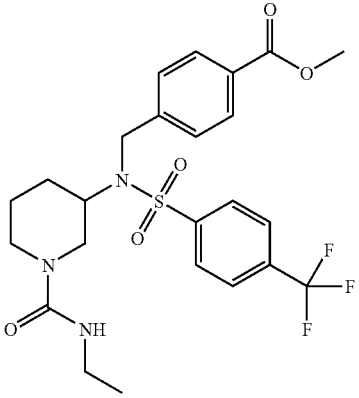 | 528.1781 | — |
| 108 | 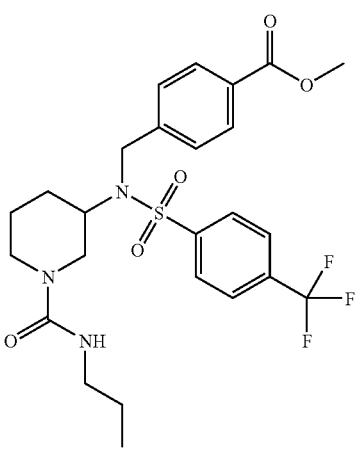 | 542.1939 | — |

TABLE 5-continued

| EX | Structure | HRMS (MH+) | LCMS (MH+); Rt (min) |
|---|---|---|---|
| 109 | 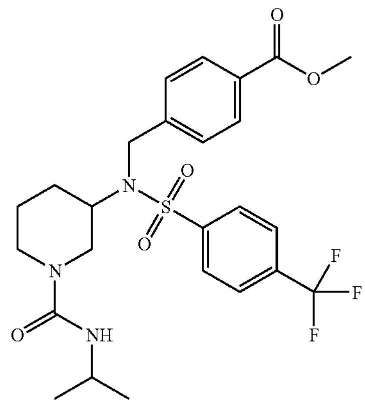 | 542.1939 | — |
| 110 | 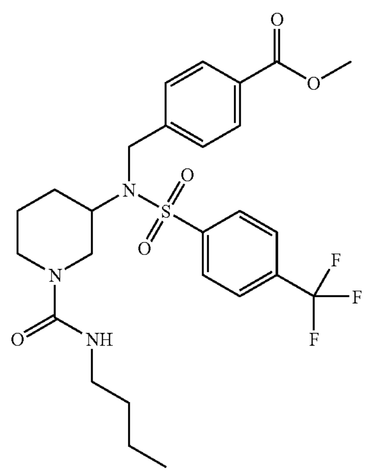 | 556.2098 | — |
| 111 | 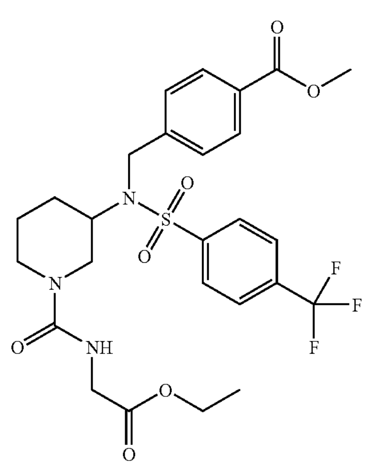 | 586.1844 | — |

TABLE 5-continued
| EX | Structure | HRMS (MH⁺) | LCMS (MH⁺); Rt (min) |
|---|---|---|---|
| 112 | 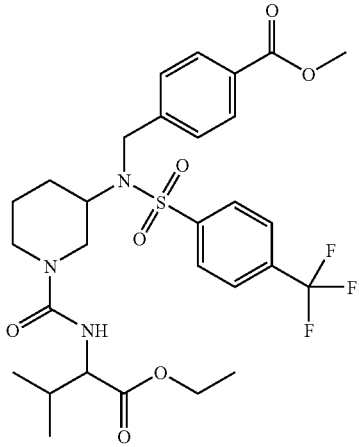 | 628.2300 | — |
| 113 | 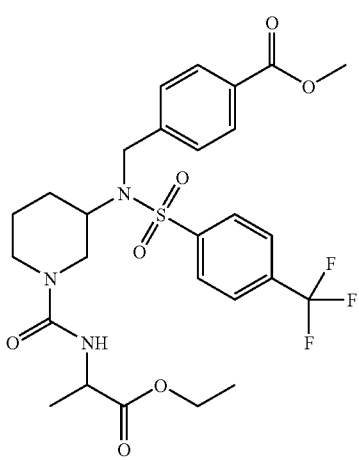 | 600.1985 | — |
| 114 | 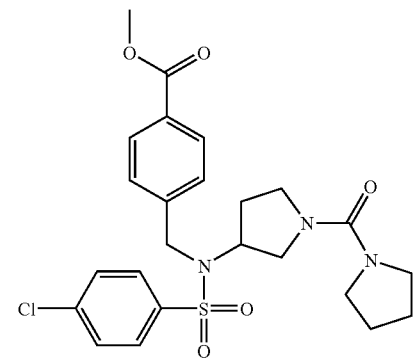 | — | 506.1; 5.16 |

TABLE 5-continued

| EX | Structure | HRMS (MH+) | LCMS (MH+); Rt (min) |
|---|---|---|---|
| 115 | 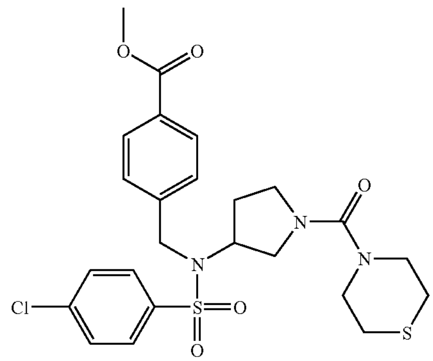 | — | 538.1; 5.41 |
| 116 | 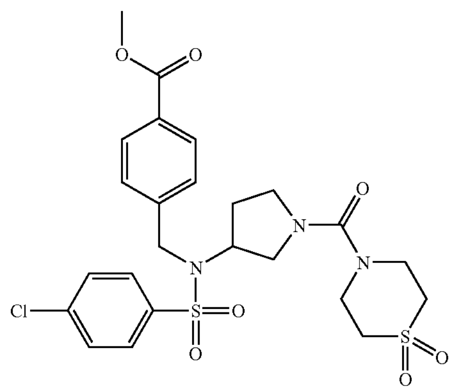 | — | 570.1; 4.91 |

EXAMPLE 117

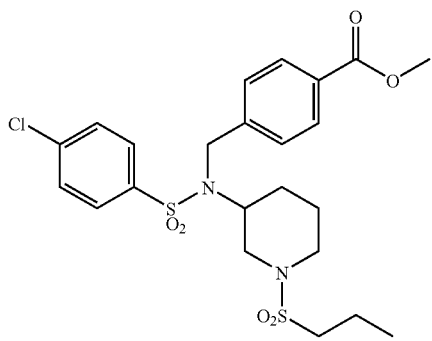

The experimental procedure described in Example 94 was applied on the amine from Example 51 Step 1 (50 mg; 0.12 mmol) but using n-propylsulfonyl chloride (30 l) instead of methylchloroformate, to give 15.3 mg of an oil, after preparative chromatography over silica gel (eluting $CH_2Cl_2$/AcOEt 95:5): $^1$H-NMR (300 MHz, $CDCl_3$) 8.01 (d, J=8.4 Hz, 2H), 7.80 (d, J=6.9 Hz, 2H), 7.51 (d, J=6.9 Hz, 2H), 7.42 (d, J=8.4 Hz, 2H), 4.46 (m, 2H), 3.93 (s, 3H), 3.80 (m, 1H), 3.55–3.70 (m, 2H), 2.75 (m, 2H), 2.40–2.60 (m, 2H), 1.65–1.80 (m, 3H), 1.40–1.65 (m, 3H); 1.00 (t, J=7.5 Hz, 2H); HRMS (MH+) 529.1227.

Using procedures similar to Example 117, the compounds in Table 6 were prepared. In Table 6 "EX" represents "Example".

TABLE 6
| EX | Structure | HRMS(MH⁺) | LCMS(MH⁺); Rt (min) |
|---|---|---|---|
| 118 | 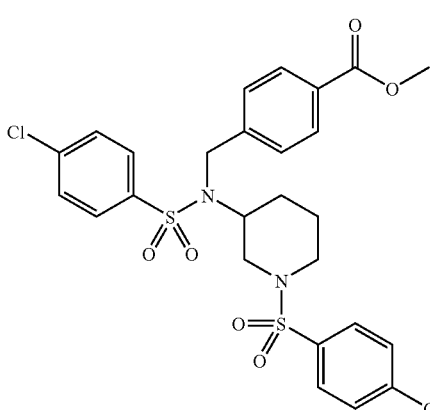 | — | 597.1; 5.61 |
| 119 | 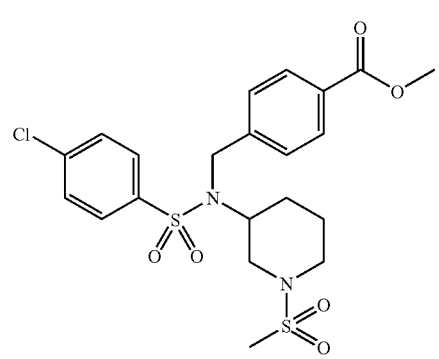 | 501.0926 | — |
| 120 | 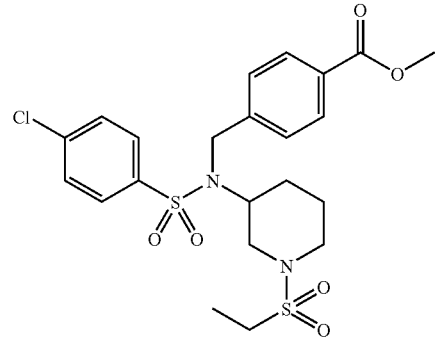 | — | 515.1; 5.01 |
| 121 | 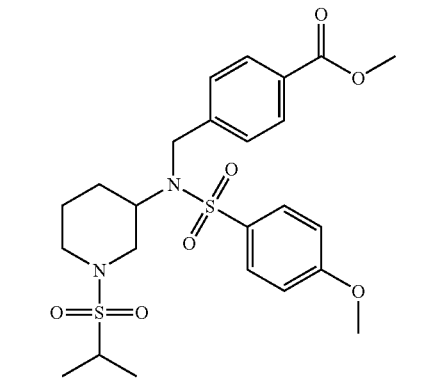 | — | 525.1; 5.26 |

TABLE 6-continued

| EX | Structure | HRMS(MH+) | LCMS(MH+); Rt (min) |
|---|---|---|---|
| 122 | 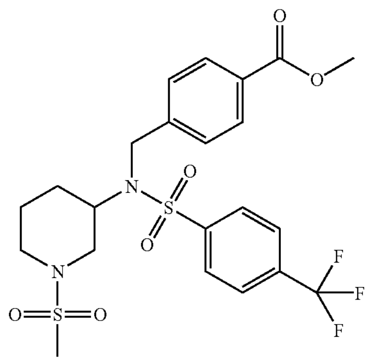 | 535.1183 | — |
| 123 | 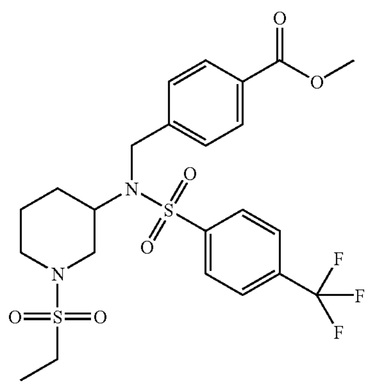 | 549.1342 | — |
| 124 | 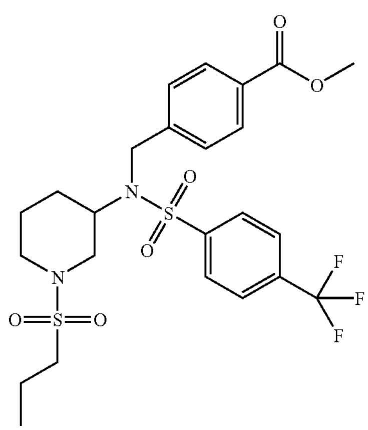 | 563.1495 | — |
| 125 | 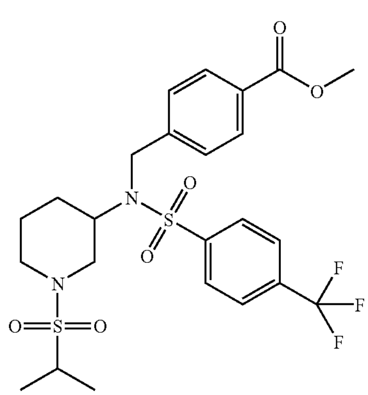 | 563.1495 | — |

TABLE 6-continued

| EX | Structure | HRMS(MH+) | LCMS(MH+); Rt (min) |
|---|---|---|---|
| 126 | 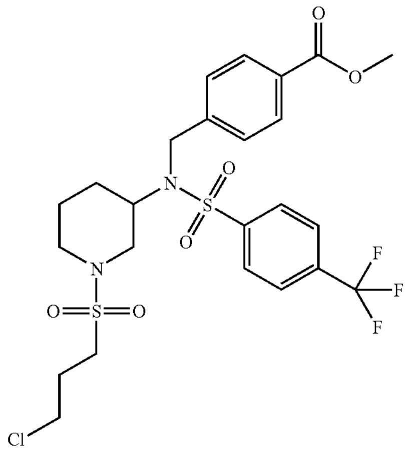 | 597.1102 | — |

EXAMPLE 127

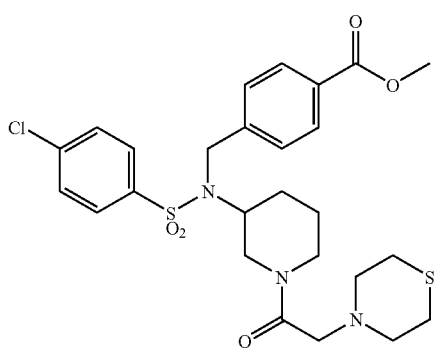

Step 1

To a solution of amine from Example 51 Step 1 (300 mg; 0.71 mmol) and potassium carbonate (290 mg; 2.1 mmol) in $CH_2Cl_2$ was added bromoacetyl chloride (71 l; 0.85 mmol) and the solution was stirred at room temperature overnight. The reaction mixture was washed with 0.1 N aqueous NaOH, dried over $Na_2SO_4$, concentrated, and purified on a plug of silica gel (eluting $CH_2Cl_2$/AcOEt 9:1) to yield 281 mg (73%) of bromoacetamide.

Step 2

A solution of bromoacetamide (60 mg) from Step 1 and thiomorpholine (100 l) was stirred in DCE at 40° C. overnight then concentrated. The residue was diluted in 0.1N aqueous NaOH, extracted with $CH_2Cl_2$, dried over $Na_2SO_4$, concentrated, and purified by preparative chromatography over silica gel (eluting $CH_2Cl_2$/AcOEt 4:6) to yield 13.3 mg of an oil: $^1$H-NMR (300 MHz, $CDCl_3$) 7.95–8.10 (m, 2H), 7.70–7.85 (m, 2H), 7.40–7.55 (m, 4H), 4.25 and 4.72 (m, 1H), 4.30–4.50 (m, 2H), 3.93 (s, 3H), 3.85–4.03 (m, 1H), 3.50–3.90 (m, 2H), 2.95–3.20 (m, 2H), 2.05–2.80 (m, 10 H), 1.25–1.80 (m, 4H); LRMS (MH+) 566.1; Rt=4.41 min.

Using procedures similar to those of Example 127, the compounds in Table 7 were prepared. In Table 7 "EX" represents "Example".

TABLE 7

| EX | Structure | HRMS (MH+) | LCMS (MH+); Rt (min) |
|---|---|---|---|
| 128 | 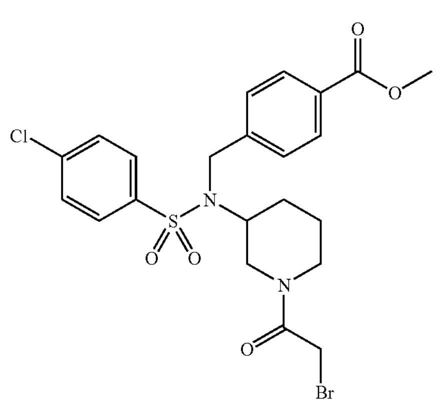 | 543.0334 | — |

TABLE 7-continued

| EX | Structure | HRMS (MH+) | LCMS (MH+); Rt (min) |
|---|---|---|---|
| 129 | 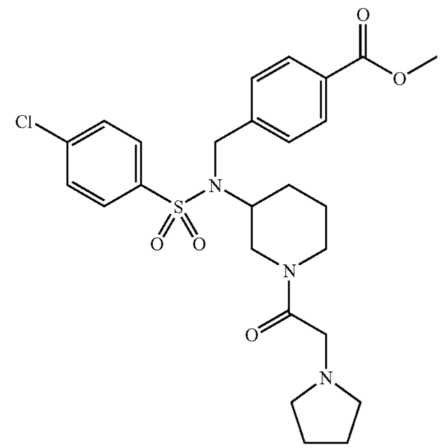 | 534.1821 | — |

EXAMPLE 130

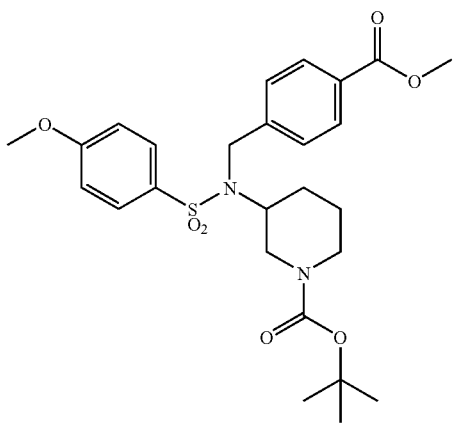

Step 1

A solution of methyl ester prepared as in Example 1 (5.0 g; 9.6 mmol) was treated with 1N aqueous NaOH (20 ml) in EtOH (40 ml). The reaction was stirred at 50° C. for 2 h, EtOH was evaporated and the mixture was acidified with 5% aqueous glacial citric acid and extracted with $CH_2Cl_2$ and AcOEt. Combined organic layers were dried over $Na_2SO_4$ and concentrated to give 5.0 g of acid.

Step 2

A solution of acid (60 mg; 0.12 mmol), ethanol (35 L; 0.6 mmol)), EDCI 935 mg; 0.18 mmol) and DMAP (5 mg) in $CH_2Cl_2$ was stirred at room temperature overnight. The reaction was concentrated and directly purified by preparative chromatography over silica gel (eluting Hexanes/AcOEt 1:1) to yield 45.3 mg of an oil: $^1$H-NHR (300 MHz, $CDCl_3$) 8.00 (d, J=8.4 Hz, 2H), 7.77 (d, J=8.8 Hz, 2H), 7.43 (d, J=8.4 Hz, 2H), 6.97 (d, J=8.4 Hz, 2H), 4.30–4.55 (m, 2H), 4.37 (q, J=7.2 Hz, 2H), 3.85–4.00 (m, 2H), 3.87 (s, 3H), 3.65 (br s, 1H), 2.25–2.50 (m, 2H), 1.50–1.75 (m, 2H), 1.30–1.50 (m, 5H), 1.39 (s, 9H); HRMS (MH+) 533.2330.

Using procedures similar to those of Example 130, the compounds in Table 8 were prepared. In Table 8 "EX" represents "Example".

TABLE 8

| EX | Structure | HRMS (MH+) | LCMS (MH+); Rt (min) |
|---|---|---|---|
| 131 | 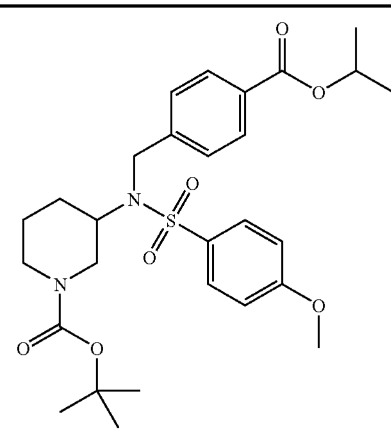 | 547.2470 | — |

TABLE 8-continued

| EX | Structure | HRMS (MH+) | LCMS (MH+); Rt (min) |
|---|---|---|---|
| 132 | 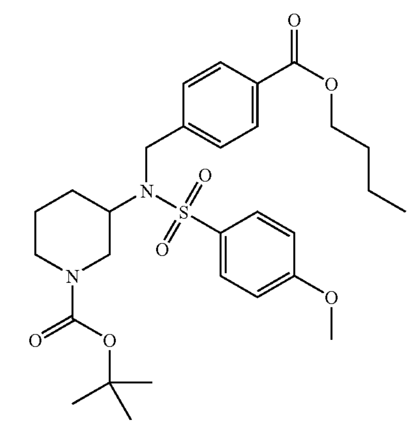 | 561.2628 | — |
| 133 | 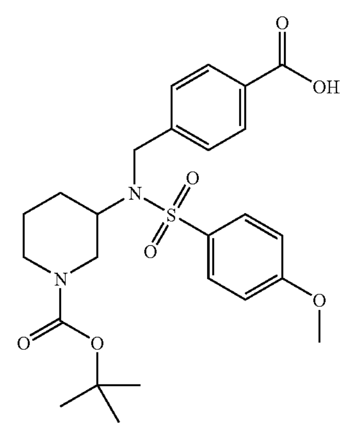 | 505.2009 | — |

EXAMPLE 134

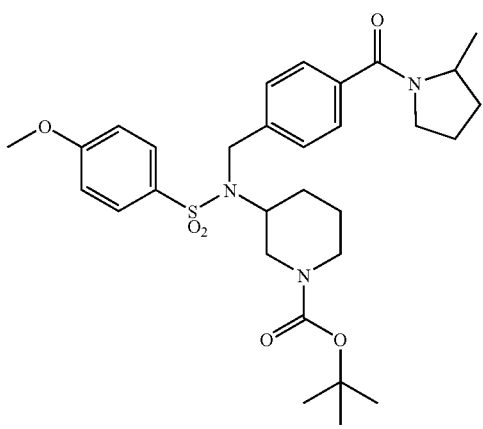

A solution of the acid from Example 130 Step 1 (50 mg; 0.10 mmol), 2-methyl-pyrrolidine (14 μl; 0.13 mmol), PS-Carbodiimide (Argonaut Technologies) resin (0.35 g; 0.85 mmol/g loading) and HOBT (20 mg; 0.15 mmol) in $CH_2Cl_2$ (2 ml) was shaken overnight. The slurry was treated with an excess of PS-trisamine (Argonaut Technologies) and N-Methylisatoic anhydride polystyrene (NovaBiochem) in equal proportion, diluted with $CH_2Cl_2$ and shaken another 3 h. Filtration and concentration of the solvent provided 27 mg of an oil: LRMS (MH+) 572.1.

Using procedures similar to those of Example 134, the compounds in Table 9 were prepared. In Table 9 "EX" represents "Example".

TABLE 9

| EX | Structure | HRMS (MH+) | LCMS (MH+); Rt (min) |
|---|---|---|---|
| 135 | 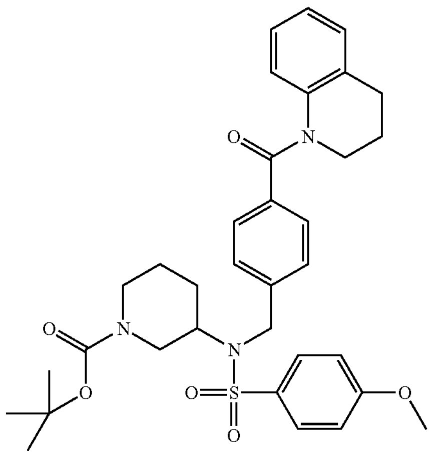 | — | 620.1; 5.56 |
| 136 | 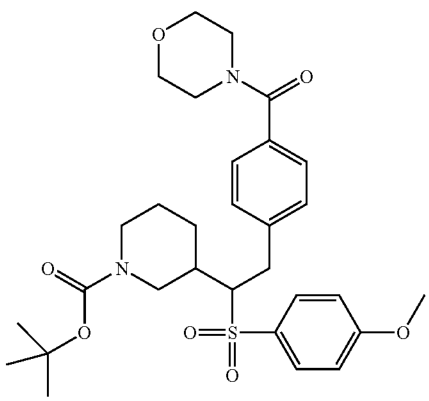 | — | 574.1; 4.91 |
| 137 | 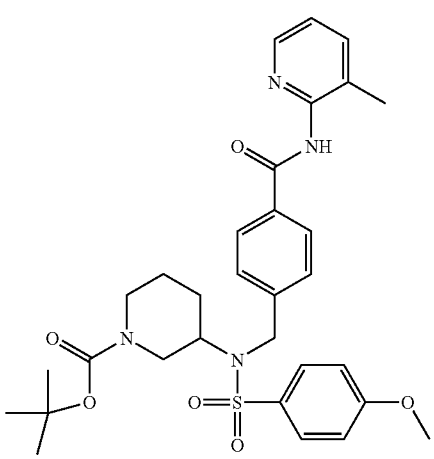 | — | 595.1; 5.21 |

TABLE 9-continued

| EX | Structure | HRMS (MH+) | LCMS (MH+); Rt (min) |
|---|---|---|---|
| 138 | 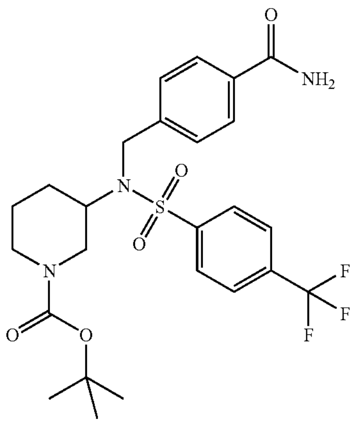 | 542.1939 | — |
| 139 | 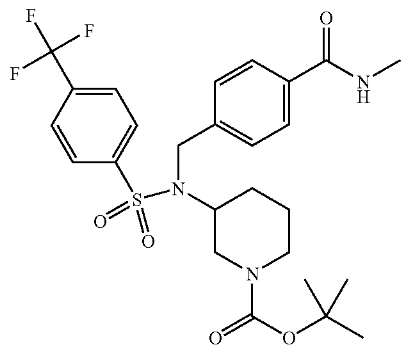 | — | 556.1; 5.26 |

EXAMPLE 140

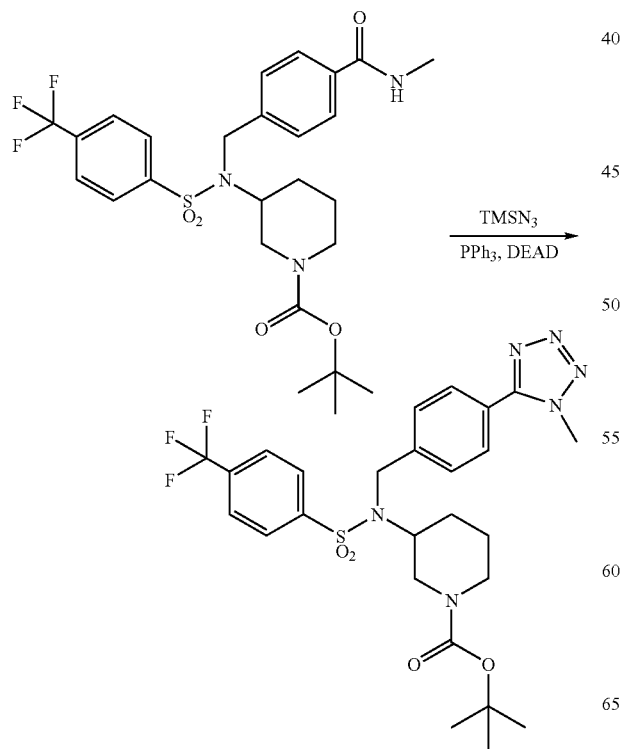

To a solution of the product of Example 139 (100 mg; 0.18 mmol), PPh$_3$ (71 mg; 0.27 mmol) and trimethylsilyl azide (36 l; 0.27 mmol) in THF (20 ml) was added DEAD (43 l; 0.27 mmol) and the reaction was stirred 2 days at room temperature. The solution was diluted with brine, extracted with CH$_2$Cl$_2$, dried over Na$_2$SO$_4$, concentrated, and purified by preparative chromatography over silica gel (eluting CH$_2$Cl$_2$/AcOEt 7:3) to afford 7.7 mg of an oil: $^1$H-NMR (300 MHz, CDCl$_3$) δ 8.00 (d, J=8.4 Hz, 2H), 7.81 (d, J=8.4 Hz, 2H), 7.75 (d, J=8.1 Hz, 2H), 7.60 (d, J=8.1 Hz, 2H), 4.52 (m, 2H), 4.20 (s, 3H), 3.90–4.05 (m, 2H), 3.78 (br s, 1H), 2.30–2.55 (m, 2H), 1.35–1.75 (m, 4H), 1.42 (s, 9H); HRMS (MH+) 581.2169.

EXAMPLE 141

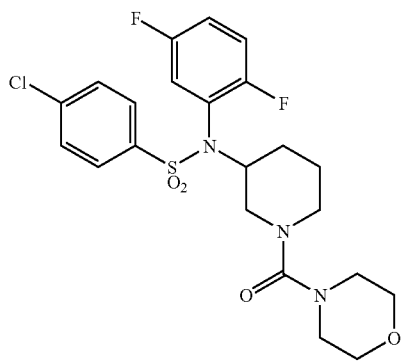

Step 1

To a solution of 2,5-difluoroaniline (2.58 g; 20 mmol) in pyridine (100 ml) was added 4-chlorobenzenesulfonyl chloride (4.22 g; 20 mmol) and the mixture was stirred 16 h at room temperature then 2 h at 45° C. The final reaction was concentrated, diluted in $CH_2Cl_2$, washed with brine, dried over $Na_2SO_4$, concentrated and the crude was purified by flash chromatography over silica gel (eluting Hexanes/$CH_2Cl_2$/AcOEt 70:10:2) to give 4.94 g (81%) of sulfonamide.

Step 2

To a solution of sulfonamide from Step 1 (7.59 g; 25 mmol), N-benzyl-3-hydroxypiperidine (m=n=0; p=2; 6.70 g; 35 mmol) and $PPh_3$ (9.18 g; 35 mmol) in THF at 0° C. was added DEAD (5.60 ml; 35 mmol) and the reaction was allowed to warm to room temperature overnight. The final solution was treated with diluted NaOH aqueous solution, extracted with $CH_2Cl_2$, and dried over $Na_2SO_4$. After concentration of the solvents, the crude was purified by flash chromatography over silica gel (eluting $CH_2Cl_2$/AcOEt 95:5 to 9:1) to afford 10.53 g (88%) of N-arylsulfonamide.

Step 3

A solution of N-arylsulfonamide from Step 2 (10.53 g; 22.1 mmol) in $CH_2Cl_2$ at 0° C. was treated with 1-chloroethyl chloroformate (26.5 mmol) then stirred 8 h at room temperature. The crude obtained after concentration of the solvent was diluted in anhydrous methanol and refluxed overnight. The final reaction mixture was concentrated, taken in 1 N NaOH aqueous solution, extracted with $CH_2Cl_2$, and dried over $Na_2SO_4$. After concentration of the solvent, the crude was purified by flash chromatography over silica gel (eluting $CH_2Cl_2$/MeOH 9:1 to $CH_2Cl_2$/MeOH/NH4OH 90:10:0.5) to yield 5.07 g (60%) of amine.

Step 4

To a solution of amine from Step 3 (50 mg; 0.13 mmol) in THF at 0° C. was added triphosgene (13 mg; 0.05 mmol) then $Et_3N$ (27 l; 0.20 mmol) and the reaction was stirred at room temperature overnight. The intermediate carbonyl chloride solution was treated with an excess of morpholine for 12 h, diluted with 1 N NaOH aqueous solution, extracted with $CH_2Cl_2$, dried over $Na_2SO_4$, and concentrated. Purification of the crude by preparative chromatography over silica gel afforded 31.1 mg of the title compound: $^1$H-NMR (300 MHz, $CDCl_3$) δ 7.54 (d, J=8.7 Hz, 2H), 7.42 (d, J=8.7 Hz, 2H), 6.85–7.15 (m, 3H), 4.08 (m, 1H), 3.50–3.85 (m, 4H), 3.10–3.35 (m, 4H), 2.90–3.05 (m, 2H), 2.09 (m, 1H), 1.65–2.00 (m, 3H), 1.39 (m, 2H); HRMS (M+H$^+$) 500.1219.

Using procedures similar to those of Example 141, including the use of a chiral N-benzyl-3-hydroxypiperidine in step 2, as well as procedures similar to Examples 51, 56, 94, 101, 117, 127, 130, and 134, the compounds in Table 10 were prepared. In Table 10 "EX" represents "Example".

TABLE 10

| EX | Structure | HRMS (MH$^+$) | LCMS (MH$^+$); Rt (min) |
|---|---|---|---|
| 142 | 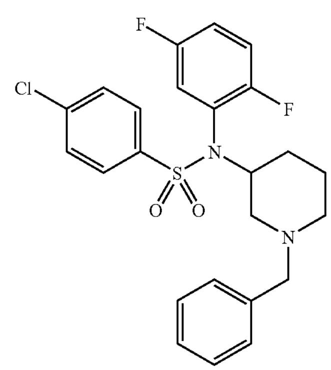 | — | 477.1; 4.71 |
| 143 | 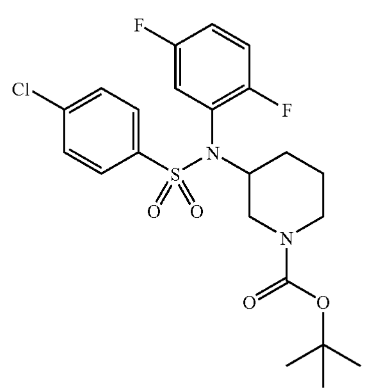 | — | 487.1; 5.46 |

TABLE 10-continued
| EX | Structure | HRMS (MH+) | LCMS (MH+); Rt (min) |
|---|---|---|---|
| 144 | 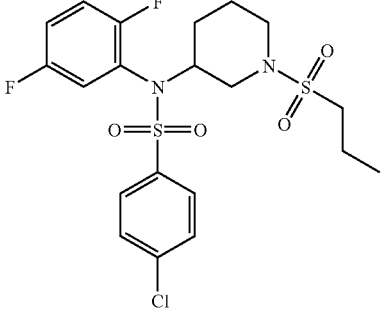 | — | 493.1; 5.36 |
| 145 | 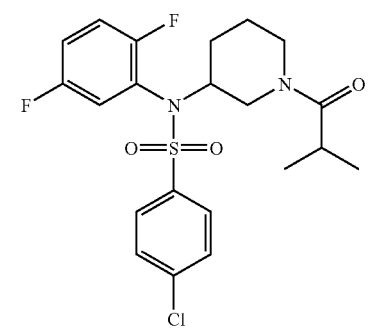 | — | 457.1; 5.31 |
| 146 | 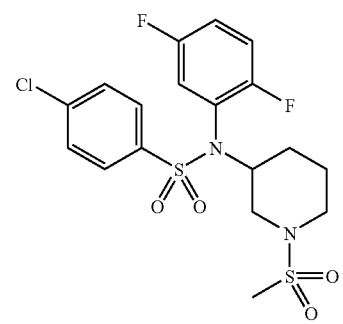 | 465.0528 | — |
| 147 | 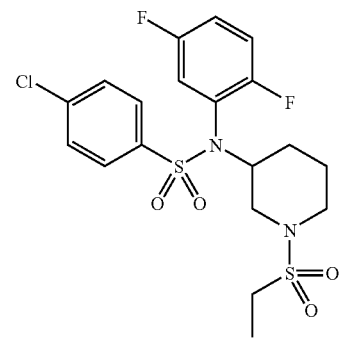 | 479.0681 | — |

TABLE 10-continued

| EX | Structure | HRMS (MH+) | LCMS (MH+); Rt (min) |
|---|---|---|---|
| 148 | 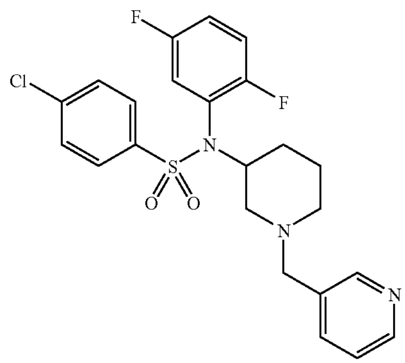 | — | 478.1; 3.76 |
| 149 | 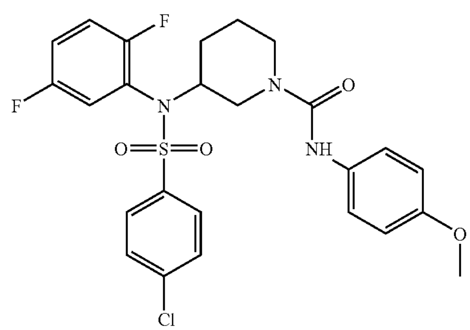 | — | 536.1; 5.31 |
| 150 | 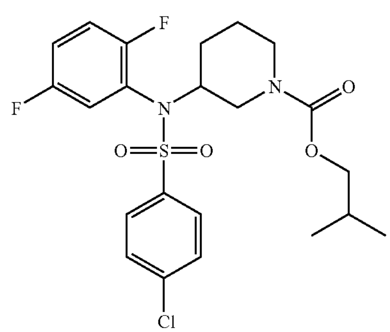 | — | 487.1; 5.71 |
| 151 | 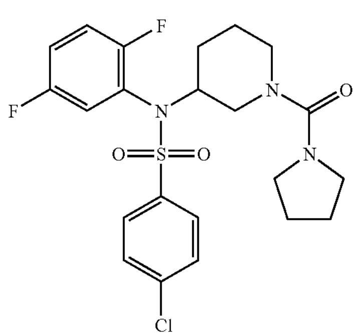 | — | 484.1; 5.31 |

TABLE 10-continued
| EX | Structure | HRMS (MH+) | LCMS (MH+); Rt (min) |
|---|---|---|---|
| 152 | 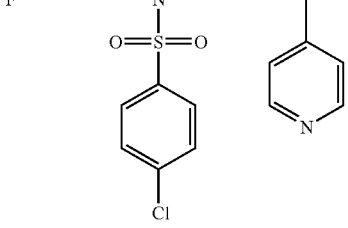 | — | 478.1; 4.01 |
| 153 | 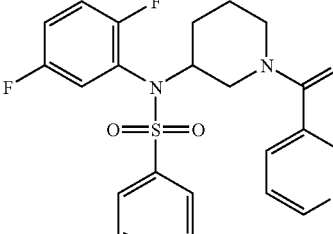 | 492.0957 | — |
| 154 | 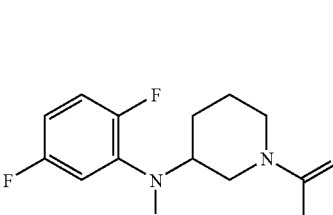 | 492.0957 | — |
| 155 | 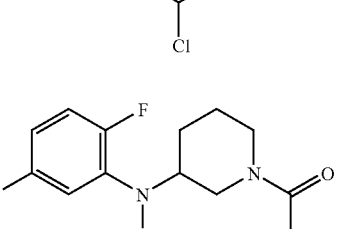 | 506.1110 | — |

TABLE 10-continued
| EX | Structure | HRMS (MH+) | LCMS (MH+); Rt (min) |
|---|---|---|---|
| 156 | 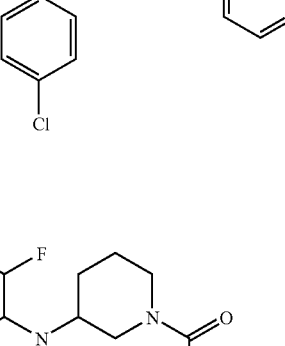 | 506.1125 | — |
| 157 | 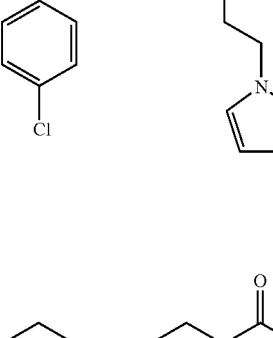 | 538.1493 | — |
| 158 | 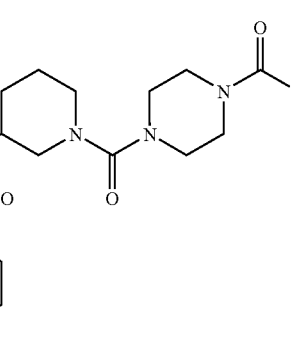 | 599.1900 | — |
| 159 | 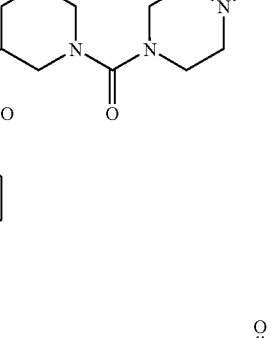 | 570.1633 | — |

TABLE 10-continued

| EX | Structure | HRMS (MH+) | LCMS (MH+); Rt (min) |
|---|---|---|---|
| 160 | 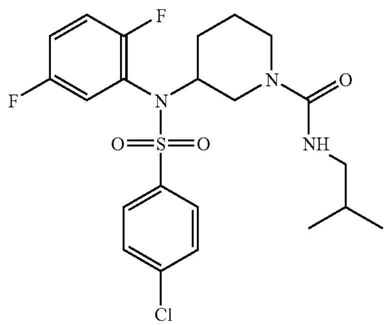 | 486.1425 | — |
| 161 | 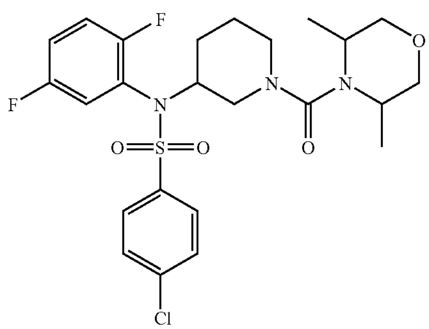 | 528.1520 | — |
| 162 | 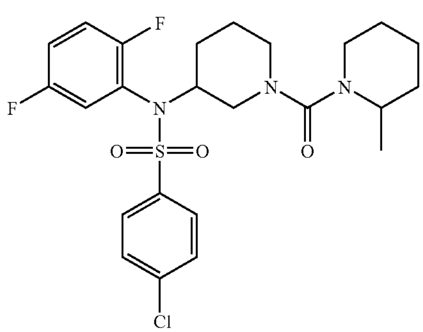 | 512.1589 | — |
| 163 | 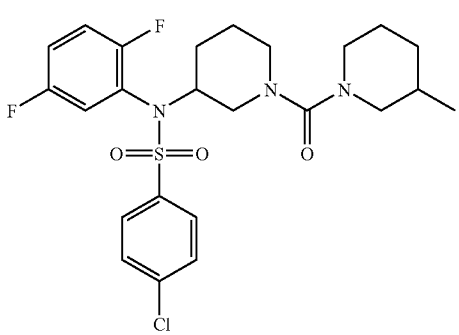 | 512.1589 | — |

TABLE 10-continued

| EX | Structure | HRMS (MH+) | LCMS (MH+); Rt (min) |
|---|---|---|---|
| 164 | 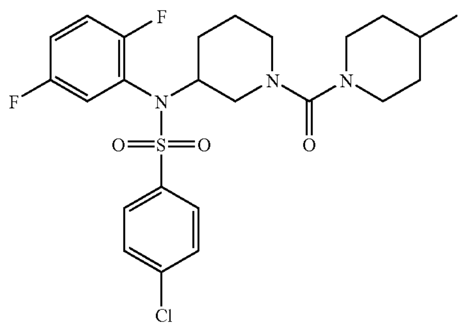 | 512.1589 | — |
| 165 | 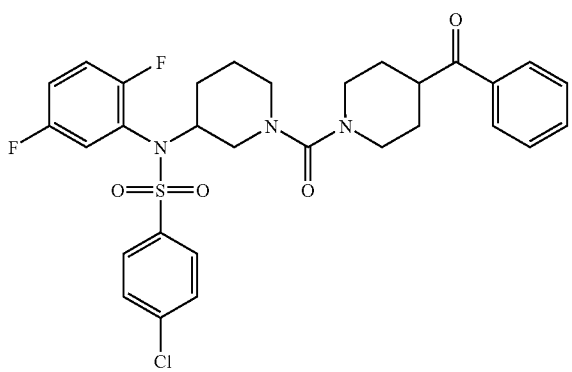 | 602.1697 | — |
| 166 | 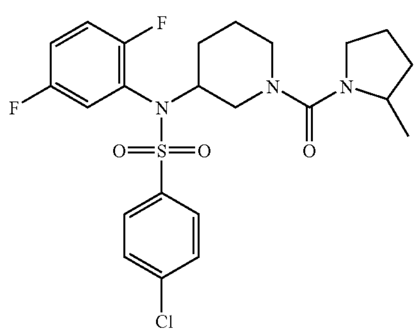 | 498.1423 | — |
| 167 | 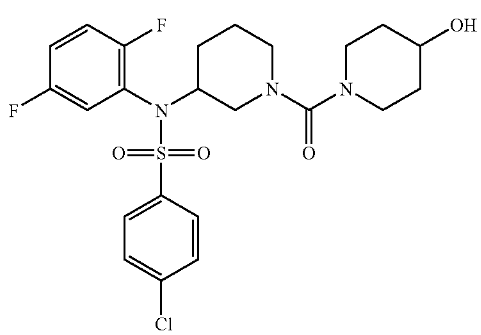 | 514.1384 | — |

TABLE 10-continued

| EX | Structure | HRMS (MH+) | LCMS (MH+); Rt (min) |
|---|---|---|---|
| 168 | 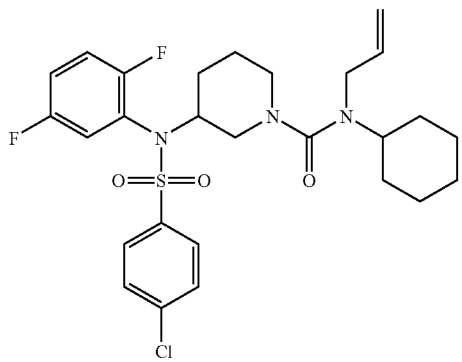 | 552.1905 | — |
| 169 | 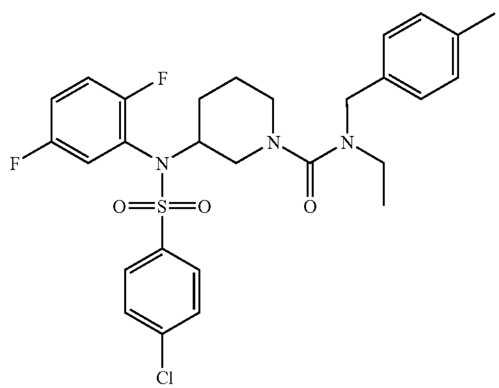 | 562.1737 | — |
| 170 | 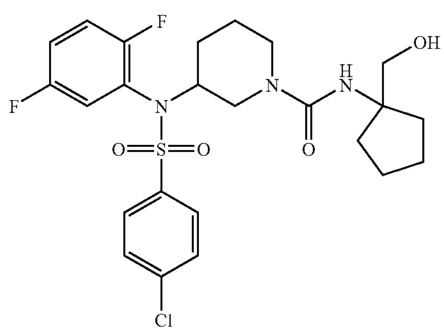 | 528.1531 | — |
| 171 | 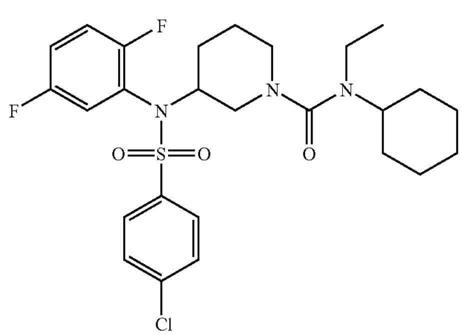 | 540.1895 | — |

TABLE 10-continued

| EX | Structure | HRMS (MH+) | LCMS (MH+); Rt (min) |
|---|---|---|---|
| 172 | 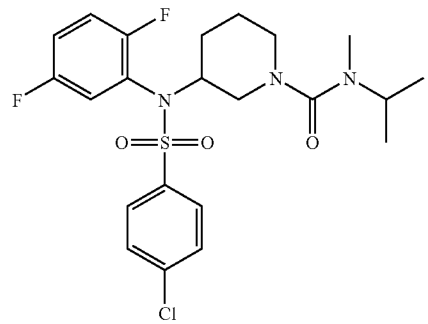 | 486.1424 | — |
| 173 | 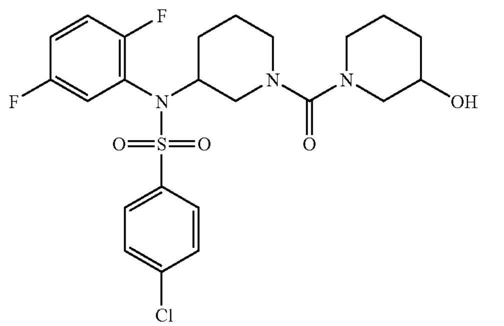 | 514.1389 | — |
| 174 | 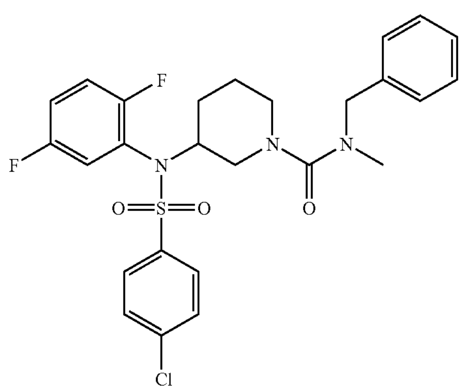 | 534.1435 | — |
| 175 | 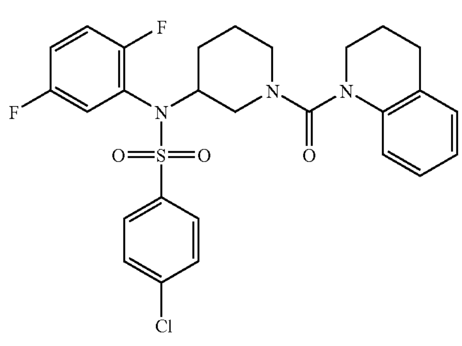 | 546.1422 | — |

TABLE 10-continued

| EX | Structure | HRMS (MH+) | LCMS (MH+); Rt (min) |
|---|---|---|---|
| 176 | 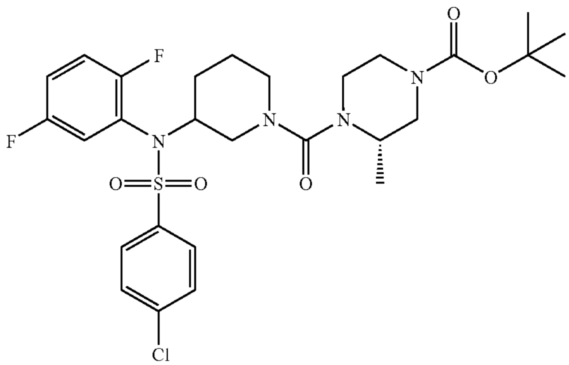 | 613.2060 | — |
| 177 | 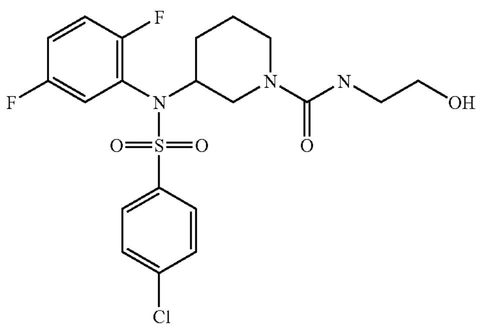 | 474.1073 | — |
| 178 | 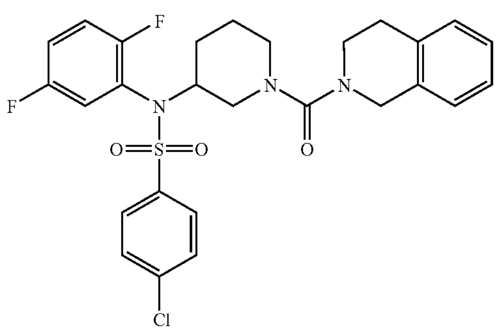 | 546.1427 | — |
| 179 | 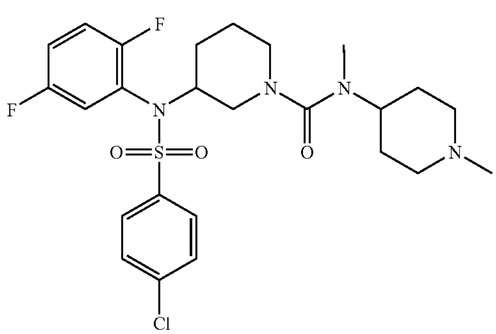 | 541.1848 | — |

TABLE 10-continued
| EX | Structure | HRMS (MH+) | LCMS (MH+); Rt (min) |
|---|---|---|---|
| 180 | 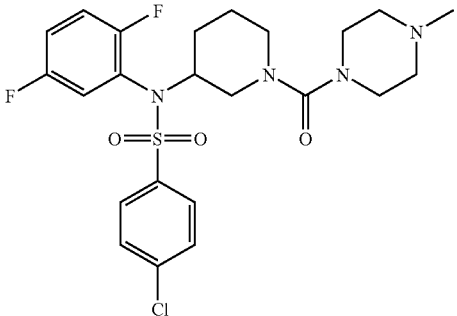 | 513.1544 | — |
| 181 | 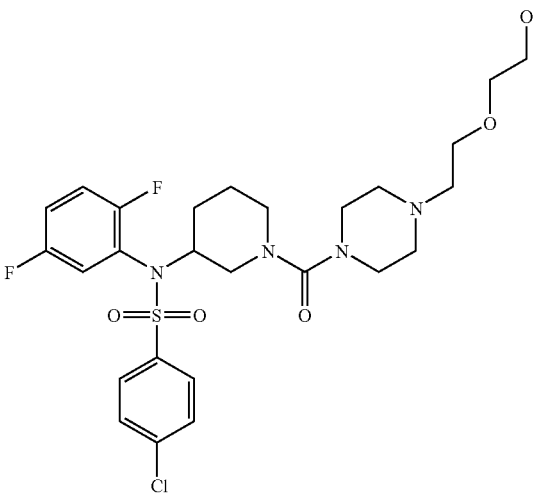 | 587.1911 | — |
| 182 | 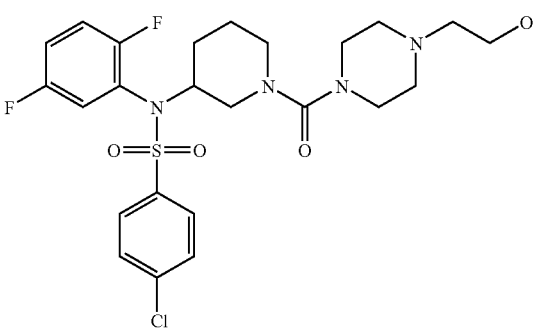 | 543.1638 | — |

TABLE 10-continued

| EX | Structure | HRMS (MH+) | LCMS (MH+); Rt (min) |
|---|---|---|---|
| 183 | 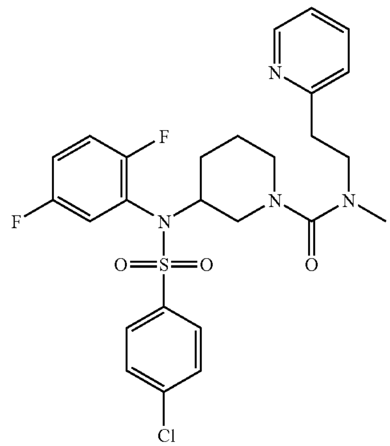 | 549.1531 | — |
| 184 | 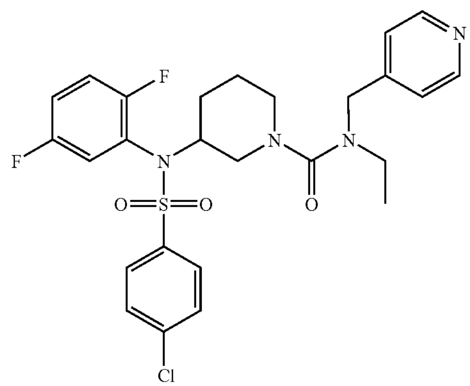 | — | 549.1; 4.56 |
| 185 | 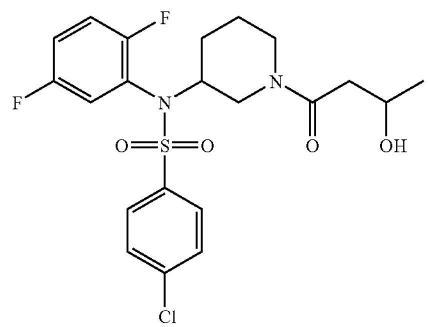 | 473.1117 | — |
| 186 | 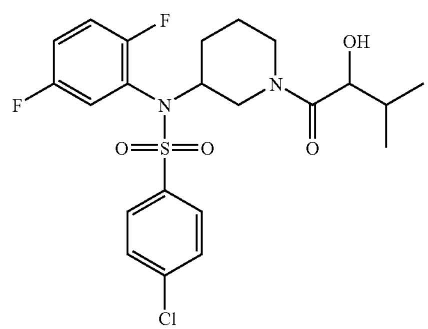 | 487.1276 | — |

TABLE 10-continued

| EX | Structure | HRMS (MH+) | LCMS (MH+); Rt (min) |
|----|-----------|------------|----------------------|
| 187 | 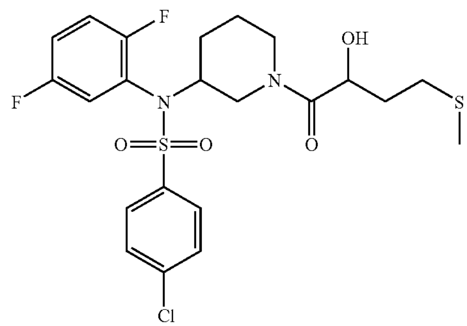 | 519.0987 | — |
| 188 | 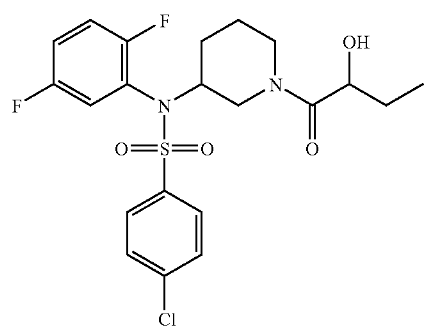 | 473.1117 | — |
| 189 | 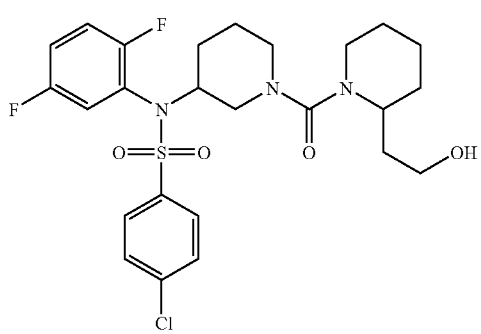 | 542.1702 | — |
| 190 | 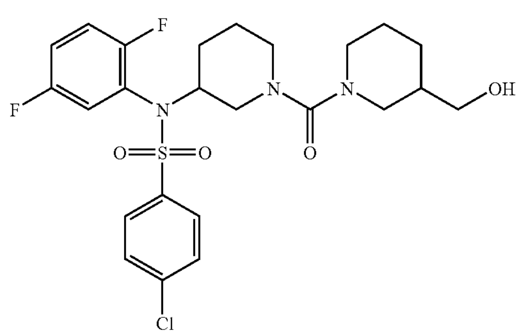 | 528.1545 | — |

TABLE 10-continued

| EX | Structure | HRMS (MH+) | LCMS (MH+); Rt (min) |
|---|---|---|---|
| 191 | 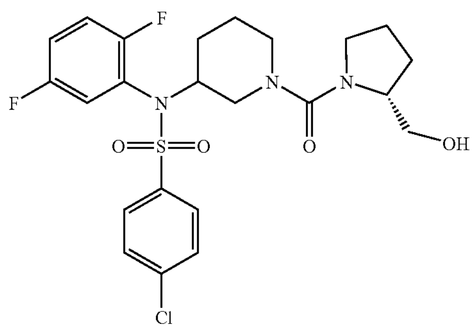 | 514.1374 | — |
| 192 | 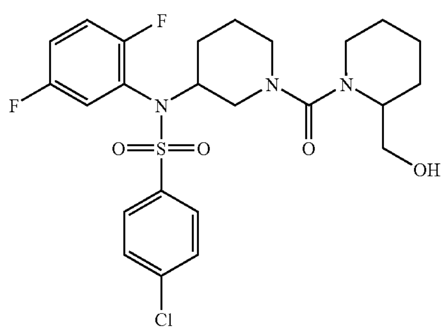 | 528.1540 | — |
| 193 | 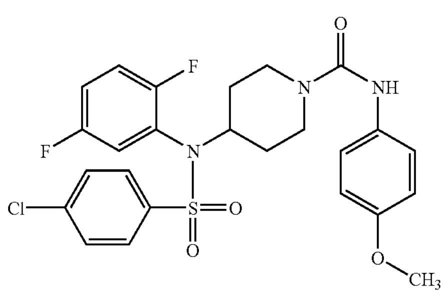 | — | 536.1; 5.11 |
| 194 | 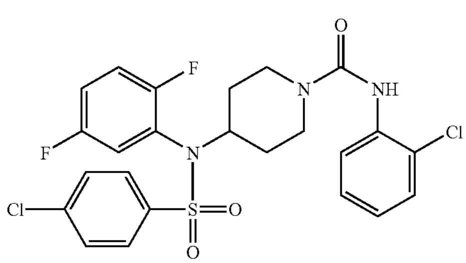 | — | 540.1; 5.26 |
| 195 | 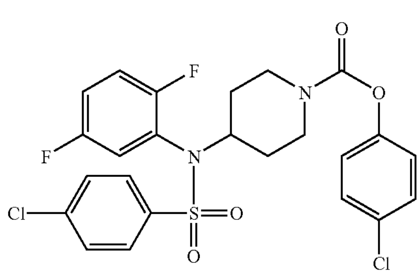 | — | 541.1; 5.61 |

TABLE 10-continued

| EX | Structure | HRMS (MH$^+$) | LCMS (MH$^+$); Rt (min) |
| --- | --- | --- | --- |
| 196 | 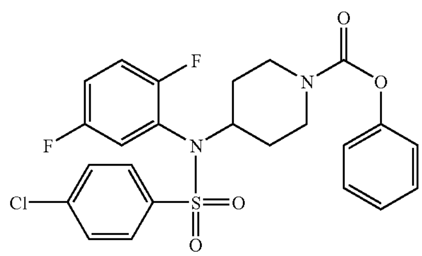 | — | 507.1; 5.41 |
| 197 | 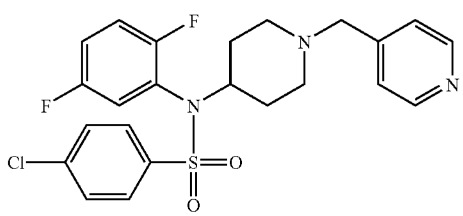 | — | 478.1; 4.21 |
| 198 | 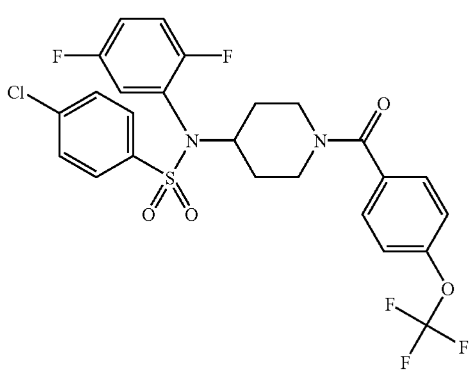 | — | 575.1; 5.31 |
| 199 | 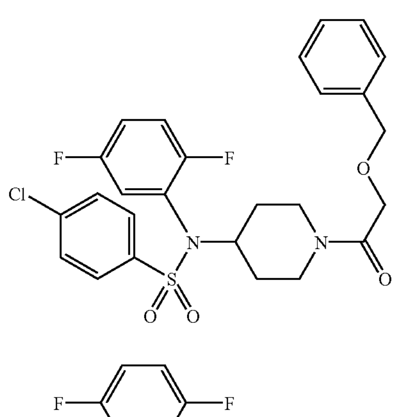 | — | 535.1; 5.16 |
| 200 | 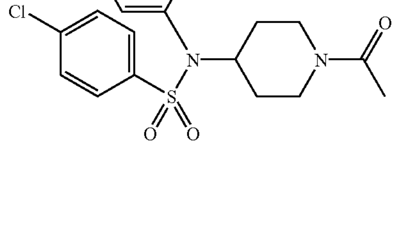 | — | 429.1; 4.76 |

TABLE 10-continued

| EX | Structure | HRMS (MH+) | LCMS (MH+); Rt (min) |
| --- | --- | --- | --- |
| 201 | 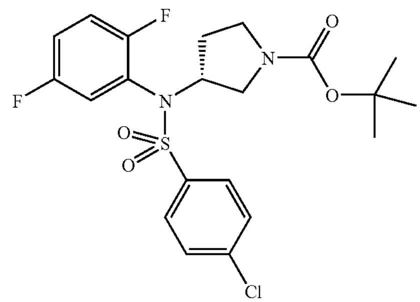 | — | 473.1; 5.61 |
| 202 | 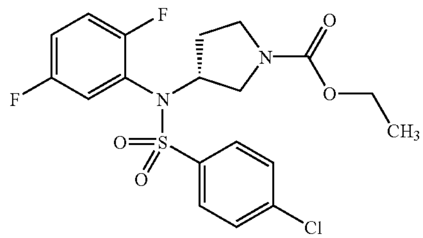 | — | 445.1; 5.21 |
| 203 | 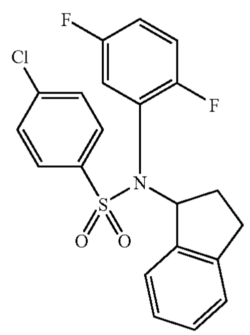 | — | 420.1; 5.71 |
| 204 | 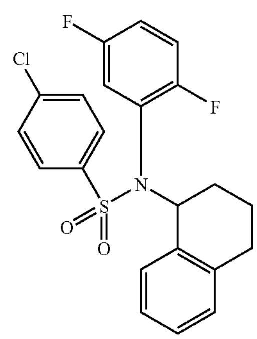 | — | 534.1; 5.96 |
| 205 | 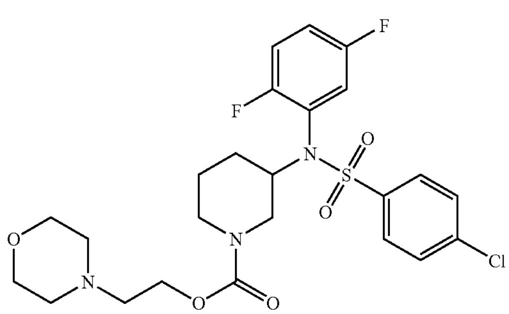 | 544.1488 | |

TABLE 10-continued

| EX | Structure | HRMS (MH+) | LCMS (MH+); Rt (min) |
|---|---|---|---|
| 206 | 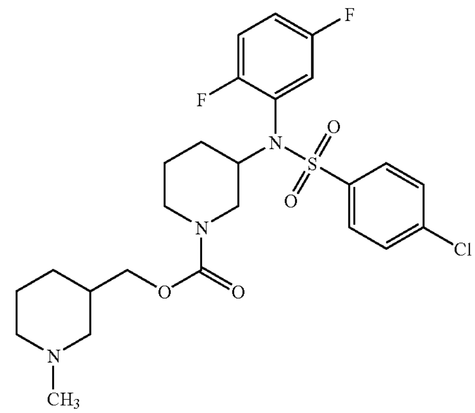 | 542.1684 | |
| 207 | 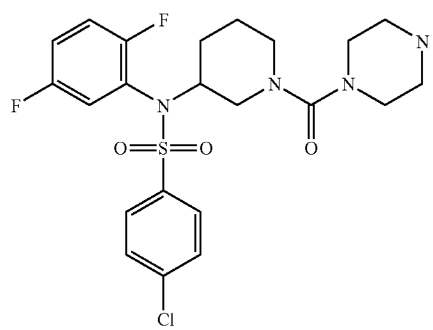 | 499.1388 | |
| 208 | 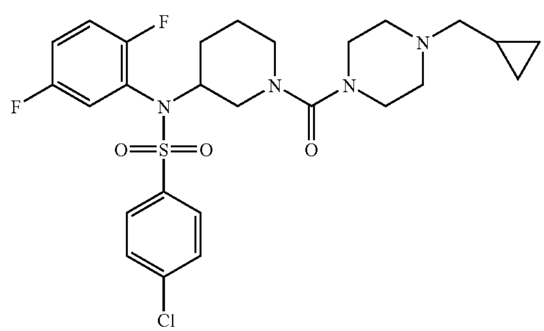 | 533.1855 | |
| 209 | 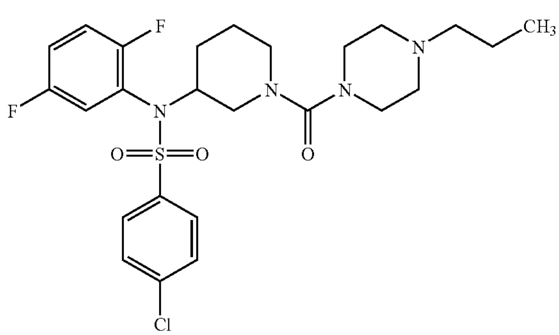 | 541.1856 | |

TABLE 10-continued

| EX | Structure | HRMS (MH+) | LCMS (MH+); Rt (min) |
|---|---|---|---|
| 210 | 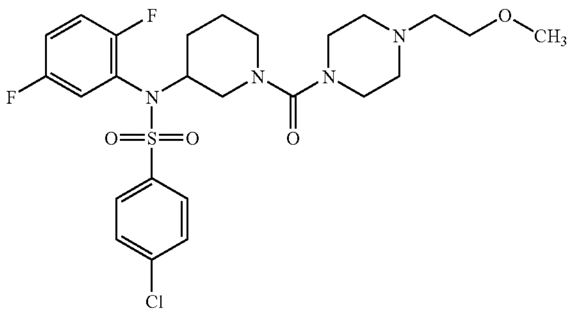 | 557.1811 | |
| 211 | 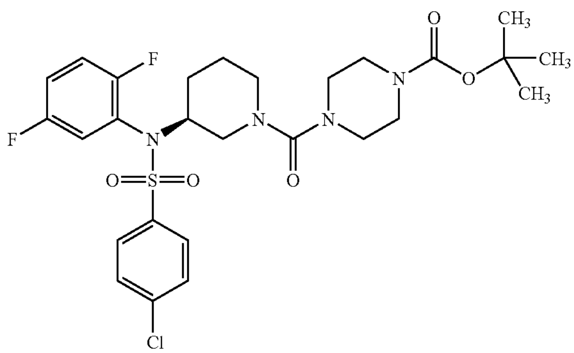 | 599.1894 | |
| 212 | 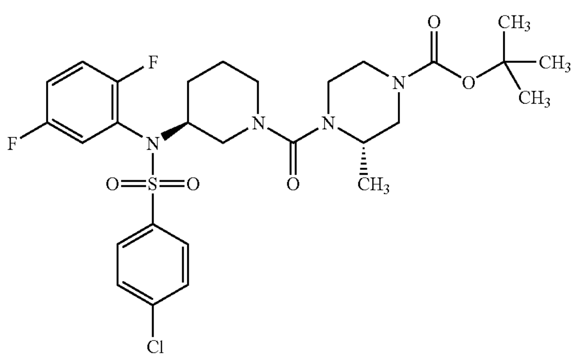 | 613.2078 | |
| 213 | 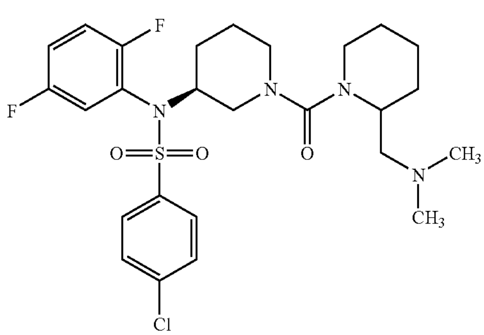 | 555.2004 | |

TABLE 10-continued

| EX | Structure | HRMS (MH+) | LCMS (MH+); Rt (min) |
|---|---|---|---|
| 214 | 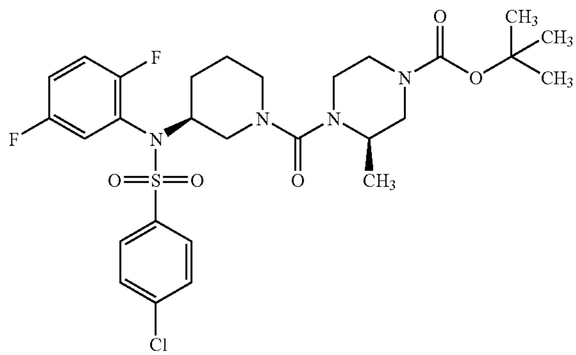 | 613.2054 | |
| 215 | 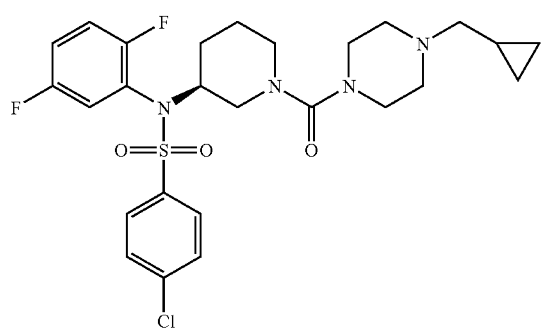 | 553.1861 | |
| 216 | 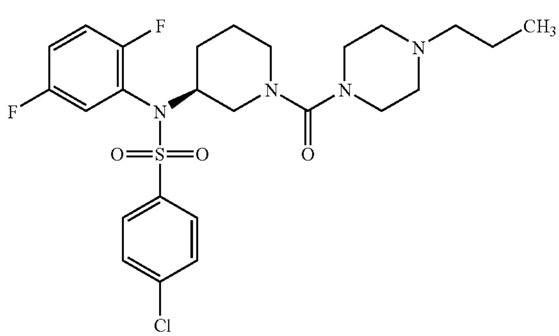 | 541.1846 | |
| 217 | 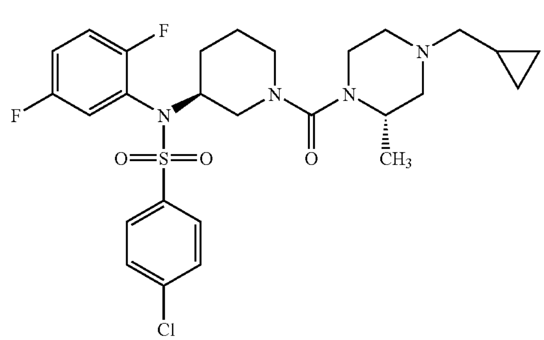 | 567.2012 | |

TABLE 10-continued
| EX | Structure | HRMS (MH+) | LCMS (MH+); Rt (min) |
|---|---|---|---|
| 218 | 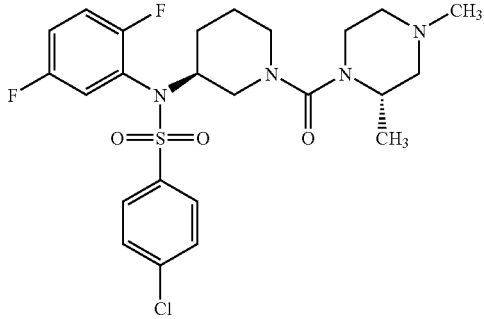 | 527.1702 | |
| 219 | 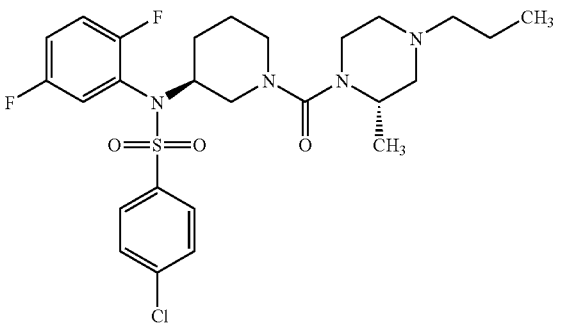 | 555.1998 | |
| 220 | 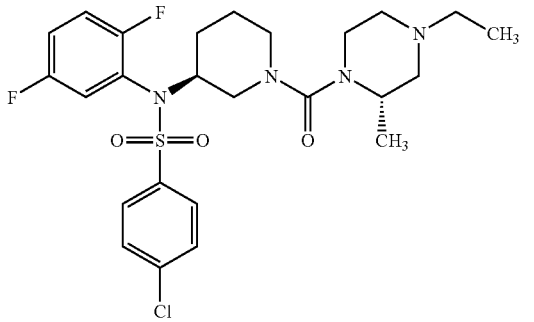 | 541.1842 | |

In Table 11 below, Example 221 was prepared following the procedure of Example 101 and Examples 222 to 230 were prepared following the procedure of Example 141.

TABLE 11

| EXAMPLE | COMPOUND |
|---|---|
| 221 | |
| 222 | |
| 223 | |
| 224 | |
| 225 | |

TABLE 11-continued

| EXAMPLE | COMPOUND |
|---|---|
| 226 | |
| 227 | |
| 228 | |
| 229 | |
| 230 | |

Assay:

Gamma secretase activity was determined as described by Zhang et a. (*Biochemistry*, 40 (16), 5049–5055, 2001). Activity is expressed either as a percent inhibition or as the concentration of compound producing 50% inhibition of enzyme activity.

Reagents. Antibodies W02, G2-10, and G2-11 were obtained from Dr. Konrad Beyreuther (University of Heidelberg, Heidelberg, Germany). W02 recognizes residues 5–8 of A peptide, while G2-10 and G2-11 recognize the specific C-terminal structure of A 40 and A 42, respectively. Biotin-4G8 was purchased from Senetec (St. Louis, Mo.). All tissue culture reagents used in this work were from Life Technologies, Inc., unless otherwise specified. Pepstatin A was purchased from Roche Molecular Biochemicals; DFK167 was from Enzyme Systems Products (Livermore, Calif.).

cDNA Constructs, Tissue Culture, and Cell Line Construction. The construct SPC99-Lon, which contains the first 18 residues and the C-terminal 99 amino acids of APP carrying the London mutation, has been described (Zhang, L., Song, L., and Parker, E. (1999) *J. Biol. Chem.* 274, 8966–8972). Upon insertion into the membrane, the 17 amino acid signal peptide is processed, leaving an additional leucine at the N-terminus of A. SPC99-Ion was cloned into the pcDNA4/TO vector (Invitrogen) and transfected into 293 cells stably transfected with pcDNA6/TR, which is provided in the T-REx system (Invitrogen). The transfected cells were selected in Dulbecco's modified Eagle's media (DMEM) supplemented with 10% fetal bovine serum, 100 units/mL penicillin, 100 g/mL streptomycin, 250 g/mL zeocin, and 5 g/mL blasticidin (Invitrogen). Colonies were screened for A production by inducing C99 expression with 0.1 g/mL tetracycline for 16–20 h and analyzing conditioned media with a sandwich immunoassay (see below). One of the clones, designated as pTRE.15, was used in these studies.

Membrane Preparation. C99 expression in cells was induced with 0.1 g/mL tetracycline for 20 h. The cells were pretreated with 1 M phorbol 12-myristate 13-acetate (PMA) and 1 M brefeldin A (BFA) for 5–6 h at 37 C before harvesting. The cells were washed 3 times with cold phosphate-buffered saline (PBS) and harvested in buffer A containing 20 mM Hepes (pH 7.5), 250 mM sucrose, 50 mM KCl, 2 mM EDTA, 2 mM EGTA, and Complete protease inhibitor tablets (Roche Molecular Biochemicals). The cell pellets were flash-frozen in liquid nitrogen and stored at −70 C. before use.

To make membranes, the cells were resuspended in buffer A and lysed in a nitrogen bomb at 600 psi. The cell lysate was centrifuged at 1500 g for 10 min to remove nuclei and large cell debris. The supernatant was centrifuged at 100000 g for 1 h. The membrane pellet was resuspended in buffer A plus 0.5 M NaCl, and the membranes were collected by centrifugation at 200000 g for 1 h. The salt-washed membrane pellet was washed again in buffer A and centrifuged at 100000 g for 1 h. The final membrane pellet was resuspended in a small volume of buffer A using a Teflon-glass homogenizer. The protein concentration was determined, and membrane aliquots were flash-frozen in liquid nitrogen and stored at −70 C.

-Secretase Reaction and A Analysis. To measure -secretase activity, membranes were incubated at 37 C for 1 h in 50 L of buffer containing 20 mM Hepes (pH 7.0) and 2 mM EDTA. At the end of the incubation, Aβ 40 and Aβ 42 were measured using an electrochemiluminescence (ECL)-based immunoassay. Aβ 40 was identified with antibody pairs TAG-G2-10 and biotin-W02, while A 42 was identified with TAG-G2-11 and biotin-4G8. The ECL signal was measured using an ECL-M8 instrument (IGEN International, Inc.) according to the manufacturer's instructions. The data presented were the means of the duplicate or triplicate measurements in each experiment. The characteristics of -secretase activity described were confirmed using more than five independent membrane preparations.

The compounds of Examples 1–214 had an $IC_{50}$ within the range of about 0.028 to about 69.550 μM. The compounds of Examples 14, 16, 17, 18, 20, 56, 62, 68, 79, 159, 161, 162, 180, 181, 182, 192, 213 and 214 had an $IC_{50}$ within the range of about 0.028 to about 0.345 μM.

Pharmaceutical compositions can comprise one or more of the compounds of formula I. For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active compound. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparation is subdivided into suitably sized unit doses containing appropriate quantities of the active compound, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in one to four divided doses.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula:

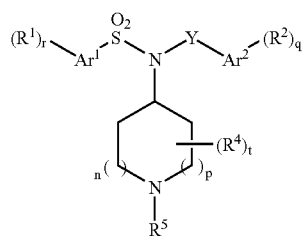

(I)

or pharmaceutically acceptable salts or solvates thereof, wherein:
(A) $Ar^1$ and $Ar^2$ are Independently selected from aryl or heteroaryl;
(B) Y is bond, or Y is a —$C(R^3)_2)_{1-3}$— group;
(C) each $R^1$ is independently selected from:
   (1) aryl;
   (2) aryl substituted with one or more substituents independently selected from: halogen, $CF_3$, $(C_1-C_6)$alkyl, $(C_1-C_6)$alkoxy, $OCF_3$, $NH_2$, or CN;
   (3) heteroaryl;
   (4) heteroaryl substituted with one or more substituents independently selected from: halogen, $CF_3$, $(C_1-C_6)$alkyl, $(C_1-C_6)$alkoxy, $OCF_3$, $NH_2$, or CN;
   (5) halogen;
   (6) —$CF_3$;
   (7) —$OCF_3$;
   (8) —CN;
   (9) —$NO_2$;
   (10) —$NH_2$;
   (11) —$C(O)NH(C_1-C_6)$alkyl;
   (12) —$C(O)N((C_1-C_6)$alkyl$)_2$ wherein each $(C_1-C_6)$ alkyl group is the same or different;
   (13) —$C(O)N((C_1-C_6)$alkyl$)_2$ wherein each $(C_1-C_6)$ alkyl group is the same or different, and said $(C_1-C_6)$ alkyl groups taken together with the nitrogen to which they are bound form a ring;
   (14) —$NHC(O)(C_1-C_6)$alkyl;
   (15) —$NHC(O)O(C_1-C_6)$alkyl;
   (16) —$NHC(O)NH(C_1-C_6)$alkyl;
   (17) —$NHSO_2(C_1-C_6)$alkyl;
   (18) —OH;
   (19) —$OC(O)(C_1-C_6)$alkyl;
   (20) —Oaryl; or
   (21) —Oar$(C_1-C_6)$alkyl;
(D) each $R^2$ is independently selected from:
   (1) —$(C_1-C_6)$alkyl;
   (2) halogen;
   (3) —$CF_3$;
   (4) —$OCF_3$;
   (5) —CN;
   (6) —$NO_2$;
   (7) —$NH_2$;
   (8) —$C(O)O(C_1-C_6)$alkyl;
   (9) —$C(O)NH(C_1-C_6)$alkyl;
   (10) —$N(C_1-C_6$alkyl$)_2$ wherein each $C_1-C_6$alkyl substituent is the same or different;
   (11) —$N(C_1-C_6$alkyl$)_2$ wherein each $C_1-C_6$alkyl substituent is the same or different, and the $C_1-C_6$alkyl substituents together with the nitrogen atom to which they are bound form a ring;
   (12) —$NHC(O)(C_1-C_6)$alkyl;
   (13) —$NHC(O)O(C_1-C_6)$alkyl;
   (14) —$NHC(O)NH(C_1-C_6)$alkyl;
   (15) —$NHSO_2(C_1-C_6)$alkyl;
   (16) —OH;
   (17) —$OC(O)(C_1-C_6)$alkyl;
   (18) —$O(C_1-C_6)$alkyl;
   (19) —Oaryl;
   (20) —Oar$(C_1-C_6)$alkyl;
   (21) -aryl;
   (22) -aryl substituted with one or more substituents independently selected from: halogen, $CF_3$, $(C_1-C_6)$ alkyl, $(C_1-C_6)$alkoxy, $OCF_3$, $NH_2$, or CN;
   (23) -heteroaryl;
   (24) -heteroaryl substituted with one or more substituents independently selected from: halogen, $CF_3$, $(C_1-C_6)$alkyl, $(C_1-C_6)$alkoxy, $OCF_3$, $NH_2$, or CN;
   (25) -a group selected from:

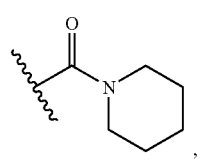

(8.0)

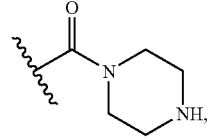

(9.0)

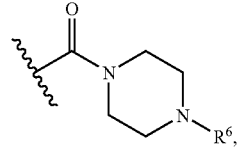

(10.0)

-continued

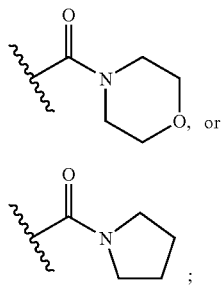
(11.0)

or

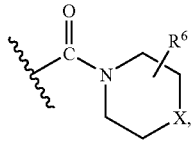
(12.0)

(26) —C(O)N((C$_1$–C$_6$)alkyl)$_2$ wherein each alkyl group is independently selected; or
(27) —C(O)N((C$_1$–C$_6$)alkyl)$_2$ wherein each alkyl group is independently selected and wherein the alkyl groups taken together with the nitrogen atom form a heterocycloalkyl ring;

(E) each R$^3$ is independently selected from H or —(C$_1$–C$_3$)alkyl;
(F) each R$^4$ is independently selected from:
(1) —(C$_1$–C$_3$)alkyl;
(2) —OH; or
(3) —O(C$_1$–C$_3$)alkyl;
(G) R$^5$ is selected from:
(1) —(C$_1$–C$_6$)alkyl;
(2) -aryl;
(3) -heteroaryl;
(4) —(C$_1$–C$_3$)alkylene-O(C$_1$–C$_3$)alkyl;
(5) —(C$_1$–C$_6$)alkylene-S(O)$_{0-2}$(C$_1$–C$_3$)alkyl;
(6) —(C$_1$–C$_6$)alkylene-S(O)$_{0-2}$NH(C$_1$–C$_3$)alkyl;
(7) —C(O)(C$_1$–C$_6$)alkyl;
(8) —C(O)aryl;
(9) —C(O)ar(C$_1$–C$_3$)alkyl;
(10) —C(O)heteroaryl;
(11) —C(O)heteroar(C$_1$–C$_3$)alkyl;
(12) —C(O)O(C$_1$–C$_6$)alkyl;
(13) —C(O)NH(C$_1$–C$_6$)alkyl;
(14) —C(O)N((C$_1$–C$_6$)alkyl)$_2$ wherein each C$_1$–C$_6$alkyl group is the same or different;
(15) —C(O)N((C$_1$–C$_6$)alkyl)$_2$ wherein each C$_1$–C$_6$alkyl group is the same or different and wherein the C$_1$–C$_6$ alkyl groups taken together with the nitrogen to which they are bound form a heterocycloalkyl ring;
(16) —C(O)(C$_1$–C$_3$)alkylene-NH(C$_1$–C$_3$)alkyl;
(17) —C(O)(C$_1$–C$_3$)alkylene-N((C$_1$–C$_3$)alkyl)$_2$ wherein each alkyl group is independently selected;
(18) —SO$_2$(C$_1$–C$_6$)alkyl;
(19) —SO$_2$NH(C$_1$–C$_6$)alkyl;
(20) —SO$_2$N((C$_1$–C$_6$)alkyl)$_2$ wherein each C$_1$–C$_6$alkyl is the same or different;
(21) —SO$_2$N((C$_1$–C$_6$)alkyl)$_2$ wherein each C$_1$–C$_6$alkyl is the same or different, and wherein the C$_1$–C$_6$ alkyl groups taken together with the nitrogen to which they are bound form a heterocycloalkyl ring; or

(22) a group of the formula:

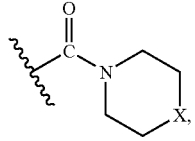
(13.0)

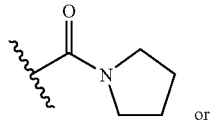
(13.1)

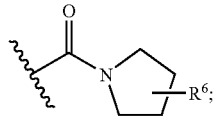
(14.0)

or (15.0)

(H) R$^6$ is —H or —(C$_1$–C$_6$) alkyl;
(I) X is selected from: CH$_2$, O, S, SO, SO$_2$, or N—R$^7$;
(J) R$^7$ is selected from:
(1) —(C$_1$–C$_6$)alkyl;
(2) —(C$_3$–C$_6$)cycloalkyl;
(3) —(C1–C3)alkylene-(C3–C6)cycloalkyl;
(4) -aryl;
(5) -ar(C$_1$–C$_3$)alkyl;
(6) -heteroaryl;
(7) -heteroar(C$_1$–C$_3$)alkyl;
(8) —C(O)(C$_1$–C$_6$)alkyl;
(9) —C(O)aryl;
(10) —C(O)ar(C$_1$–C$_3$)alkyl;
(11) —C(O)heteroaryl;
(12) —C(O)heteroar(C$_1$–C$_3$)alkyl;
(13) —C(O)O(C$_1$–C$_6$)alkyl;
(14) —C(O)NH(C$_1$–C$_6$)alkyl;
(15) —C(O)N((C$_1$–C$_6$)alkyl)$_2$ wherein each C$_1$–C$_6$alkyl group is the same or different;
(16) —C(O)N((C$_1$–C$_6$)alkyl)$_2$ wherein each C$_1$–C$_6$alkyl group is the same or different, and the C$_1$–C$_6$alkyl groups taken together with the nitrogen to which they are bound form a heterocycloalkyl ring;
(17) —C(O)(C$_1$–C$_3$)alkylene-NH(C$_1$–C$_3$)alkyl;
(18) —C(O)(C$_1$–C$_3$)alkylene-N((C$_1$–C$_3$)alkyl)$_2$ wherein the C$_1$–C$_3$alkyl groups are the same or different; or
(19) —(C$_1$–C$_3$)alkylene-O—(C$_1$–C$_3$)alkyl;

(K) n and p are both 1;
(L) r is 0 to 3;
(M) q is 0 to 3; and
(N) t is 0 to 3.

2. The compound of claim 1 having the formula:

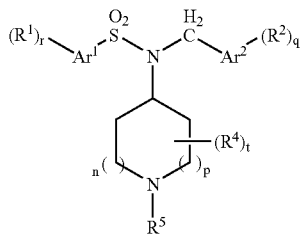

(Ia)

3. The compound of claim 1 having the formula:

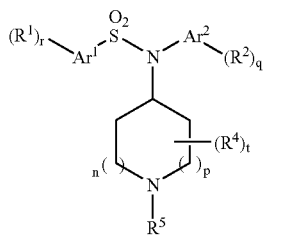

(Ib)

4. The compound of claim 1 wherein:
(1) $Ar^1$ is a 1,4-arylene;
(2) $R^1$ is selected from: halo, $CF_3$, $OCF_3$, —CN, —$NO_2$, —$NH_2$, —NHC(O)($C_1$–$C_6$)alkyl, —$NHSO_2$($C_1$–$C_6$)alkyl, or substituted aryl;
(3) r is 1;
(4) t is 0; and
(5) Y is selected from: a bond or methylene.

5. The compound of claim 4 wherein:
(1) $Ar^1$ is phenyl; and
(2) $R^1$ is halo, —$CF_3$, —$OCF_3$.

6. The compound of claim 5 wherein when $R^1$ is halo said halo is chloro.

7. The compound of claim 2 wherein:
(1) $Ar^1$ is a 1,4-arylene;
(2) $R^1$ is selected from: halo, $CF_3$, $OCF_3$, —CN, —$NO_2$, —$NH_2$, —NHC(O)($C_1$–$C_6$)alkyl, —$NHSO_2$($C_1$–$C_6$)alkyl, or substituted aryl;
(3) r is 1;
(4) t is 0;
(5) $Ar^2$ is a 1,4-arylene;
(6) $R^2$ is selected from:
  (a) —O($C_1$–$C_3$)alkyl,
  (b) —C(O)O($C_1$–$C_6$)alkyl,
  (c) —C(O)NH($C_1$–$C_6$)alkyl,
  (d) —C(O)N(($C_1$–$C_6$)alkyl)$_2$,
  (e) —C(O)N(($C_1$–$C_6$)alkyl)$_2$ wherein the alkyl groups taken together with the nitrogen to which they are bound form a heterocycloalkyl ring,
  (f) substituted aryl,
  (g) substituted heteroaryl;
(7) q is 1; and
(8) $R^5$ is selected from:
  (a) substituted aryl,
  (b) substituted heteroaryl,
  (c) —C(O)($C_1$–$C_6$)alkyl,
  (d) —C(O)-ar($C_1$–$C_3$)alkyl,
  (e) —C(O)aryl,
  (f) —C(O)-heteroar($C_1$–$C_3$)alkyl,
  (g) —C(O)heteroaryl,
  (h) —C(O)O($C_1$–$C_6$)alkyl,
  (i) —C(O)NH($C_1$–$C_6$)alkyl,
  (j) —C(O)N(($C_1$–$C_6$)alkyl)$_2$,
  (k) —C(O)N(($C_1$–$C_6$)alkyl)$_2$ wherein the alkyl groups taken together with the nitrogen to which they are bound form a heterocycloalkyl ring,
  (l) —C(O)($C_1$–$C_3$)alkylene-NH($C_1$–$C_3$)alkyl, or
  (m) —C(O)($C_1$–$C_3$)alkylene-N(($C_1$–$C_3$)alkyl)$_2$.

8. The compound of claim 3 wherein:
(1) $Ar^1$ is a 1,4-arylene;
(2) $R^1$ is selected from: halo, $CF_3$, $OCF_3$, —CN, —$NO_2$, —$NH_2$, —NHC(O)($C_1$–$C_6$)alkyl, —$NHSO_2$($C_1$–$C_6$)alkyl, or substituted aryl;
(3) r is 1;
(4) t is 0;
(5) $Ar^2$ is phenyl;
(6) $R^2$ is selected from: —O($C_1$–$C_3$)alkyl or halogen; and
(7) $R^5$ is selected from:
  (a) substituted aryl,
  (b) substituted heteroaryl,
  (c) —C(O)($C_1$–$C_6$)alkyl,
  (d) —C(O)-ar($C_1$–$C_3$)alkyl,
  (e) —C(O)aryl,
  (f) —C(O)-heteroar($C_1$–$C_3$)alkyl,
  (g) —C(O)heteroaryl,
  (h) —C(O)O($C_1$–$C_6$)alkyl,
  (i) —C(O)NH($C_1$–$C_6$)alkyl,
  (j) —C(O)N(($C_1$–$C_6$)alkyl)$_2$,
  (k) —C(O)N(($C_1$–$C_6$)alkyl)$_2$ wherein the alkyl groups taken together with the nitrogen to which they are bound form a heterocycloalkyl ring,
  (l) —C(O)($C_1$–$C_3$)alkylene-NH($C_1$–$C_3$)alkyl, or
  (m) —C(O)($C_1$–$C_3$)alkylene-N(($C_1$–$C_3$)alkyl)$_2$.

9. The compound of claim 1 selected from:

46

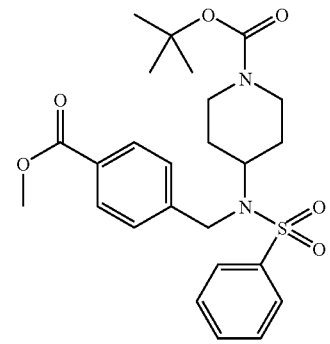

-continued
47
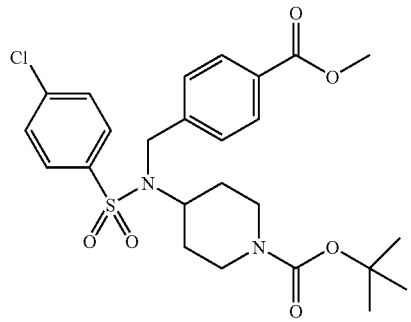
48
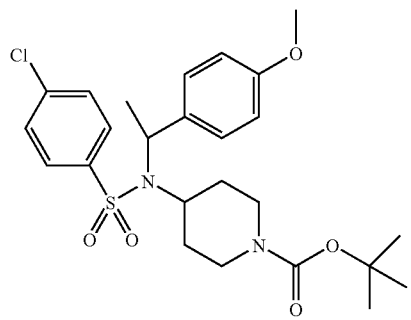
49
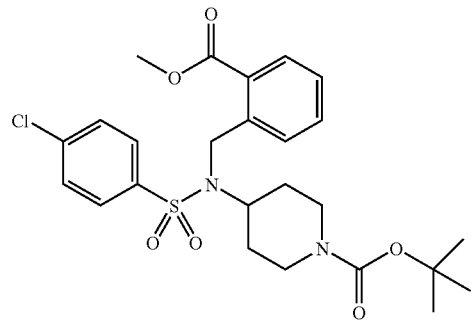
193
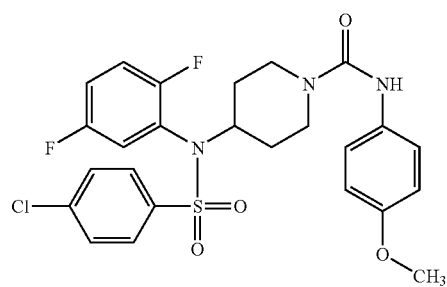
194
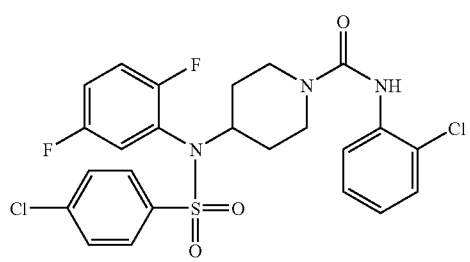
-continued
195
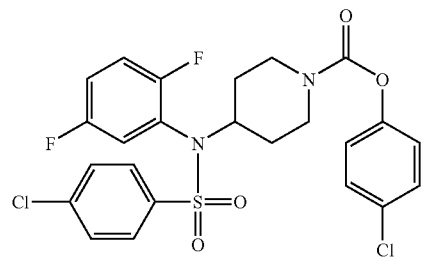
196
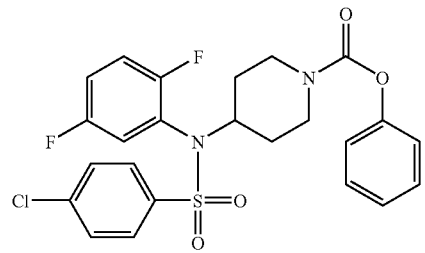
198
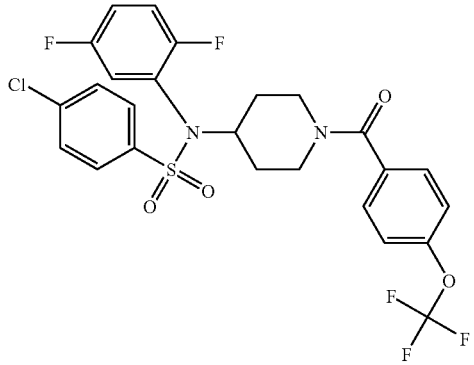
199
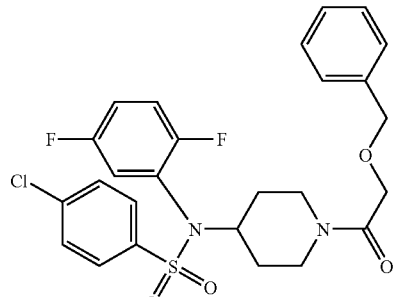
200
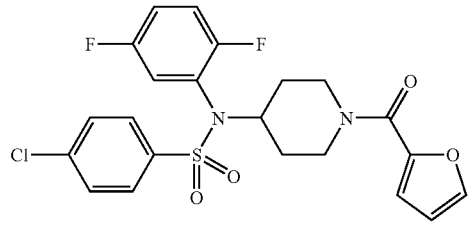

-continued

222 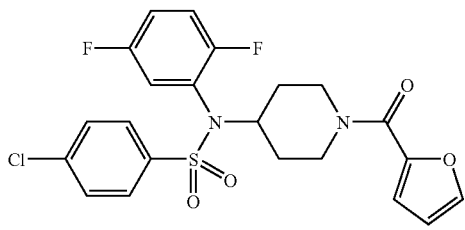

223 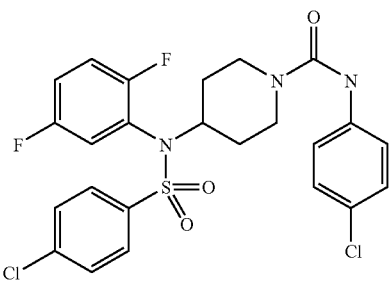

224 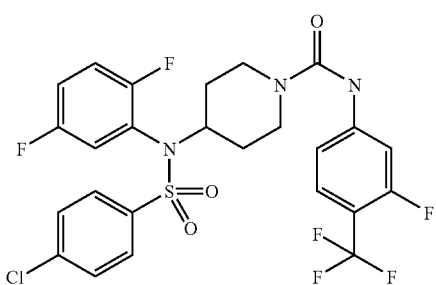

225 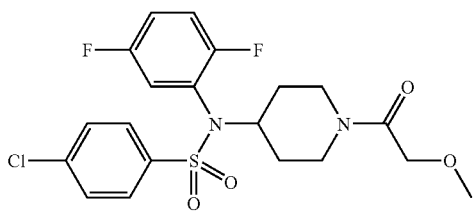

226 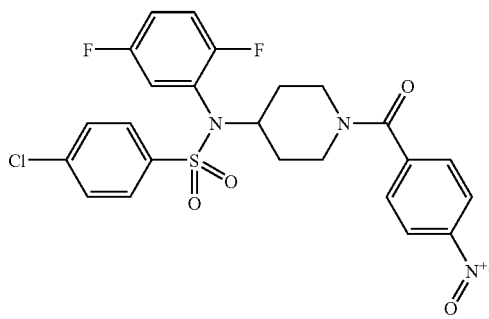

227 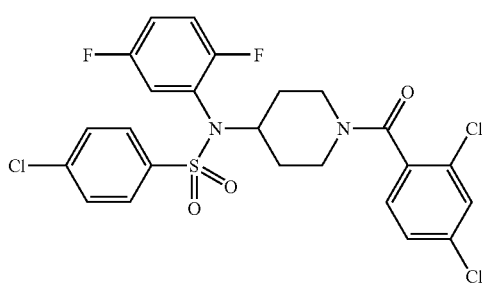

-continued

228 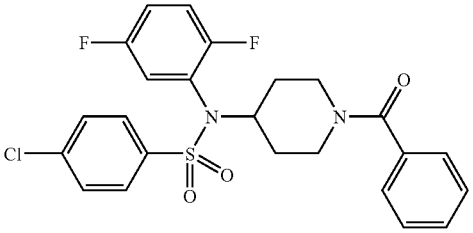

10. A pharmaceutical composition comprising at least one compound of claim 1 and at least one pharmaceutically acceptable carrier.

11. A method of inhibiting gamma-secretase in a patient in need of such treatment comprising administering to said patient an effective amount of a compound of claim 1.

12. A method of treating neurodegenerative diseases in a patient in need of such treatment comprising administering to said patient an effective amount of a compound of claim 1.

13. A method of inhibiting the deposition of beta amyloid protein in a patient in need of such treatment comprising administering to said patient an effective amount of a compound of claim 1.

14. A method of treating Alzheimer's disease in a patient in need of such treatment comprising administering to said patient an effective amount of a compound of claim 1.

15. A compound of the formula:

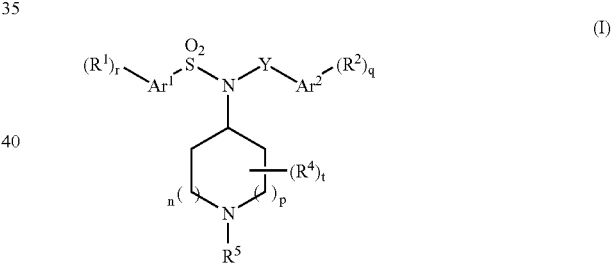

(I)

or pharmaceutically acceptable salts or solvates thereof, wherein:

(A) $Ar^1$ and $Ar^2$ are independently selected from aryl or heteroaryl;
(B) Y is bond, or Y is a —$(C(R^3)_2)_{1-3}$— group;
(C) each $R^1$ is independently selected from:
   (1) —$(C_1-C_6)$alkyl;
   (2) aryl;
   (3) aryl substituted with one or more substituents independently selected from: halogen, $CF_3$, $(C_1-C_6)$alkyl, $(C_1-C_6)$alkoxy, $OCF_3$, $NH_2$, or CN;
   (4) heteroaryl;
   (5) heteroaryl substituted with one or more substituents independently selected from: halogen $CF_3$, $(C_1-C_6)$alkyl, $(C_1-C_6)$alkoxy, $OCF_3$, $NH_2$, or CN;
   (6) halogen;
   (7) —$CF_3$;
   (8) —$CF_3$;
   (9) —CN;
   (10) —$NO_2$;
   (11) —$NH_2$;

(12) —C(O)NH($C_1$–$C_6$)alkyl;
(13) —C(O)N(($C_1$–$C_6$)alkyl)$_2$ wherein each ($C_1$–$C_6$) alkyl group is the same or different;
(14) —C(O)N(($C_1$–$C_6$)alkyl)$_2$ wherein each ($C_1$–$C_6$) alkyl group is the same or different, and said ($C_1$–$C_6$) alkyl groups taken together with the nitrogen to which they are bound form a ring;
(15) —NHC(O)($C_1$–$C_6$)alkyl;
(18) —NHC(O)O($C_1$–$C_6$)alkyl;
(17) —NHC(O)NH($C_1$–$C_6$)alkyl;
(18) —NHSO$_2$($C_1$–$C_6$)alkyl;
(19) —OH;
(20) —OC(O)($C_1$–$C_6$)alkyl;
(21) —O($C_1$–$C_6$)alkyl,
(22) —Oaryl; or
(23) —Oar($C_1$–$C_6$)alkyl;

(D) each $R^2$ is independently selected from:
(1) —($C_1$–$C_6$)alkyl;
(2) fluorine;
(3) —CF$_3$;
(4) —OCF$_3$;
(5) —CN;
(6) —NO$_2$;
(7) —NH$_2$;
(8) —C(O)O($C_1$–$C_6$)alkyl;
(9) —C(O)NH($C_1$–$C_6$)alkyl;
(10) —N($C_1$–$C_6$alkyl)$_2$ wherein each $C_1$–$C_6$alkyl substituent is the same or different;
(11) —N($C_1$–$C_6$alkyl)$_2$ wherein each $C_1$–$C_6$alkyl substituent is the same or different, and the $C_1$–$C_6$alkyl substituents together with the nitrogen atom to which they are bound form a ring;
(12) —NHC(O)($C_1$–$C_6$)alkyl;
(13) —NHC(O)O($C_1$–$C_6$)alkyl;
(14) —NHC(O)NH($C_1$–$C_6$)alkyl;
(15) —NHSO$_2$($C_1$–$C_6$)alkyl;
(18) —OH;
(17) —OC(O)($C_1$–$C_6$)alkyl;
(18) —Oaryl;
(19) —Oar($C_1$–$C_6$)alkyl;
(20) -aryl;
(21) -aryl substituted with one or more substituents independently selected from: halogen, CF$_3$, ($C_1$–$C_6$) alkyl, ($C_1$–$C_6$)alkoxy, OCF$_3$, NH$_2$, or CN;
(22) -heteroaryl;
(23) -heteroaryl substituted with one or more substituents independently selected from: halogen, CF$_3$, ($C_1$–$C_6$)alkyl, ($C_1$–$C_6$)alkoxy, OCF$_3$, NH$_2$, or CN;
(24) -a group selected from:

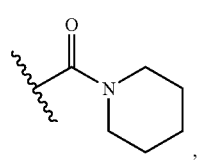
(8.0)

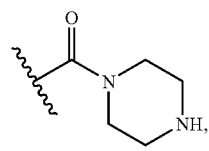
(9.0)

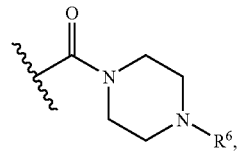
(10.0)

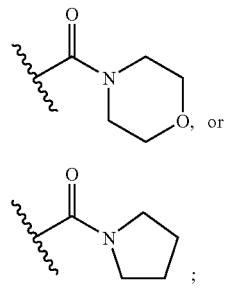
(11.0)

(12.0)

(25) —C(O)N(($C_1$–$C_6$)alkyl)$_2$ wherein each alkyl group is independently selected; or
(26) —C(O)N(($C_1$–$C_6$)alkyl)$_2$ wherein each alkyl group is independently selected and wherein the alkyl groups taken together with the nitrogen atom form a heterocycloalkyl ring;

(E) each $R^3$ is independently selected from H or —($C_1$–$C_3$)alkyl;

(F) each $R^4$ is independently selected from:
(1) —($C_1$–$C_3$)alkyl;
(2) —CH; or
(3) —O($C_1$–$C_3$)alkyl;

(G) $R^5$ is selected from:
(1) —($C_1$–$C_6$)alkyl;
(2) -aryl;
(3) -heteroaryl;
(4) —($C_1$–$C_3$)alkylene-O($C_1$–$C_3$)alkyl;
(5) —($C_1$–$C_6$)alkylene-S(O)$_{0-2}$($C_1$–$C_3$)alkyl;
(6) —($C_1$–$C_6$)alkylene-S(O)$_{0-2}$NH($C_1$–$C_3$)alkyl;
(7) —C(O)($C_1$–$C_6$)alkyl;
(8) —C(O)aryl;
(9) —C(O)ar($C_1$–$C_3$)alkyl;
(10) —C(O)heteroaryl;
(11) —C(O)heteroar($C_1$–$C_3$)alkyl;
(12) —C(O)O($C_1$–$C_6$)alkyl;
(13) —C(O)NH($C_1$–$C_6$)alkyl;
(14) —C(O)N(($C_1$–$C_6$)alkyl)$_2$ wherein each $C_1$–$C_6$alkyl group is the same or different;
(15) —C(O)N(($C_1$–$C_6$)alkyl)$_2$ wherein each $C_1$—$C_6$alkyl group is the same or different and wherein the $C_1$–$C_6$ alkyl groups taken together with the nitrogen to which they are bound form a heterocycloalkyl ring;
(16) —C(O)($C_1$–$C_3$)alkylene-NH($C_1$–$C_3$)alkyl;
(17) —C(O)($C_1$–$C_3$)alkylene-N($C_1$–$C_3$)alkyl)$_2$ wherein each alkyl group is independently selected;
(18) —SO$_2$($C_1$–$C_8$)alkyl;
(19) —SO$_2$NH($C_1$–$C_6$)alkyl;
(20) —SO$_2$N($C_1$–$C_6$)alkyl)$_2$ wherein each $C_1$–$C_6$alkyl is the same or different;
(21) —SO$_2$N(($C_1$–$C_6$)alkyl)$_2$ wherein each $C_1$–$C_6$alkyl is the same or different, and wherein the $C_1$–$C_6$alkyl groups taken together with the nitrogen to which they are bound form a heterocycloalkyl ring; or

(22) a group of the formula:

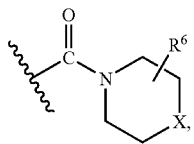 (13.0)

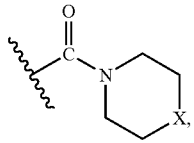 (13.1)

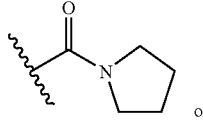 (14.0)

or

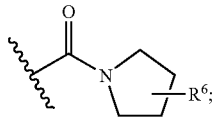 (15.0)

(H) $R^6$ is —H or —$(C_1$–$C_6)$ alkyl;
(I) X is selected from: $CH_2$, O, S, SO, $SO_2$, or N—$R^7$;
(J) $R^7$ is selected from:
  (1) —$(C_1$–$C_6)$alkyl;
  (4) —$(C_3$–$C_6)$cycloalkyl;
  (5) —(C1–C3)alkylene-(C3–C6)cycloalkyl;
  (4) -aryl;
  (5) -ar$(C_1$–$C_3)$alkyl;
  (6) -heteroaryl;
  (7) -heteroar$(C_1$–$C_3)$alkyl;
  (8) —C(O)$(C_1$–$C_6)$alkyl;
  (9) —C(O)aryl;
  (10) —C(O)ar$(C_1$–$C_3)$alkyl;
  (11) —C(O)heteroaryl;
  (12) —C(O)heteroar$(C_1$–$C_3)$alkyl;
  (13) —C(O)O$(C_1$–$C_6)$alkyl;
  (14) —C(O)NH$(C_1$–$C_6)$alkyl;
  (15) —C(O)N$((C_1$–$C_6)$alkyl$)_2$ wherein each $C_1$–$C_6$alkyl group is the same or different;
  (16) —C(O)N$((C_1$–$C_6)$alkyl$)_2$ wherein each $C_1$–$C_6$alkyl group is the same or different, and the $C_1$–$C_6$alkyl groups taken together with the nitrogen to which they are bound form a heterocycloalkyl ring;
  (17) —C(O)$(C_1$–$C_3)$alkylene-NH$(C_1$–$C_3)$alkyl;
  (18) —C(O)$(C_1$–$C_3)$alkylene-N$((C_1$–$C_3)$alkyl$)_2$ wherein the $C_1$–$C_3$alkyl groups are the same or different; or
  (19) —$(C_1$–$C_3)$alkylene-O—$(C_1$–$C_3)$alkyl;
(K) n and p are both 1;
(L) r is 0 to 3;
(M) q is 0 to 3; and
(N) t is 0 to 3.

* * * * *

UNITED STATES PATENT AND TRADEMARK OFFICE
CERTIFICATE OF CORRECTION

PATENT NO. : 7,122,675 B2  
APPLICATION NO. : 10/210803  
DATED : October 17, 2006  
INVENTOR(S) : Josien et al.

Page 1 of 1

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (459) days Delete the phrase "by 459" and insert -- by 579 days--

Signed and Sealed this

Twenty-seventh Day of November, 2007

JON W. DUDAS  
*Director of the United States Patent and Trademark Office*